(12) United States Patent
Bembridge et al.

(10) Patent No.: US 8,916,695 B2
(45) Date of Patent: Dec. 23, 2014

(54) ANTIGEN BINDING PROTEINS TO ONCOSTATIN M (OSM)

(75) Inventors: Gary Peter Bembridge, Stevenage (GB); Chun-Wa Chung, Stevenage (GB); Maria Feeney, Stevenage (GB); Susannah Karen Ford, Stevenage (GB); Ian Kirby, Stevenage (GB); Ruth McAdam, Stevenage (GB)

(73) Assignee: Glaxo Group Limited (GB)

( * ) Notice: Subject to any disclaimer, the term of this patent is extended or adjusted under 35 U.S.C. 154(b) by 5 days.

(21) Appl. No.: 13/989,191

(22) PCT Filed: Nov. 21, 2011

(86) PCT No.: PCT/EP2011/070604
§ 371 (c)(1),
(2), (4) Date: May 23, 2013

(87) PCT Pub. No.: WO2012/069433
PCT Pub. Date: May 31, 2012

(65) Prior Publication Data
US 2013/0251724 A1  Sep. 26, 2013

Related U.S. Application Data

(60) Provisional application No. 61/416,495, filed on Nov. 23, 2010.

(51) Int. Cl.
*C07H 21/04* (2006.01)
*C07K 16/00* (2006.01)
*C07K 16/24* (2006.01)

(52) U.S. Cl.
CPC ......... *C07K 16/248* (2013.01); *C07K 2317/526* (2013.01); *C07K 2317/522* (2013.01); *C07K 2317/24* (2013.01); *C07K 16/244* (2013.01); *C07K 2317/51* (2013.01); *C07K 2317/515* (2013.01); *C07K 2317/76* (2013.01); *C07K 2317/524* (2013.01); *C07K 2317/565* (2013.01)
USPC ................. 536/23.53; 530/388.1; 530/388.23

(58) Field of Classification Search
None
See application file for complete search history.

(56) References Cited

U.S. PATENT DOCUMENTS 5,783,672 A       7/1998  Mosley et al.
6,706,266 B1 *   3/2004  Life ........................... 424/139.1

OTHER PUBLICATIONS

Paul, Fundamental Immunology, 3rd Edition, 1993, pp. 292-295, under the heading "Fv Structure and Diversity in Three Dimensions".*
Vajdos et al J. Mol. Biol., 2002, vol. 320, p. 415-428.*
Bendig M. M. Methods: A Companion to Methods in Enzymology, 1995; vol. 8, p. 83-93.*
Casset et al Biochem. Biophys. Res. Comm., 2003, vol. 307, p. 198-205.*
Rudikoff et al Proc. Natl. Acad. Sci.USA, 79(6):1979-1983, Mar. 1982.*
Colman P. M. Research in Immunology, 145:33-36, 1994.*

* cited by examiner

*Primary Examiner* — Shulamith H Shafer
(74) *Attorney, Agent, or Firm* — Jason C. Fedon; William T. Han

(57) ABSTRACT

The present invention concerns antigen binding proteins and fragments thereof which specifically bind Oncostatin M (OSM), particularly human OSM (hOSM) and which inhibit the binding of OSM to the gp130 receptor but does not directly interact with site II residues. The invention also concerns a method of humanizing antibodies. Further disclosed are pharmaceutical compositions, screening and medical treatment methods.

16 Claims, 18 Drawing Sheets

Figure 1: Human gp130 ELISA
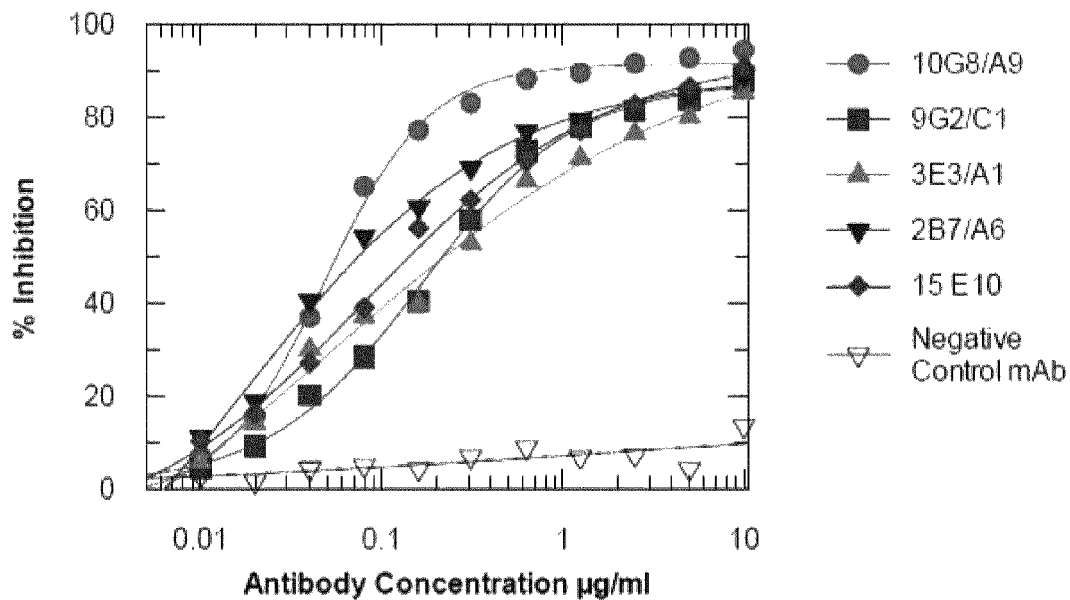
Figure 2: KB Cell Assay
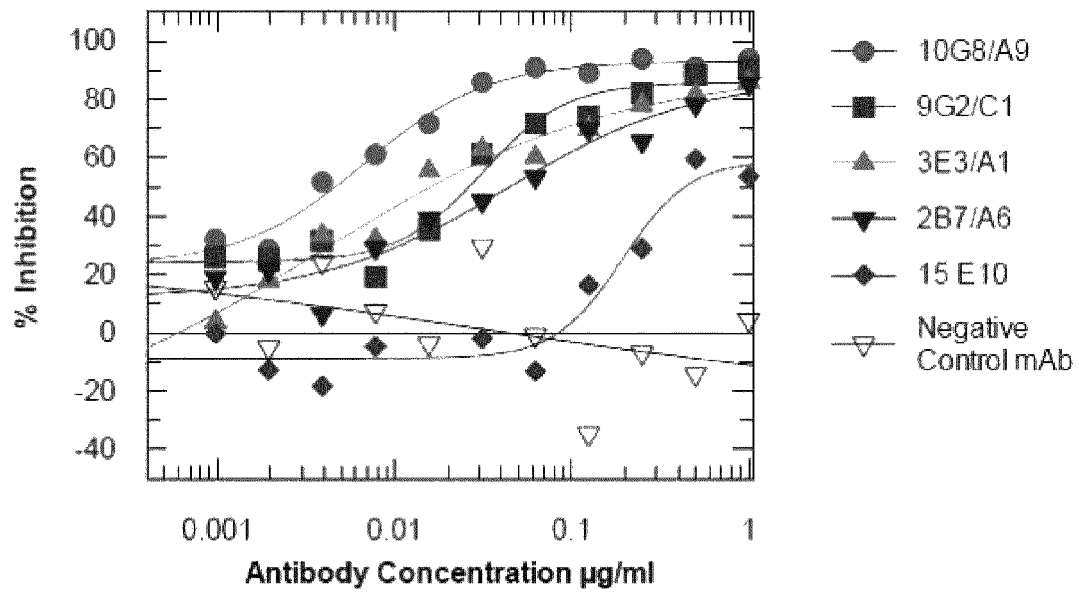

Figure 3: KB Cell Assay
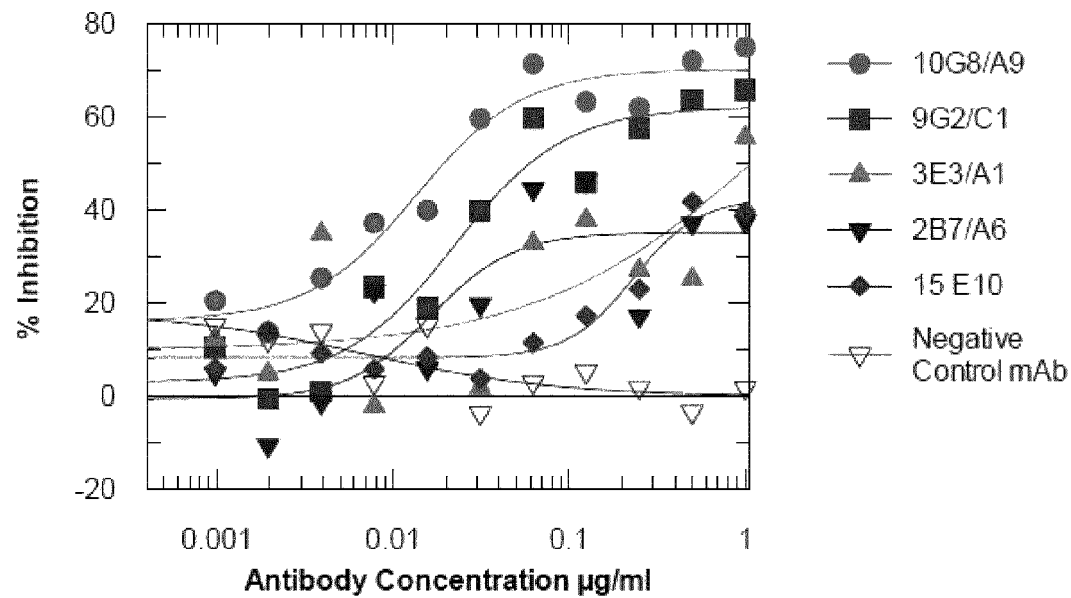
Figure 4: Endogenous OSM Human gp130 Assay
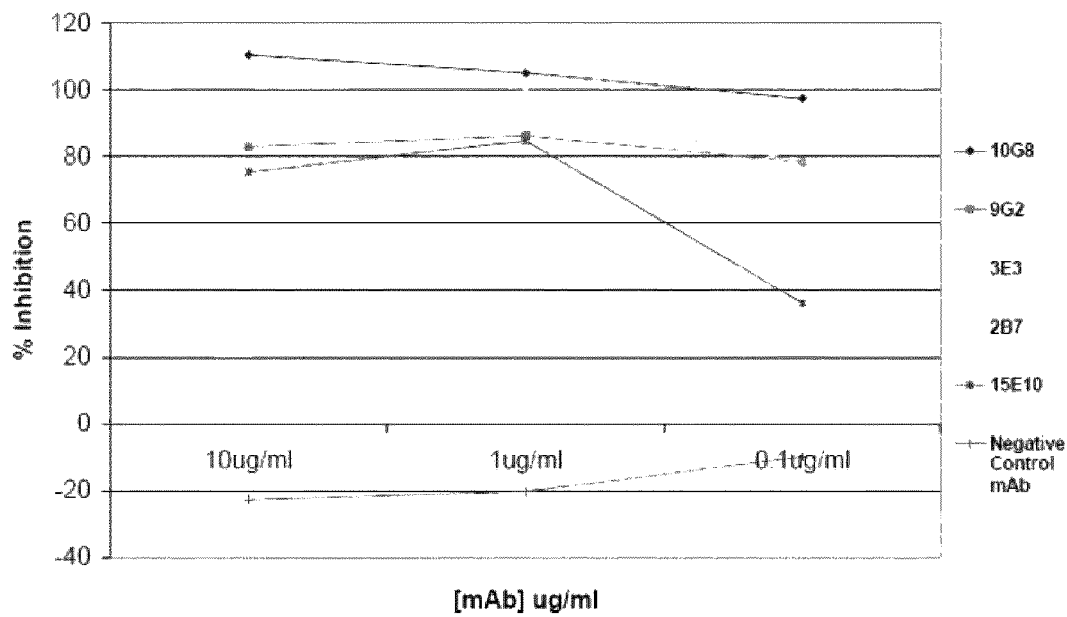

Figure 5: KB Cell Assay
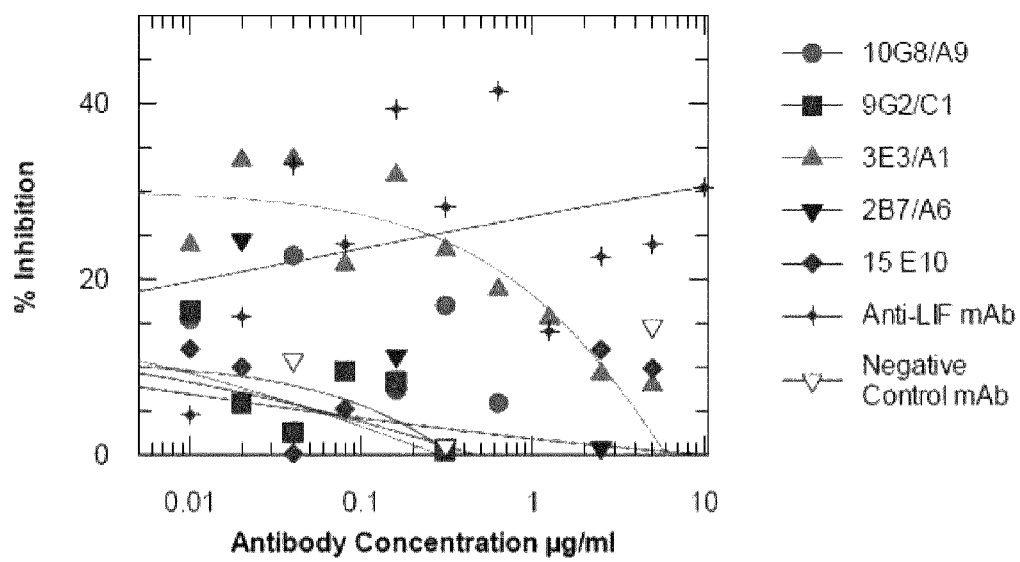
Figure 6: KB Cell Assay
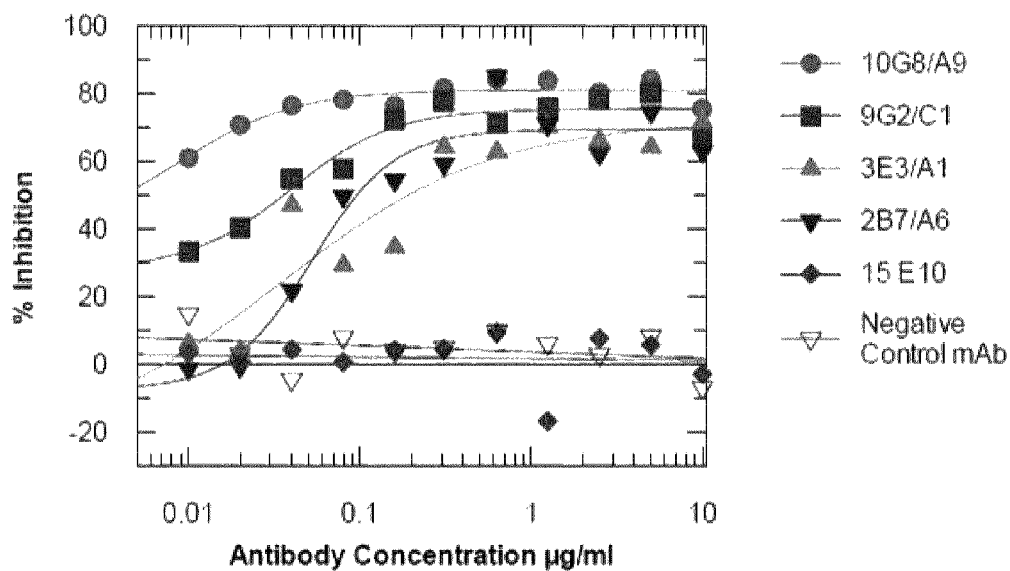

Figure 7

```
                    E V Q L V E S G G G L V E P G G S L K L S C A A S G F T F S   Majority
                                    10                  20                  30
SEQ ID NO: 34    1  E V Q L V E S G G G L V K P G G S L K L S C A A S G F T F S   2B7 VH protein
SEQ ID NO: 30    1  E V Q L V E S G G D L V K P G G S L K L S C V P S G F T F S   3E3 VH protein
SEQ ID NO: 38    1  E V Q L V E S G G G L V E P G G S L K L S C A A S G F T F S   9G2 VH protein
SEQ ID NO: 42    1  E M Q L V E S G E G L V E P G G S L K L S C A A S G F T F S   10G8 VH protei N Y A M S W V R Q T P E K R L E W V A T I S D G G S F T Y Y   Majority
                                    40                  50                  60
SEQ ID NO: 34   31  N Y A M S W V R Q T P E K R L E W V A T I S D G G Y T Y Y     2B7 VH protein
SEQ ID NO: 30   31  S Y A M S W V R Q T P E K R L E W V A T I S D G G S F T Y Y   3E3 VH protein
SEQ ID NO: 38   31  N Y A M S W V R Q T P E K R L E W V A T I S D G G S F T Y Y   9G2 VH protein
SEQ ID NO: 42   31  N Y A M S W V R Q T P E K S L E W V A T I S D G G S F T Y Y   10G8 VH protei L D N V Q G R F T I S R D N A K N N L Y L Q M S H L K S D D   Majority
                                    70                  80                  90
SEQ ID NO: 34   61  L D N G Q G R F T I S R D N A K N N L Y L Q M S H L K S E D   2B7 VH protein
SEQ ID NO: 30   61  F A N I Q G R F T I S R D N T K N N L Y L Q M N H L K S E D   3E3 VH protein
SEQ ID NO: 38   61  L D N V K G R F T I S R D N A K N N L Y L Q M S H L K S D D   9G2 VH protein
SEQ ID NO: 42   61  L D N V R G R F T I S R D N A K N N L Y L Q M S H L K S D D   10G8 VH protei T A M Y Y C A R D V G L T T F W Y F D V W G T G T T V T V S   Majority
                                    100                 110                 120
SEQ ID NO: 34   91  T A M Y Y C A R D V G L T T F W Y F D V W G T G T T V T V S   2B7 VH protein
SEQ ID NO: 30   91  A G M Y Y C A R D V G L T T F W Y F D V W G T G T T V T V S   3E3 VH protein
SEQ ID NO: 38   91  T A M Y Y C A R D V G H T T F W Y F D V W G T G T T V T V S   9G2 VH protein
SEQ ID NO: 42   91  T A M Y Y C A R D V G H T T F W Y F D V W G S G T A V T V S   10G8 VH protei S                                                             Majority SEQ ID NO: 34  121  S                                                             2B7 VH protein
SEQ ID NO: 30  121  S                                                             3E3 VH protein
SEQ ID NO: 38  121  S                                                             9G2 VH protein
SEQ ID NO: 42  121  S                                                             10G8 VH protei
```

Decoration 'Decoration #1': Box residues that differ from the Consensus.

Figure 8

```
                    D I V L T Q S P V S L V I S L G Q R A T I S C R A S K S V S   Majority
                                    10                  20                  30
SEQ ID NO: 36    1  D I V L T Q S P V S L V I S L G Q R A T I S C R A S K S V S   2B7 VL protein
SEQ ID NO: 32    1  D I V L T Q S P A S L T I S L G Q R A T I S C R A S K S V S   3E3 VL protein
SEQ ID NO: 40    1  D I V L T Q S P V F L V I S L G Q R A T I S C R A S K S V S   9G2 VL protein
SEQ ID NO: 44    1  D I V L T Q S P V F L V V S L G Q R A T I S C R A S K S V S   10G8 VL protei A S G Y N F M H W Y Q Q K P G Q P P K V L I K Y A S N L E S   Majority
                                    40                  50                  60
SEQ ID NO: 36   31  P S G Y N F M H W Y Q R P G Q P P K L L I T Y A S N L E S     2B7 VL protein
SEQ ID NO: 32   31  P S G Y D F M H W Y Q Q K P G Q P P K L L I K Y A S E L E S   3E3 VL protein
SEQ ID NO: 40   31  A S G Y N F M H W Y Q Q K P G Q P P K V L I K Y A S N L E S   9G2 VL protein
SEQ ID NO: 44   31  A A G Y N F M H W Y Q Q K P G Q P P K V L I K Y A S N L E S   10G8 VL protei G V P A R F S G S G S G T D F T L N I H P V E E E D A A T Y   Majority
                                    70                  80                  90
SEQ ID NO: 36   61  G V P A R F S G S G S G T D F T L N I H P V E E E D A A T Y   2B7 VL protein
SEQ ID NO: 32   61  G V P G R F S G S G S G T D F T L N I H P V E E E D A A T Y   3E3 VL protein
SEQ ID NO: 40   61  G V P A R F S G S G S G T D F T L N I H P V E E E D A V T Y   9G2 VL protein
SEQ ID NO: 44   61  G V P A R F S G S G S G T D F T L N I H P V E E E D A V T Y   10G8 VL protei Y C Q H S R E F P P F T F G G G T K L E I K                   Majority
                                    100                 110
SEQ ID NO: 36   91  Y C Q H S R E F P P F T F G G G T R L E I K                   2B7 VL protein
SEQ ID NO: 32   91  F C Q H S R E F P P F T F G G G T K L E I K                   3E3 VL protein
SEQ ID NO: 40   91  Y C Q H S R E F P P F T F G G G T K L E I K                   9G2 VL protein
SEQ ID NO: 44   91  Y C Q H S R E F P P F T F G G G T N L E I K                   10G8 VL protei
```

Decoration 'Decoration #1': Box residues that differ from the Consensus.

Figure 9
Phylogenetic tree of VH back ups vs 15E10 VL.meg ClustalW (Slow/Accurate, Gonnet)
10 December 2007 17:24
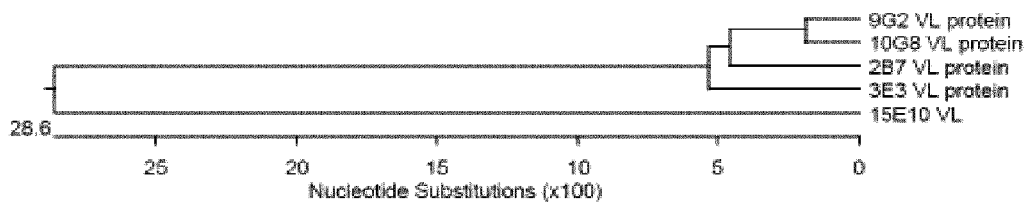
Sequence pair distances of VH back ups vs 15E10 VL.meg ClustalW (Slow/Accurate, Gonnet)
10 December 2007 17:23
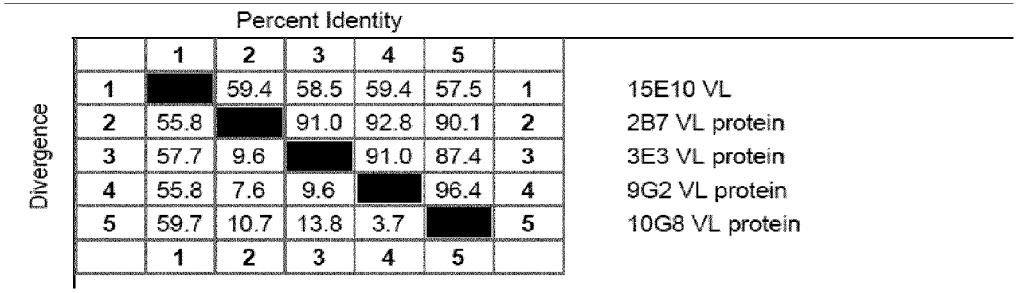
Figure 10
Phylogenetic tree of VH back ups vs 15E10 VH.meg ClustalW (Slow/Accurate, Gonnet)
10 December 2007 17:16
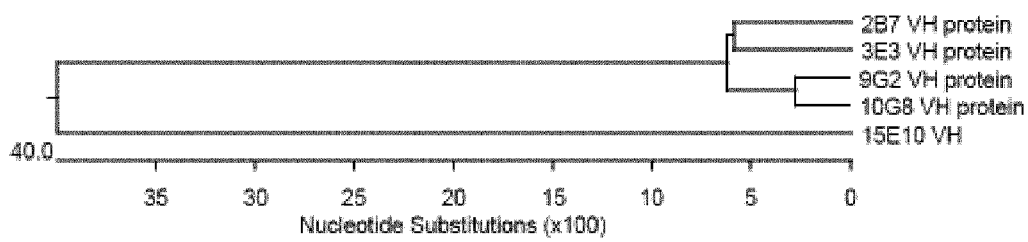
Sequence pair distances of VH back ups vs 15E10 VH.meg ClustalW (Slow/Accurate, Gonnet)
10 December 2007 17:16
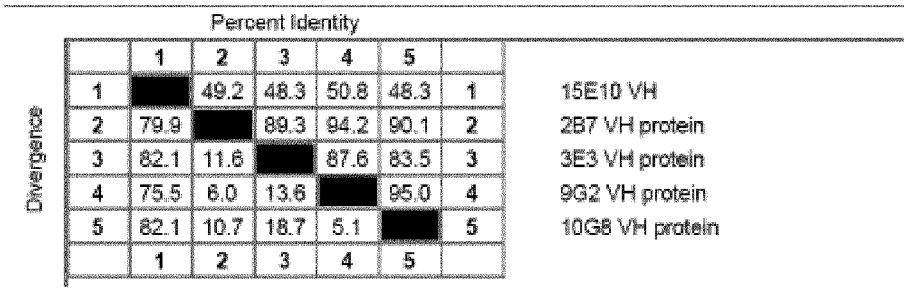

Figure 11: Direct Human OSM Binding ELISA
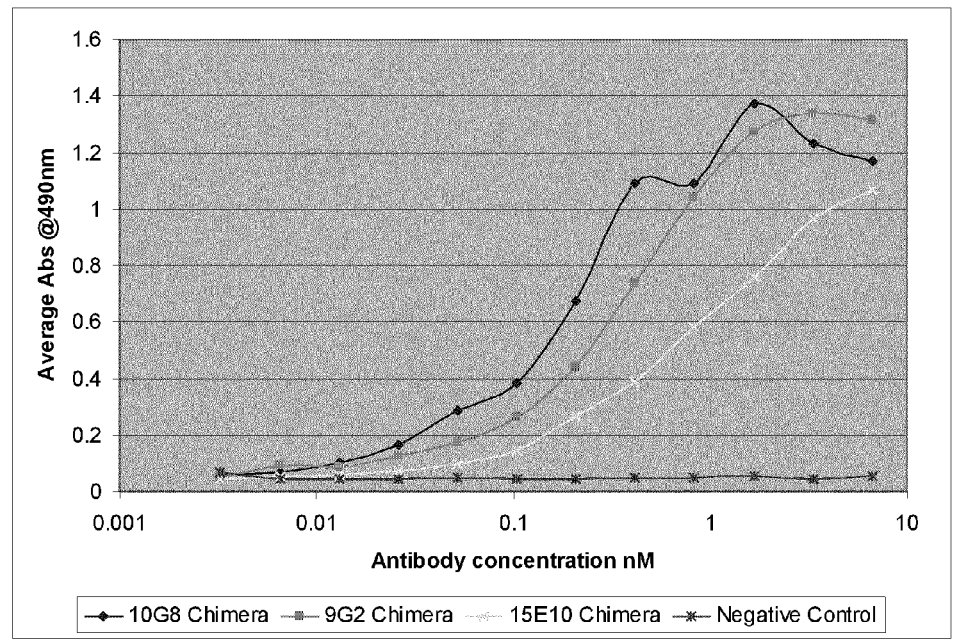
Figure 12: Human gp130 ELISA
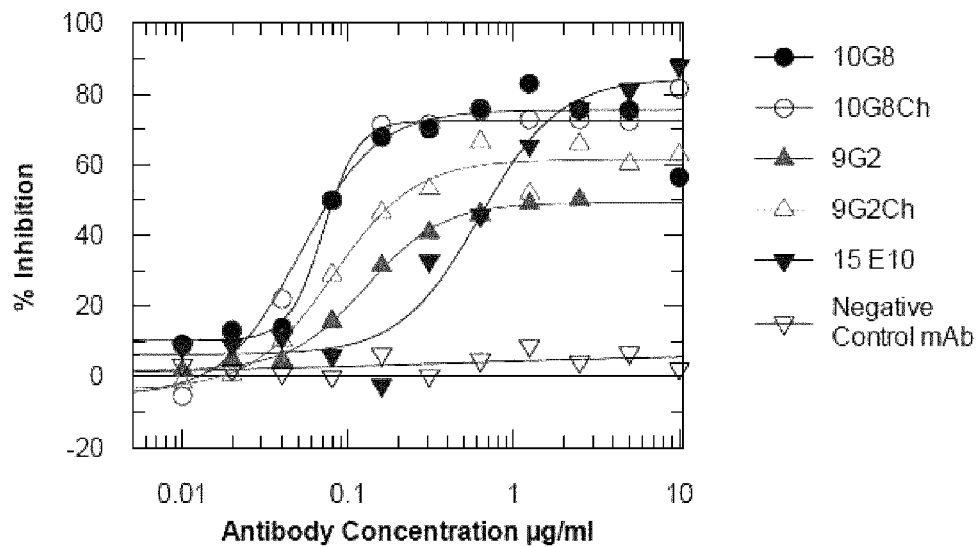

Figure 13: KB Cell Assay
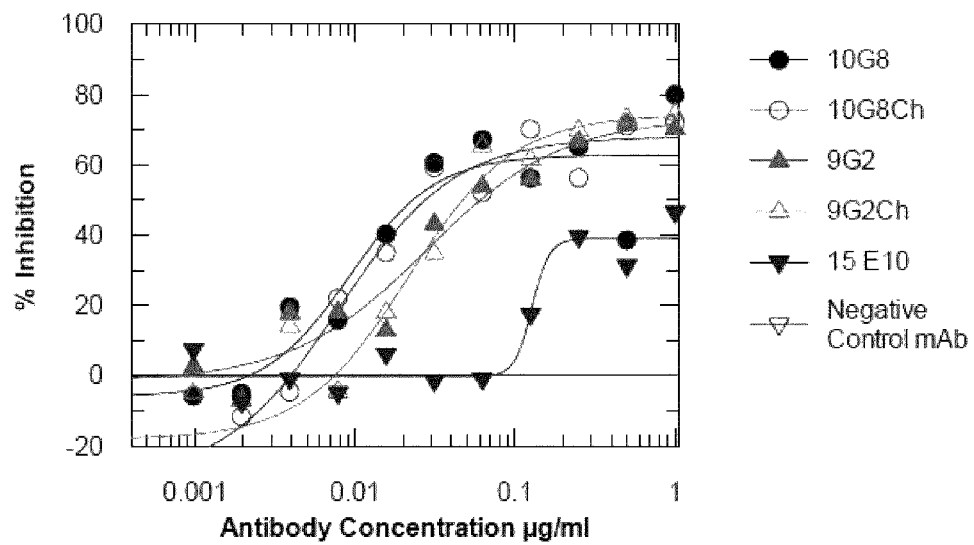
Figure 14: KB Cell Assay
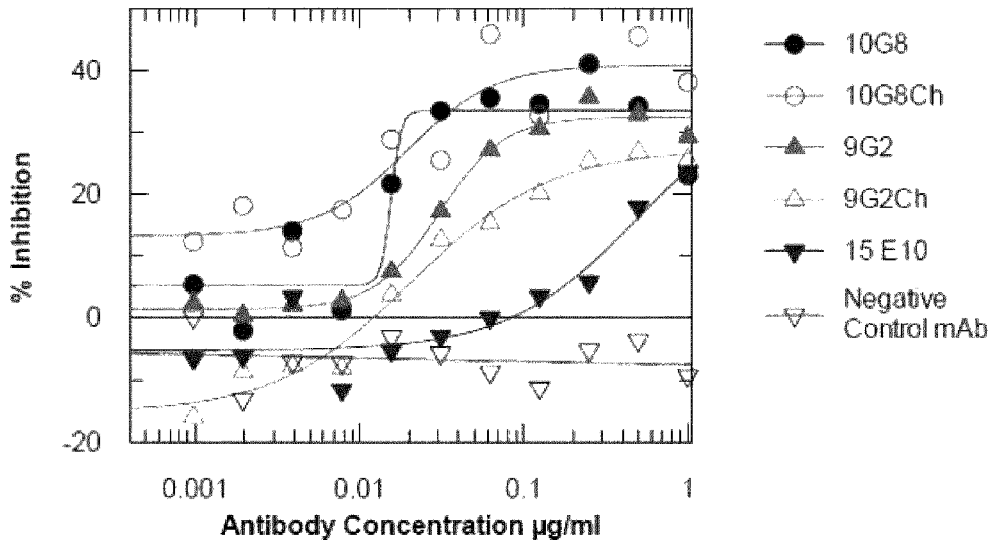

Figure 15: Endogenous OSM Human gp130 Assay
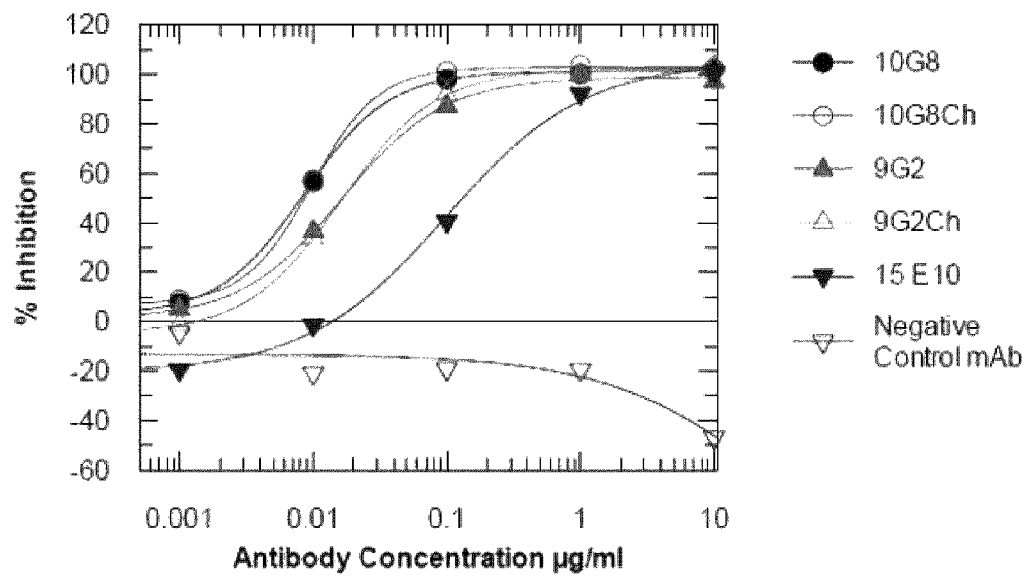
Figure 16: Human LIF KB Cell Assay
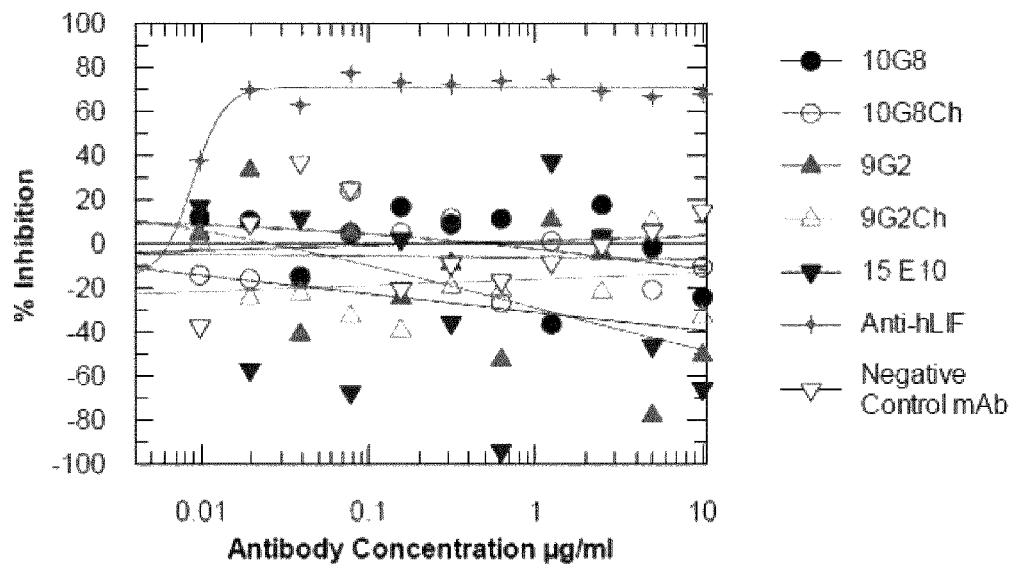

Figure 17: KB Cell Assay
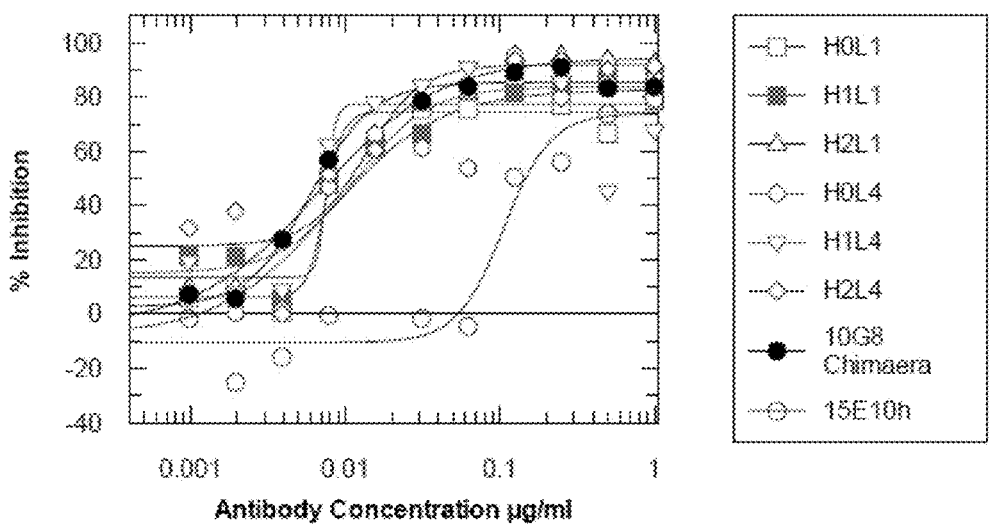
Figure 18: Human gp130 ELISA
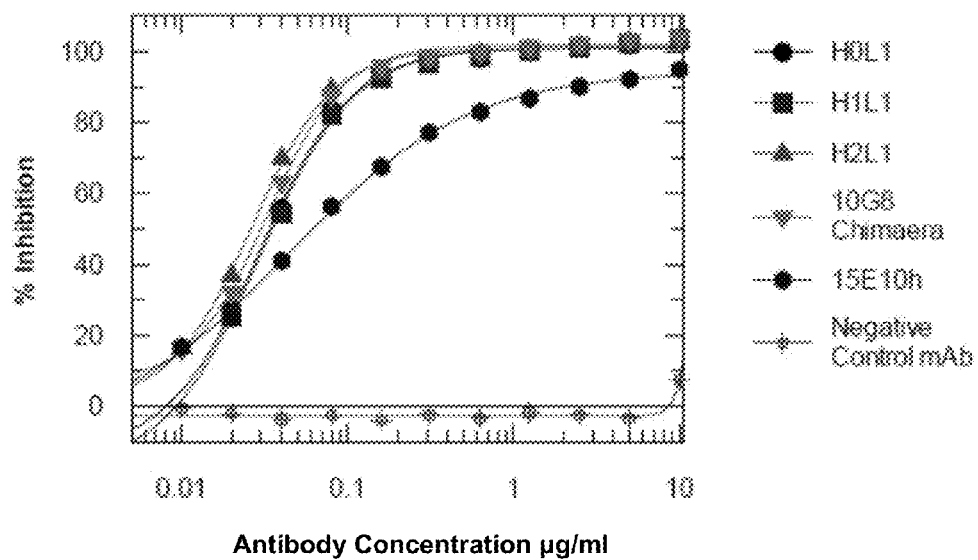

Figure 19: Human OSM-10G8 mAb Binding Complex-
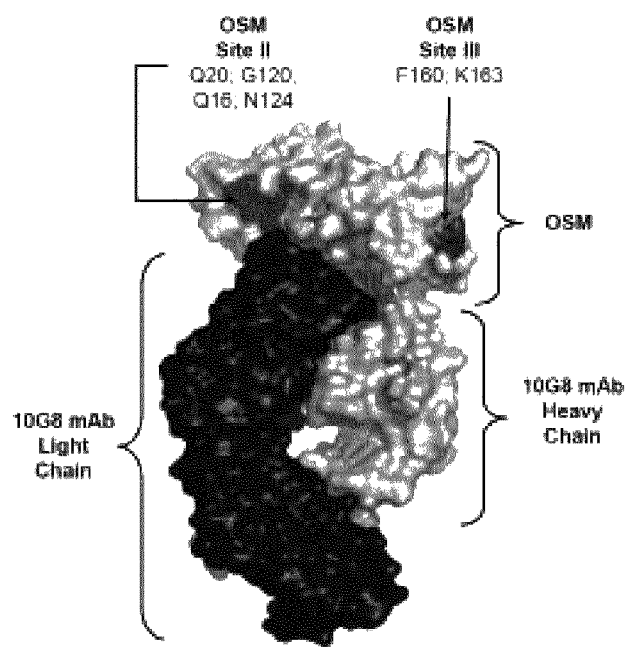
Figure 20: KB Cell Assay-
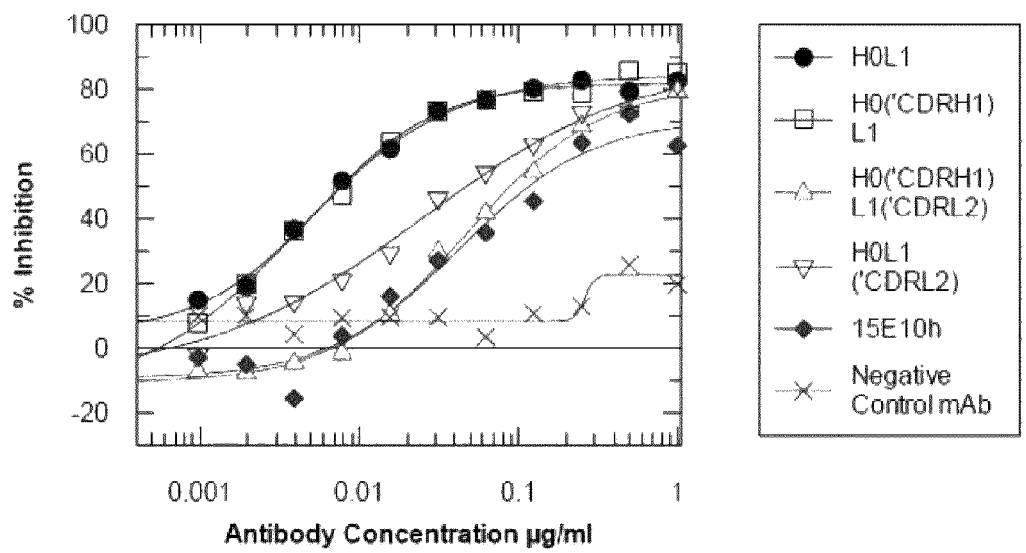

Figure 21: Human gp130 ELISA-
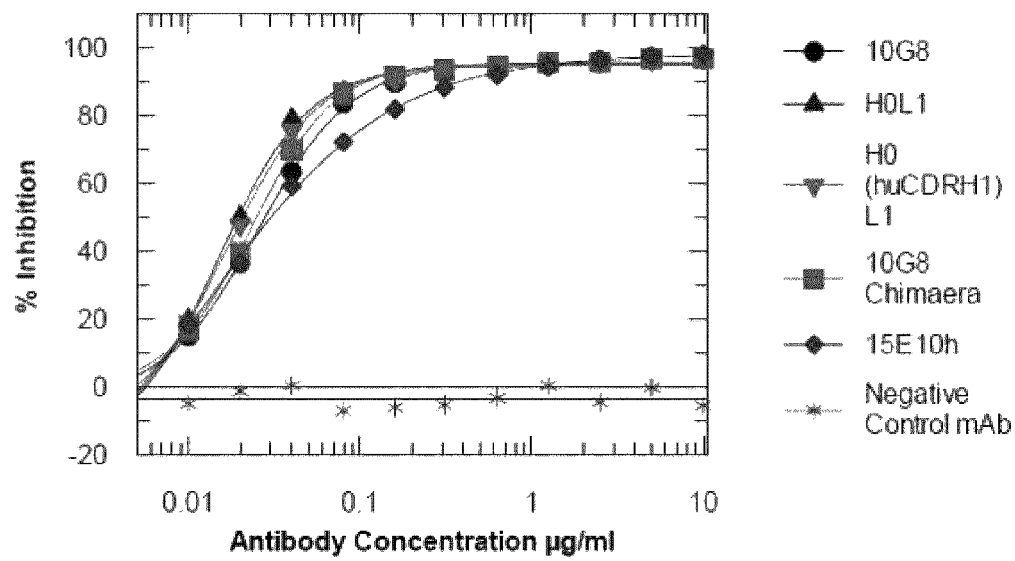
Figure 22: KB Cell Assay-
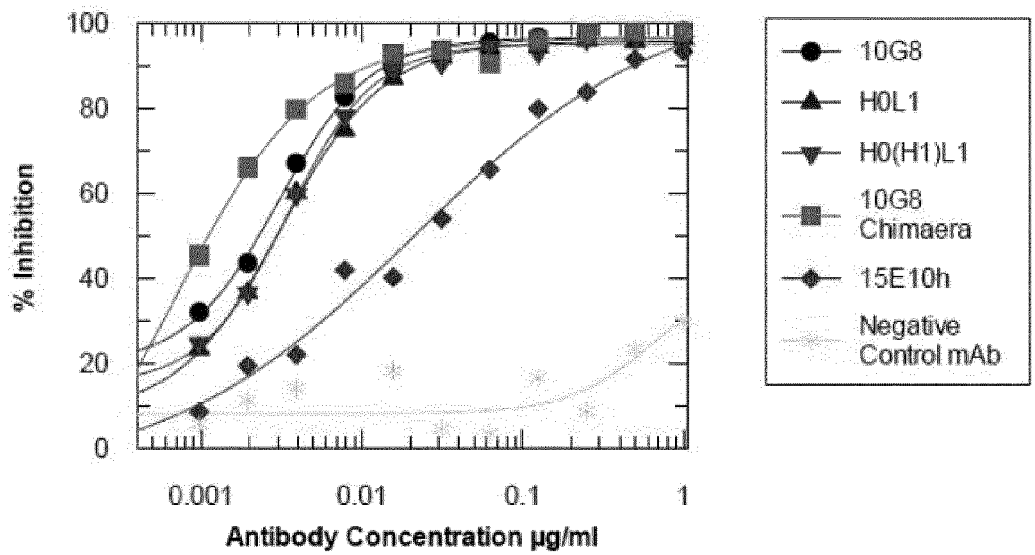

Figure 23: KB Cell Assay-
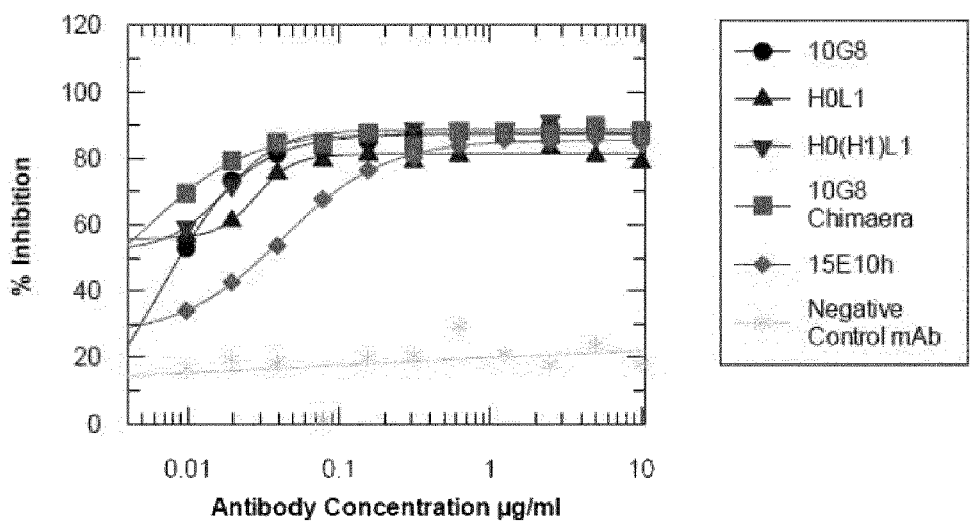
Figure 24:
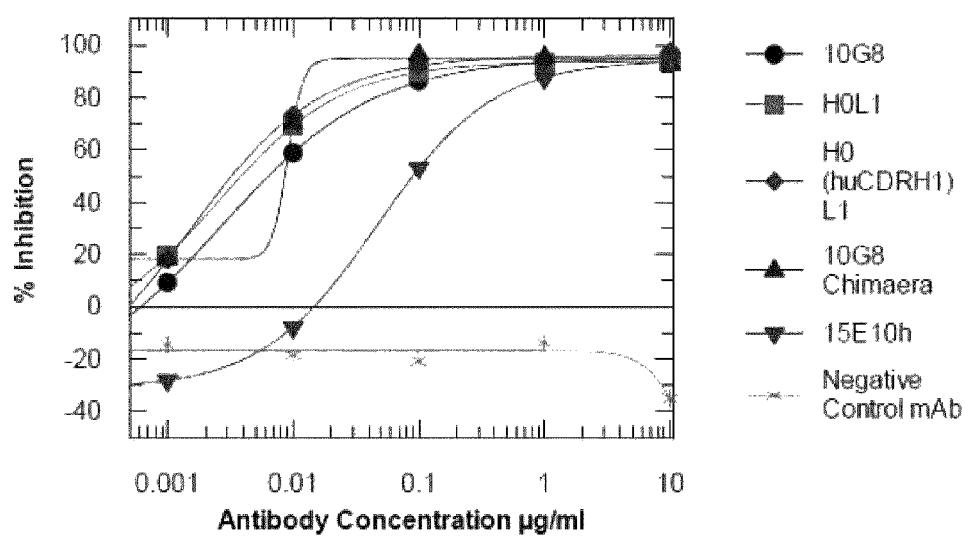

Figure 25:
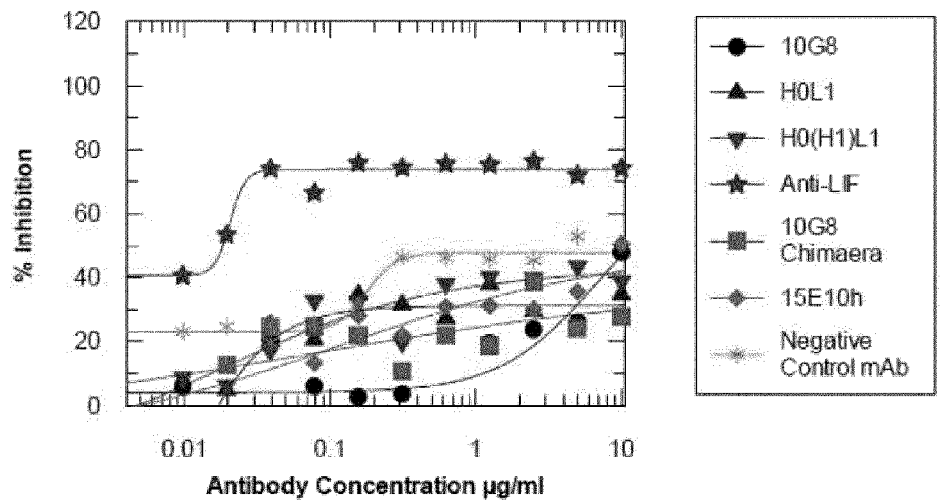
Figure 26: Human Hepatocyte Assay- SAA
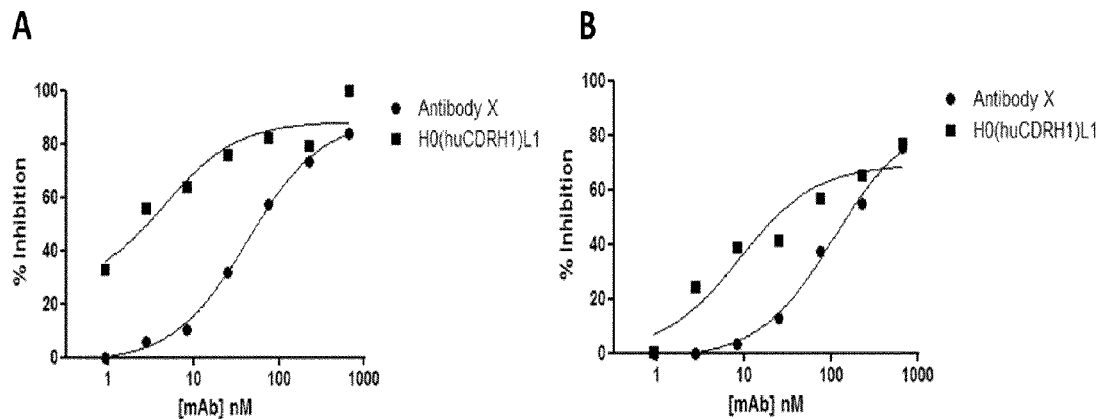
Figure 27: Human Hepatocyte Assay- CRP
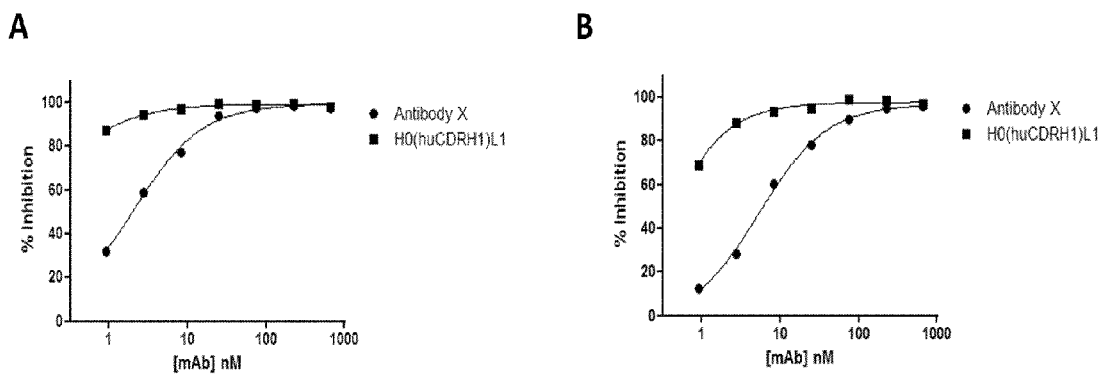

Figure 28: Human Fibroblast-Like Synovioctye Assay- IL-6
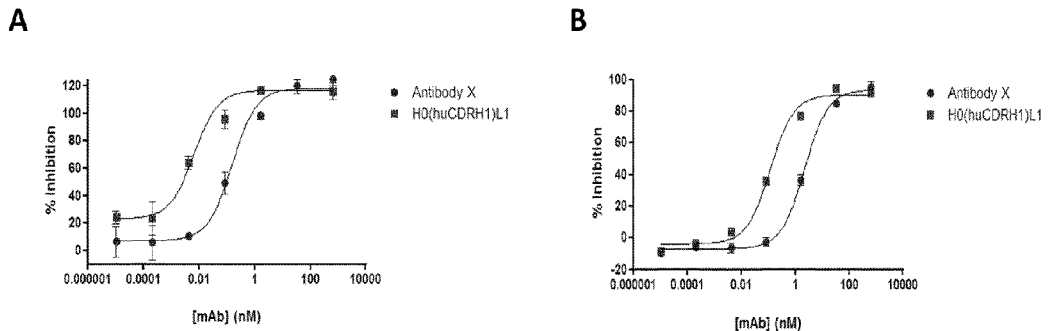
Figure 29: Human Fibroblast-Like Synovioctye Assay- MCP-1
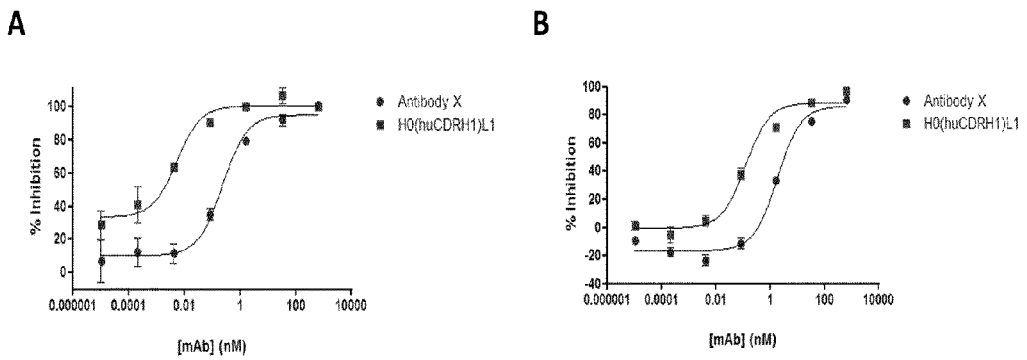
Figure 30: Human Umbilical-Vein Endothelia Cell Assay
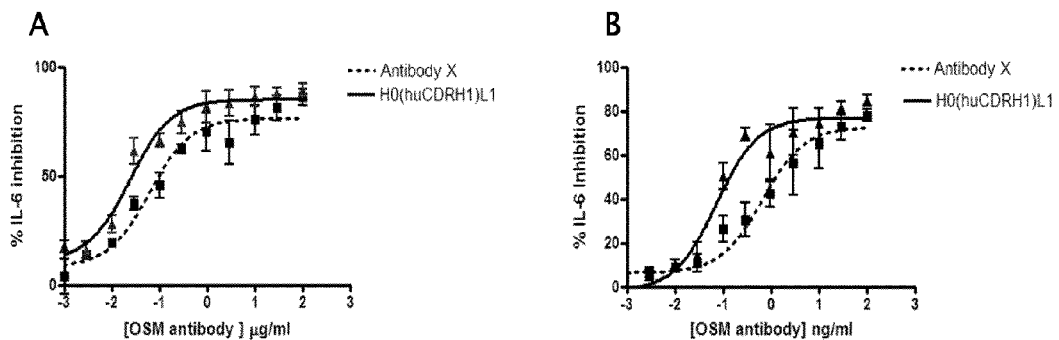

Figure 31: Human Lung Fibroblast Assay- MCP-1
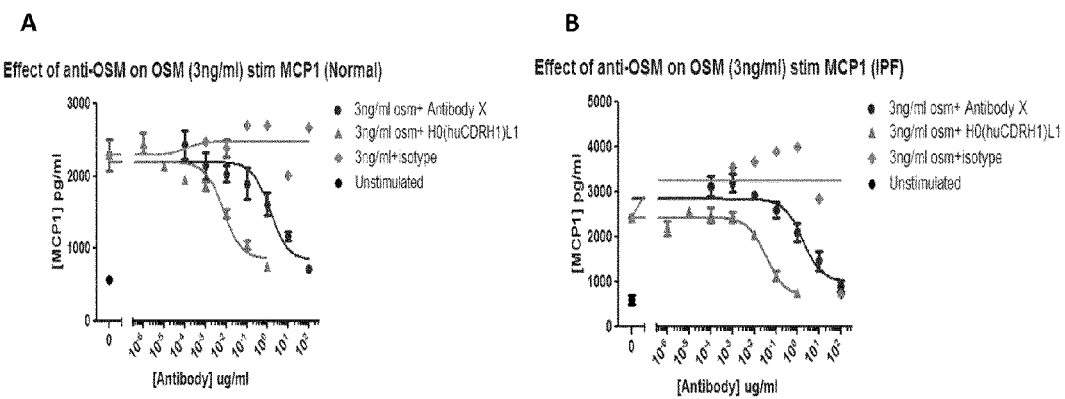
Figure 32: Human Lung Fibroblast Assay- IL-6
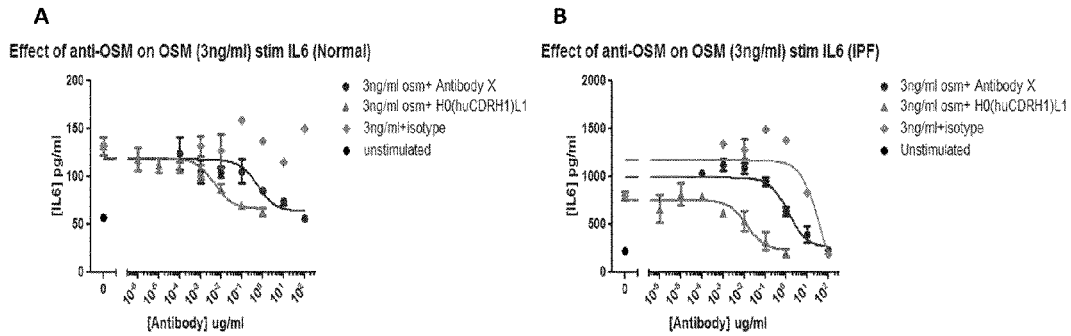

Figure 33

| Pos | 95 | 96 | 97 | 98 | 99 | 100 | 100A | 100B | 100C | 100D | 101 | 102 |
|---|---|---|---|---|---|---|---|---|---|---|---|---|
| Ala | 5.76 E-10 | 5.72 E-10 | 4.86 E-10 | 6.59 E-10 | 5.41 E-10 | 8.55 E-09 | 8.10 E-09 | 4.81 E-09 | 3.94 E-10 | 8.69 E-10 | 1.55 E-09 | 3.38 E-10 |
| Cys | | 6.64 E-10 | 6.51 E-10 | 1.50 E-09 | 7.08 E-10 | 8.95 E-09 | 8.92 E-09 | 8.12 E-09 | | 5.86 E-10 | | |
| Asp | 4.42 E-10 | | | 4.94 E-10 | 4.24 E-09 | | 4.27 E-08 | 2.32 E-08 | | 6.72 E-10 | 3.55 E-10 | |
| Glu | 7.85 E-10 | | 1.10 E-09 | | 1.28 E-09 | | | 4.91 E-10 | 4.82 E-10 | 6.88 E-10 | 4.26 E-10 | |
| Phe | | 6.1 E-10 | 6.37 E-10 | 3.25 E-10 | 2.54 E-07 | | 4.47 E-10 | 3.37 E-09 | 3.65 E-10 | 4.50 E-10 | 2.60 E-09 | 4.25 E-10 |
| Gly | 5.17 E-10 | 4.88 E-10 | 3.07 E-10 | 1.11 E-09 | 5.25 E-09 | 1.81 E-08 | 6.31 E-08 | 2.21 E-08 | 3.88 E-10 | 6.61 E-10 | 7.10 E-10 | 4.06 E-10 |
| His | 4.99 E-10 | 4.80 E-10 | | 1.74 E-10 | 1.58 E-08 | | 3.97 E-08 | 3.62 E-08 | 1.20 E-09 | | | |
| Ile | | | | 7.16 E-09 | 1.69 E-09 | 1.97 E-08 | 2.46 E-08 | 4.55 E-08 | | | | |
| Lys | | 6.71 E-10 | | 2.45 E-08 | 4.06 E-09 | 4.31 E-09 | | 4.71 E-08 | | 8.73 E-10 | 2.83 E-09 | |
| Leu | 5.68 E-10 | 5.55 E-10 | 2.19 E-09 | 7.42 E-10 | 1.56 E-09 | 4.20 E-08 | 3.35 E-09 | 1.62 E-08 | 4.24 E-10 | | | 4.26 E-10 |
| Met | 6.49 E-10 | | 8.09 E-10 | 6.93 E-09 | 1.62 E-09 | | 5.19 E-09 | 4.03 E-08 | | | | |
| Asn | | | | | 1.33 E-09 | | 6.58 E-09 | 4.02 E-08 | | | | |
| Pro | 4.42 E-10 | 2.35 E-09 | 3.15 E-08 | 9.86 E-10 | 5.53 E-10 | 3.65 E-08 | | 1.14 E-08 | | 1.05 E-09 | 5.01 E-09 | 4.11 E-10 |
| Gln | 5.70 E-10 | | | 7.29 E-10 | | | 1.46 E-08 | 3.35 E-09 | 1.17 E-09 | | 1.10 E-09 | 3.37 E-10 |

Figure 33 Cont.
| | | | | | | | | | | | | |
|---|---|---|---|---|---|---|---|---|---|---|---|---|
| Arg | 6.84 E-09 | 1.56 E-08 | 1.85 E-09 | 3.02 E-09 | 6.80 E-09 | | | 2.13 E-08 | 1.09 E-09 | 1.34 E-09 | 2.18 E-09 | 5.33 E-10 |
| Ser | 7.60 E-10 | 4.67 E-10 | 6.32 E-10 | 1.09 E-09 | 8.27 E-10 | 1.65 E-09 | 1.83 E-08 | 7.74 E-09 | 1.20 E-09 | 6.61 E-10 | 7.72 E-10 | 4.44 E-10 |
| Thr | 6.32 E-10 | 4.97 E-10 | 3.64 E-09 | 1.66 E-09 | 3.99 E-10 | 4.57 E-10 | 3.34 E-08 | 8.57 E-09 | 1.09 E-09 | 5.91 E-10 | 7.07 E-10 | |
| Val | 5.70 E-10 | 4.88 E-10 | 2.01 E-09 | 1.00 E-09 | 7.14 E-10 | 1.45 E-08 | 9.05 E-09 | 4.12 E-08 | 5.60 E-10 | 6.75 E-10 | 4.40 E-10 | 4.26 E-10 |
| Trp | 1.86 E-08 | 9.79 E-10 | 1.67 E-09 | 3.17 E-10 | 4.99 E-09 | | 6.90 E-09 | 4.95 E-10 | 6.87 E-10 | 7.11 E-10 | 2.07 E-10 | 5.33 E-10 |
| Tyr | | 6.78 E-10 | | 2.07 E-09 | 4.44 E-10 | | 1.41 E-08 | 6.78 E-09 | 3.64 E-10 | 5.09 E-10 | | |
 no binding
BOLD   WT residue
 3x decrease in binding
 Data generated in a separate experiment

SEQUENCE LISTING

<160> NUMBER OF SEQ ID NOS: 84

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Asn Tyr Ala Met Ser
 1               5

<210> SEQ ID NO 2
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

```
Thr Ile Ser Asp Gly Gly Ser Phe Thr Tyr Tyr Leu Asp Asn Val Arg
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Asp Val Gly His Thr Thr Phe Trp Tyr Phe Asp Val
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Arg Ala Ser Lys Ser Val Ser Ala Ala Gly Tyr Asn Phe Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Tyr Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Leu His Ser Arg Glu Phe Pro Phe Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

Ser Tyr Ala Met Ser
1               5

<210> SEQ ID NO 8
<211> LENGTH: 16
<212> TYPE: PRT
<213> ORGANISM: Artificial Sequence
<220> FEATURE:
```

```
<223> OTHER INFORMATION: Amino acid sequence identified using molecular
      biology techniques.

<400> SEQUENCE: 8

Thr Ile Ser Asp Gly Gly Ser Phe Thr Tyr Tyr Phe Ala Asn Ile Gln
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Asp Val Gly Leu Thr Thr Phe Trp Tyr Phe Asp Val
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Arg Ala Ser Lys Ser Val Ser Pro Ser Gly Tyr Asp Phe Met His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

Tyr Ala Ser Glu Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 12

Gln His Ser Arg Glu Phe Pro Phe Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 13

Asn Tyr Ala Met Ser
1               5
```

-continued

```
<210> SEQ ID NO 14
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 14

Thr Ile Ser Asp Gly Gly Gly Tyr Thr Tyr Tyr Leu Asp Asn Gly Gln
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 15

Asp Val Gly Leu Thr Thr Phe Trp Tyr Phe Asp Val
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 16

Arg Ala Ser Lys Ser Val Ser Pro Ser Ser Tyr Asn Phe Met His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 17

Tyr Ala Ser Asn Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 18

Gln His Ser Arg Glu Phe Pro Phe Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.
```

```
<400> SEQUENCE: 19

Asn Tyr Ala Met Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 20

Thr Ile Ser Asp Gly Gly Ser Phe Thr Tyr Tyr Leu Asp Asn Val Lys
1               5                   10                  15
Gly

<210> SEQ ID NO 21
<211> LENGTH: 12
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 21

Asp Val Gly His Thr Thr Phe Trp Tyr Phe Asp Val
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 22

Arg Ala Ser Lys Ser Val Ser Ala Ser Gly Tyr Asn Phe Met His
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 23

Tyr Ala Ser Asn Leu Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 24

Gln His Ser Arg Glu Phe Pro Phe Thr
1               5
```

<210> SEQ ID NO 25
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 25

```
gaaatgcaac tggtggagtc tggggaaggc ttagtggagc ctggagggtc cctgaaactc        60
tcctgtgcag cctctggatt cactttcagt aactatgcca tgtcttgggt tcgccagact       120
ccggaaaaga gcctggagtg ggtcgcaacc attagtgatg gtggtagttt cacctactat       180
ctagacaatg taaggggccg attcaccatc tccagagaca atgccaagaa caacctgtat       240
ttgcaaatga gccatttgaa gtctgacgac acagccatgt attactgtgc aagagatgtg       300
ggacatacta ccttttggta cttcgatgtc tggggctcag ggaccgcggt caccgtctcc       360
tca                                                                     363
```

<210> SEQ ID NO 26
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 26

```
Glu Met Gln Leu Val Glu Ser Gly Gly Leu Val Glu Pro Gly Gly
 1               5                  10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Ser Leu Glu Trp Val
        35                  40                  45

Ala Thr Ile Ser Asp Gly Gly Ser Phe Thr Tyr Tyr Leu Asp Asn Val
    50                  55                  60

Arg Gly Arg Phe Thr Ile Ser Arg Asp Asn Ala Lys Asn Asn Leu Tyr
65                  70                  75                  80

Leu Gln Met Ser His Leu Lys Ser Asp Asp Thr Ala Met Tyr Tyr Cys
                85                  90                  95

Ala Arg Asp Val Gly His Thr Thr Phe Trp Tyr Phe Asp Val Trp Gly
            100                 105                 110

Ser Gly Thr Ala Val Thr Val Ser Ser
        115                 120
```

<210> SEQ ID NO 27
<211> LENGTH: 333
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 27

```
gacattgtgc tgacacagtc tcctgttttc ttagttgtat ctctggggca gagggccacc        60
atctcctgta gggccagcaa aagtgtcagt gcagctggct ataatttcat gcactggtac       120
caacagaaac caggacagcc gcccaaagtc ctcatcaagt atgcatccaa cctagaatct       180
ggggtccctg ccaggttcag tggcagtggg tctgggacag acttcaccct caacatccat       240
cctgtggagg aggaggatgc tgtaacatat tactgtctgc acagtaggga gtttccgttc       300
```

```
acgttcggag gggggaccaa cctggaaata aaa                                    333
```

<210> SEQ ID NO 28
<211> LENGTH: 111
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 28

```
Asp Ile Val Leu Thr Gln Ser Pro Val Phe Leu Val Val Ser Leu Gly
1               5                   10                  15

Gln Arg Ala Thr Ile Ser Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45

Lys Val Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Val Thr Tyr Tyr Cys Leu His Ser Arg
                85                  90                  95

Glu Phe Pro Phe Thr Phe Gly Gly Gly Thr Asn Leu Glu Ile Lys
            100                 105                 110
```

<210> SEQ ID NO 29
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 29

```
gaagtgcagc tggtggagtc tgggggagac ttagtgaaac ctggagggtc cctgaaactc     60
tcctgtgtac cctctggatt cacttttcagt agttatgcca tgtcttgggt tcgccagact   120
ccggaaaaga ggctggagtg ggtcgcaacc attagtgatg gtggtagttt cacctactat   180
tttgccaata tacagggccg attcaccatc tccagagaca taccaagaa caacctatac    240 ctgcaaatga accatctgaa gtctgaggac gcaggcatgt attactgtgc aagagatgtg   300
ggccttacta cgttttggta tttcgatgtc tggggcacag ggaccacggt caccgtctcc   360
tca                                                                  363
```

<210> SEQ ID NO 30
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 30

```
Glu Val Gln Leu Val Glu Ser Gly Gly Asp Leu Val Lys Pro Gly Gly
1               5                   10                  15

Ser Leu Lys Leu Ser Cys Val Pro Ser Gly Phe Thr Phe Ser Ser Tyr
            20                  25                  30

Ala Met Ser Trp Val Arg Gln Thr Pro Glu Lys Arg Leu Glu Trp Val
        35                  40                  45
```

```
Ala Thr Ile Ser Asp Gly Gly Ser Phe Thr Tyr Tyr Phe Ala Asn Ile
        50                  55                  60

Gln Gly Arg Phe Thr Ile Ser Arg Asp Asn Thr Lys Asn Asn Leu Tyr
 65                  70                  75                  80

Leu Gln Met Asn His Leu Lys Ser Glu Asp Ala Gly Met Tyr Tyr Cys
                 85                  90                  95

Ala Arg Asp Val Gly Leu Thr Thr Phe Trp Tyr Phe Asp Val Trp Gly
            100                 105                 110

Thr Gly Thr Thr Val Thr Val Ser Ser
            115                 120

<210> SEQ ID NO 31
<211> LENGTH: 333
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 31
gacattgtgc tgacacagtc tcctgcttcc ttaactatat ctctggggca gagggccacc      60
atctcctgca gggccagcaa aagtgtcagt ccatctggct atgatttcat gcactggtat     120
caacagaagc caggacagcc gcccaaactc ctcatcaagt atgcatccga actagaatct     180
ggggtccctg gcaggttcag tggcagtggg tctgggacag atttcaccct caacatccat     240
cctgtggagg aagaagatgc tgcaacatat ttctgtcagc acagtaggga gtttccgttc     300
acgttcggag gggggaccaa gctggaaata aaa                                  333

<210> SEQ ID NO 32
<211> LENGTH: 111
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 32

Asp Ile Val Leu Thr Gln Ser Pro Ala Ser Leu Thr Ile Ser Leu Gly
  1               5                  10                  15

Gln Arg Ala Thr Ile Ser Cys Arg Ala Ser Lys Ser Val Ser Pro Ser
             20                  25                  30

Gly Tyr Asp Phe Met His Trp Tyr Gln Gln Lys Pro Gly Gln Pro Pro
         35                  40                  45

Lys Leu Leu Ile Lys Tyr Ala Ser Glu Leu Glu Ser Gly Val Pro Gly
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Phe Cys Gln His Ser Arg
                 85                  90                  95

Glu Phe Pro Phe Thr Phe Gly Gly Gly Thr Lys Leu Glu Ile Lys
            100                 105                 110

<210> SEQ ID NO 33
<211> LENGTH: 364
<212> TYPE: DNA
<213> ORGANISM: Artificial Sequence
<220> FEATURE:
<223> OTHER INFORMATION: Nucleic acid sequence identified using
      molecular biology techniques.
```

<400> SEQUENCE: 33

```
gaagtgcagc tggtggagtc tgggggaggc ttagtgaaac ctggagggtc cctgaaactc      60
tcctgtgcag cctctggatt cactttcagt aactatgcca tgtcttgggt tcgccagact     120
ccggaaaaga ggctggagtg ggtcgcgacc attagtgatg gtggtggtta cacctactat    180
ttagacaatg gacagggccg attcaccatc tccagagaca atgccaagaa caacctgtac    240
ctgcagatga gccatctgaa gtctgaggac acagccatgt attactgtgc aagagatgtg    300
ggacttacta cgttttggta ccttcgatgt ctggggcaca gggaccacgg tcaccgtctc    360
ctca                                                                 364
```

<210> SEQ ID NO 34
<211> LENGTH: 121
<212> TYPE: PRT
<213> ORGANISM: Artificial Sequence
<220> FEATURE:
<223> OTHER INFORMATION: Amino acid sequence identified using molecular biology techniques.

<400> SEQUENCE: 34

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Gly Tyr Thr Tyr Tyr Leu Asp Asn Gly
    50                  55                  60

Gln Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Val Gly Leu Thr Thr Phe Trp Tyr Phe Asp Val Trp Gly
                100                 105                 110

Thr Gly Thr Thr Val Thr Val Ser Ser
            115                 120
```

<210> SEQ ID NO 35
<211> LENGTH: 333
<212> TYPE: DNA
<213> ORGANISM: Artificial Sequence
<220> FEATURE:
<223> OTHER INFORMATION: Nucliec acid sequence identified using molecular biology techniques.

<400> SEQUENCE: 35

```
gacattgtgc tgacacagtc tcctgtttcc ttagttatat ctctggggca gagggccacc      60
atctcctgca gggccagcaa aagtgtcagt ccatctagct ataatttcat gcactggtac    120
caacagagac caggacagcc gcccaaactc ctcatcacgt atgcttccaa cctagaatct    180
ggggtccctg ccaggttcag tggcagtggg tctgggacag acttcaccct caacatccat    240
cctgtggagg aagaggatgc tgcaacatat tactgtcagc acagtaggga gtttccgttc    300
acgttcggag gggggaccag gctggaaata aaa                                 333
```

<210> SEQ ID NO 36
<211> LENGTH: 111
<212> TYPE: PRT

<213> ORGANISM: Artificial Sequence
<220> FEATURE:
<223> OTHER INFORMATION: Amino acid sequence identified using molecular biology techniques.

<400> SEQUENCE: 36

```
Asp Ile Val Leu Thr Gln Ser Pro Val Ser Leu Val Ile Ser Leu Gly
1               5                   10                  15

Gln Arg Ala Thr Ile Ser Cys Arg Ala Ser Lys Ser Val Ser Pro Ser
            20                  25                  30

Ser Tyr Asn Phe Met His Trp Tyr Gln Gln Arg Pro Gly Gln Pro Pro
        35                  40                  45

Lys Leu Leu Ile Thr Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Phe Thr Phe Gly Gly Gly Thr Arg Leu Glu Ile Lys
            100                 105                 110
```

<210> SEQ ID NO 37
<211> LENGTH: 363
<212> TYPE: DNA
<213> ORGANISM: Artificial Sequence
<220> FEATURE:
<223> OTHER INFORMATION: Amino acid sequence identified using molecular biology techniques.

<400> SEQUENCE: 37

```
gaagtacaac tagtggagtc tggggggaggc ttagtggagc ctggagggtc cctgaaactc      60
tcctgtgcag cctctggatt cactttcagt aactatgcca tgtcttgggt tcgccagact     120
ccggaaaaga ggctggagtg ggtcgcaacc attagtgatg gtggtagttt cacctactat     180
ctagacaatg taaagggccg attcaccatc tccagagaca atgccaagaa caacctgtat     240
ttgcaaatga gccatttgaa gtctgacgac acagccatgt attactgtgc aagagatgtg     300
ggacatacta cgttttggta cttcgatgtc tggggcacag gaccacggt caccgtctcc     360 tca                                                                   363
```

<210> SEQ ID NO 38
<211> LENGTH: 121
<212> TYPE: PRT
<213> ORGANISM: Artificial Sequence
<220> FEATURE:
<223> OTHER INFORMATION: Amino acid sequence identified using molecular biology techniques.

<400> SEQUENCE: 38

```
Glu Val Gln Leu Val Glu Ser Gly Gly Gly Leu Val Glu Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Phe Thr Tyr Tyr Leu Asp Asn Val
    50                  55                  60

Lys Gly Arg Phe Thr Ile Ser Arg Asp Asn Ala Lys Asn Asn Leu Tyr
65                  70                  75                  80
```

```
Leu Gln Met Ser His Leu Lys Ser Asp Asp Thr Ala Met Tyr Tyr Cys
            85                  90                  95

Ala Arg Asp Val Gly His Thr Thr Phe Trp Tyr Phe Val Trp Gly
            100                 105                 110

Thr Gly Thr Thr Val Thr Val Ser Ser
            115                 120

<210> SEQ ID NO 39
<211> LENGTH: 333
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 39
gacattgtgc tgacacagtc tcctgttttc ttagttatat ctctggggca gagggccacc      60
atctcctgca gggccagcaa aagtgtcagt gcatctggct ataatttcat gcactggtac     120
caacagaaac caggacagcc gcccaaagtc ctcatcaagt atgcatccaa cctagaatct     180
ggggtccctg ccaggttcag tggcagtggg tctgggacag acttcaccct caacatccat     240
cctgtggagg aggaggatgc tgtaacatat tactgtcagc acagtaggga gtttccgttc     300
acgttcggag gggggaccaa gctggaaata aaa                                  333

<210> SEQ ID NO 40
<211> LENGTH: 111
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 40

Asp Ile Val Leu Thr Gln Ser Pro Val Phe Leu Val Ile Ser Leu Gly
 1               5                  10                  15

Gln Arg Ala Thr Ile Ser Cys Arg Ala Ser Lys Ser Val Ser Ala Ser
            20                  25                  30

Gly Tyr Asn Phe Met His Trp Tyr Gln Gln Lys Pro Gly Gln Pro Pro
        35                  40                  45

Lys Val Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Val Thr Tyr Tyr Cys Gln His Ser Arg
                85                  90                  95

Glu Phe Pro Phe Thr Phe Gly Gly Gly Thr Lys Leu Glu Ile Lys
            100                 105                 110

<210> SEQ ID NO 41
<211> LENGTH: 1353
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 41
gaaatgcaac tggtggagtc tggggaaggc ttagtgagc ctggagggtc cctgaaactc       60
tcctgtgcag cctctggatt cactttcagt aactatgcca tgtcttgggt tcgccagact     120
```

```
ccggaaaaga gcctggagtg ggtcgcaacc attagtgatg gtggtagttt cacctactat      180
ctagacaatg taaggggccg attcaccatc tccagagaca atgccaagaa caacctgtat      240
ttgcaaatga gccatttgaa gtctgacgac acagccatgt attactgtgc aagagatgtg      300
ggacatacta ccttttggta cttcgatgtc tggggctcag ggacactagt gaccgtgtcc      360
agcgccagca ccaagggccc cagcgtgttc cccctggccc ccagcagcaa gagcaccagc      420
ggcggcacag ccgccctggg ctgcctggtg aaggactact ccccgaacc ggtgaccgtg       480 tcctggaaca gcggagccct gaccagcggc gtgcacacct tccccgccgt gctgcagagc      540
agcggcctgt acagcctgag cagcgtggtg accgtgccca gcagcagcct gggcacccag      600
acctacatct gtaacgtgaa ccacaagccc agcaacacca aggtggacaa gaaggtggag      660
cccaagagct gtgacaagac ccacacctgc cccccctgcc ctgccccga gctgctggga      720 ggccccagcg tgttcctgtt ccccccaag cctaaggaca ccctgatgat cagcagaacc      780
cccgaggtga cctgtgtggt ggtggatgtg agccacgagg accctgaggt gaagttcaac      840
tggtacgtgg acggcgtgga ggtgcacaat gccaagacca gcccaggga ggagcagtac      900 aacagcacct accgggtggt gtccgtgctg accgtgctgc accaggattg gctgaacggc      960
aaggagtaca agtgtaaggt gtccaacaag gccctgcctg cccctatcga gaaaaccatc     1020
agcaaggcca agggccagcc cagagagccc caggtgtaca ccctgccccc tagcagagat     1080
gagctgacca agaaccaggt gtccctgacc tgcctggtga agggcttcta ccccagcgac     1140
atcgccgtgg agtgggagag caacggccag cccgagaaca actacaagac cacccccct      1200 gtgctggaca gcgatggcag cttcttcctg tacagcaagc tgaccgtgga caagagcaga     1260
tggcagcagg gcaacgtgtt cagctgctcc gtgatgcacg aggccctgca caatcactac     1320
acccagaaga gcctgagcct gtcccctggc aag                                   1353
```

<210> SEQ ID NO 42
<211> LENGTH: 451
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 42

```
Glu Met Gln Leu Val Glu Ser Gly Glu Gly Leu Val Glu Pro Gly Gly
  1               5                  10                  15

Ser Leu Lys Leu Ser Cys Ala Ala Ser Gly Phe Thr Phe Ser Asn Tyr
             20                  25                  30

Ala Met Ser Trp Val Arg Gln Thr Pro Glu Lys Ser Leu Glu Trp Val
         35                  40                  45

Ala Thr Ile Ser Asp Gly Gly Ser Phe Thr Tyr Tyr Leu Asp Asn Val
     50                  55                  60

Arg Gly Arg Phe Thr Ile Ser Arg Asp Asn Ala Lys Asn Asn Leu Tyr
 65                  70                  75                  80

Leu Gln Met Ser His Leu Lys Ser Asp Asp Thr Ala Met Tyr Tyr Cys
                 85                  90                  95

Ala Arg Asp Val Gly His Thr Thr Phe Trp Tyr Phe Asp Val Trp Gly
            100                 105                 110

Ser Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 43
<211> LENGTH: 654
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 43
gacattgtgc tgacacagtc tcctgttttc ttagttgtat ctctgggca gagggccacc      60 atctcctgta gggccagcaa aagtgtcagt gcagctggct ataatttcat gcactggtac     120
caacagaaac caggacagcc gcccaaagtc ctcatcaagt atgcatccaa cctagaatct     180
ggggtccctg ccaggttcag tggcagtggg tctgggacag acttcaccct caacatccat     240
```

```
cctgtggagg aggaggatgc tgtaacatat tactgtctgc acagtaggga gtttccgttc    300
acgttcggag gggggaccaa cctggaaata aaacgtacgg tggccgcccc cagcgtgttc    360
atcttccccc ccagcgatga gcagctgaag agcggcaccg ccagcgtggt gtgtctgctg    420
aacaacttct accccgggga ggccaaggtg cagtggaagg tggacaatgc cctgcagagc    480
ggcaacagcc aggagagcgt gaccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca accggggcga gtgc          654
```

<210> SEQ ID NO 44
<211> LENGTH: 218
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 44

```
Asp Ile Val Leu Thr Gln Ser Pro Val Phe Leu Val Val Ser Leu Gly
 1               5                  10                  15

Gln Arg Ala Thr Ile Ser Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45

Lys Val Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Val Thr Tyr Tyr Cys Leu His Ser Arg
                85                  90                  95

Glu Phe Pro Phe Thr Phe Gly Gly Gly Thr Asn Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 45
<211> LENGTH: 1353
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 45

```
gaagtacaac tggtggagtc tgggggaggc ttagtggagc tggagggtc cctgaaactc      60
tcctgtgcag cctctggatt cactttcagt aactatgcca tgtcttgggt tcgccagact    120
ccggaaaaga ggctggagtg ggtcgcaacc attagtgatg gtggtagttt cacctactat    180
ctagacaata taaagggccg attcaccatc tccagagaca atgccaagaa caacctgtat    240
ttgcaaatga gccatttgaa gtctgacgac acagccatgt attactgtgc aagagatgtg    300
ggacatacta cgttttggta cttcgatgtc tggggcacag ggacactagt gaccgtgtcc    360
agcgccagca ccaagggccc cagcgtgttc cccctggccc ccagcagcaa gagcaccagc    420
ggcggcacag ccgccctggg ctgcctggtg aaggactact tccccgaacc ggtgaccgtg    480
tcctggaaca gcggagccct gaccagcggc gtgcacacct tccccgccgt gctgcagagc    540
agcggcctgt acagcctgag cagcgtggtg accgtgccca gcagcagcct gggcacccag    600
acctacatct gtaacgtgaa ccacaagccc agcaacacca aggtggacaa gaaggtggag    660
cccaagagct gtgacaagac ccacacctgc ccccccctgcc ctgccccccga gctgctggga    720
ggccccagcg tgttcctgtt ccccccaag cctaaggaca cctgatgat cagcagaacc     780
cccgaggtga cctgtgtggt ggtggatgtg agccacgagg accctgaggt gaagttcaac    840
tggtacgtgg acggcgtgga ggtgcacaat gccaagacca gcccaggga ggagcagtac     900
aacagcacct accgggtggt gtccgtgctg accgtgctgc accaggattg gctgaacggc    960
aaggagtaca agtgtaaggt gtccaacaag gccctgcctg cccctatcga aaaaccatc    1020
agcaaggcca agggccagcc cagagagccc caggtgtaca ccctgccccc tagcagagat    1080
gagctgacca gaaccaggt gtccctgacc tgcctggtga agggcttcta ccccagcgac    1140
atcgccgtgg agtgggagag caacggccag cccgagaaca actacaagac cacccccccct  1200
gtgctggaca gcgatggcag cttcttcctg tacagcaagc tgaccgtgga caagagcaga    1260
tggcagcagg gcaacgtgtt cagctgctcc gtgatgcacg aggccctgca caatcactac    1320
acccagaaga gcctgagcct gtcccctggc aag                                 1353
```

<210> SEQ ID NO 46
<211> LENGTH: 451
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 46

```
Glu Val Gln Leu Val Glu Ser Gly Gly Gly Leu Val Glu Pro Gly Gly
  1               5                  10                  15

Ser Leu Lys Leu Ser Cys Ala Ala Ser Gly Phe Thr Phe Ser Asn Tyr
             20                  25                  30

Ala Met Ser Trp Val Arg Gln Thr Pro Glu Lys Arg Leu Glu Trp Val
         35                  40                  45

Ala Thr Ile Ser Asp Gly Gly Ser Phe Thr Tyr Tyr Leu Asp Asn Val
     50                  55                  60

Lys Gly Arg Phe Thr Ile Ser Arg Asp Asn Ala Lys Asn Asn Leu Tyr
 65                  70                  75                  80

Leu Gln Met Ser His Leu Lys Ser Asp Asp Thr Ala Met Tyr Tyr Cys
                 85                  90                  95

Ala Arg Asp Val Gly His Thr Thr Phe Trp Tyr Phe Asp Val Trp Gly
            100                 105                 110

Thr Gly Thr Leu Val Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 47
<211> LENGTH: 654
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 47
gacattgtgc tgacacagtc tcctgttttc ttagttatat ctctggggca gagggccacc      60
atctcctgca gggccagcaa aagtgtcagt gcatctggct ataatttcat gcactggtac     120
```

```
caacagaaac caggacagcc gcccaaagtc ctcatcaagt atgcatccaa cctagaatct      180
ggggtccctg ccaggttcag tggcagtggg tctgggacag acttcaccct caacatccat      240
cctgtggagg aggaggatgc tgtaacatat tactgtcagc acagtaggga gtttccgttc      300
acgttcggag gggggaccaa gctggaaata aaacgtacgg tggccgcccc cagcgtgttc      360
atcttccccc ccagcgatga gcagctgaag agcggcaccg ccagcgtggt gtgtctgctg      420
aacaacttct accccgggga ggccaaggtg cagtggaagg tggacaatgc cctgcagagc      480
ggcaacagcc aggagagcgt gaccgagcag gacagcaagg actccaccta cagcctgagc      540
agcaccctga ccctgagcaa ggccgactac gagaagcaca aggtgtacgc ctgtgaggtg      600
acccaccagg gcctgtccag ccccgtgacc aagagcttca ccggggcga gtgc             654
```

<210> SEQ ID NO 48
<211> LENGTH: 218
<212> TYPE: PRT
<213> ORGANISM: Artificial Sequence
<220> FEATURE:
<223> OTHER INFORMATION: Amino acid sequence identified using molecular biology techniques.

<400> SEQUENCE: 48

```
Asp Ile Val Leu Thr Gln Ser Pro Val Phe Leu Val Ile Ser Leu Gly
  1               5                  10                  15

Gln Arg Ala Thr Ile Ser Cys Arg Ala Ser Lys Ser Val Ser Ala Ser
             20                  25                  30

Gly Tyr Asn Phe Met His Trp Tyr Gln Gln Lys Pro Gly Gln Pro Pro
         35                  40                  45

Lys Val Leu Ile Lys Tyr Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Val Thr Tyr Tyr Cys Gln His Ser Arg
                 85                  90                  95

Glu Phe Pro Phe Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 49
<211> LENGTH: 294
<212> TYPE: DNA
<213> ORGANISM: Artificial Sequence
<220> FEATURE:
<223> OTHER INFORMATION: Nucleic acid sequence identified using -continued molecular biology techniques.

<400> SEQUENCE: 49

```
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaagcaag atggaagtga aaatactat      180 gtggactctg tgaagggccg attcaccatc tccagagaca acgccaagaa ctcactgtat     240
ctgcaaatga acagcctgag agccgaggac acggctgtgt attactgtgc gaga           294
```

<210> SEQ ID NO 50
<211> LENGTH: 98
<212> TYPE: PRT
<213> ORGANISM: Artificial Sequence
<220> FEATURE:
<223> OTHER INFORMATION: Amino acid sequence identified using molecular biology techniques.

<400> SEQUENCE: 50

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
         20                  25                  30

Trp Met Ser Trp Val Arg Gln Ala Pro Gly Lys Gly Leu Glu Trp Val
     35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg
```

<210> SEQ ID NO 51
<211> LENGTH: 300
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 51

```
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
```

<210> SEQ ID NO 52
<211> LENGTH: 100
<212> TYPE: PRT
<213> ORGANISM: Artificial Sequence
<220> FEATURE:
<223> OTHER INFORMATION: Amino acid sequence identified using molecular biology techniques.

<400> SEQUENCE: 52

```
Asp Ile Val Met Thr Gln Ser Pro Asp Ser Leu Ala Val Ser Leu Gly
 1               5                  10                  15
```

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr
            100

<210> SEQ ID NO 53
<211> LENGTH: 363
<212> TYPE: DNA
<213> ORGANISM: Homo sapiens

<400> SEQUENCE: 53
gaggtgcagc tggtggaaag cggcggcggc ctggtccagc ccggcgggag cctgagactc      60
tcttgcgccg ctagcggctt caccttcagc aactacgcca tgagctgggt gaggcaggcc     120
cccggcaagg gcctggagtg ggtggccacc atcagcgacg gcggcagctt cacctactat     180
ctggacaacg tgaggggcag gttcaccatc agcagggaca cgccaagaa cagcctgtac     240 ctgcagatga acagcctgag ggccgaggat accgccgtgt actactgcgc cagggacgtc     300
ggccacacca ccttctggta cttcgacgtc tggggcaggg gcacactagt gaccgtgtcc     360
agc                                                                   363

<210> SEQ ID NO 54
<211> LENGTH: 121
<212> TYPE: PRT
<213> ORGANISM: Homo sapiens

<400> SEQUENCE: 54

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Ser Phe Thr Tyr Tyr Leu Asp Asn Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Val Gly His Thr Thr Phe Trp Tyr Phe Asp Val Trp Gly
            100                 105                 110

Arg Gly Thr Leu Val Thr Val Ser Ser
        115                 120

<210> SEQ ID NO 55
<211> LENGTH: 363
<212> TYPE: DNA
<213> ORGANISM: Homo sapiens

<400> SEQUENCE: 55

```
gagatgcagc tggtggaaag cggcggcggc ctggtccagc ccggcgggag cctgagactc    60
tcttgcgccg ctagcggctt caccttcagc aactacgcca tgagctgggt gaggcaggcc   120
cccggcaagg gcctggagtg ggtggccacc atcagcgacg gcggcagctt caccactact   180
ctggacaacg tgaggggcag gttcaccatc agcagggaca cgccaagaa cagcctgtac    240
ctgcagatga acagcctgag ggccgaggat accgccgtgt actactgcgc cagggacgtc   300
ggccacacca ccttctggta cttcgacgtc tggggcaggg gcacactagt gaccgtgtcc   360
agc                                                                  363
```

<210> SEQ ID NO 56
<211> LENGTH: 121
<212> TYPE: PRT
<213> ORGANISM: Homo sapiens

<400> SEQUENCE: 56

```
Glu Met Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ala Thr Ile Ser Asp Gly Gly Ser Phe Thr Tyr Tyr Leu Asp Asn Val
     50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Val Gly His Thr Thr Phe Trp Tyr Phe Asp Val Trp Gly
            100                 105                 110

Arg Gly Thr Leu Val Thr Val Ser Ser
        115                 120
```

<210> SEQ ID NO 57
<211> LENGTH: 363
<212> TYPE: DNA
<213> ORGANISM: Homo sapiens

<400> SEQUENCE: 57

```
gaggtgcagc tggtggaaag cggcggcggc ctggtccagc ccggcgggag cctgagactc    60
tcttgcgccg ctagcggctt caccttcagc aactacgcca tgagctgggt gaggcaggcc   120
cccggcaagg gcctggagtg ggtggccacc atcagcgacg gcggcagctt caccactact   180
ctggacaacg tgaggggcag gttcaccatc agcagggaca cgccaagaa cagcctgtac    240
ctgcagatga acagcctgag ggccgaggat accgccgtgt actactgcgc cagggacgtc   300
ggccacacca ccttctggta cttcgacgtc tggggctccg gcacactagt gaccgtgtcc   360
agc                                                                  363
```

<210> SEQ ID NO 58
<211> LENGTH: 121
<212> TYPE: PRT
<213> ORGANISM: Homo sapiens

<400> SEQUENCE: 58

```
Glu Val Gln Leu Val Glu Ser Gly Gly Gly Leu Val Gln Pro Gly Gly
```

```
                1               5                  10                 15
              Ser Leu Arg Leu Ser Cys Ala Ala Ser Gly Phe Thr Phe Ser Asn Tyr
                             20                  25                 30

Ala Met Ser Trp Val Arg Gln Ala Pro Gly Lys Gly Leu Glu Trp Val
                             35                  40                 45

Ala Thr Ile Ser Asp Gly Gly Ser Phe Thr Tyr Tyr Leu Asp Asn Val
                             50                  55                 60

Arg Gly Arg Phe Thr Ile Ser Arg Asp Asn Ala Lys Asn Ser Leu Tyr
               65                  70                  75                 80

Leu Gln Met Asn Ser Leu Arg Ala Glu Asp Thr Ala Val Tyr Tyr Cys
                             85                  90                 95

Ala Arg Asp Val Gly His Thr Thr Phe Trp Tyr Phe Asp Val Trp Gly
                            100                 105                110

Ser Gly Thr Leu Val Thr Val Ser Ser
                            115                 120

<210> SEQ ID NO 59
<211> LENGTH: 333
<212> TYPE: DNA
<213> ORGANISM: Homo sapiens

<400> SEQUENCE: 59
gacatcgtga tgactcagag ccccgatagc ctggccgtga gcctgggcga aagggccacc      60
atcaactgca gggccagcaa gagcgtgagc gctgccggct acaacttcat gcactggtac     120
cagcagaagc ccggccagcc ccccaagctg ctgatctact acgcctccaa cctggagagc     180
ggcgtgccag acaggttcag cggatctggc agcggcaccg acttcaccct gaccatctca     240
agcctgcagg ccgaggacgt cgccgtgtac tactgcctgc acagcaggga gttccccttc     300
acctttggcg gcggcaccaa ggtggagatc aag                                  333

<210> SEQ ID NO 60
<211> LENGTH: 111
<212> TYPE: PRT
<213> ORGANISM: Homo sapiens

<400> SEQUENCE: 60

Asp Ile Val Met Thr Gln Ser Pro Asp Ser Leu Ala Val Ser Leu Gly
               1               5                  10                 15

Glu Arg Ala Thr Ile Asn Cys Arg Ala Ser Lys Ser Val Ser Ala Ala
                             20                  25                 30

Gly Tyr Asn Phe Met His Trp Tyr Gln Gln Lys Pro Gly Gln Pro Pro
                             35                  40                 45

Lys Leu Leu Ile Tyr Tyr Ala Ser Asn Leu Glu Ser Gly Val Pro Asp
                             50                  55                 60

Arg Phe Ser Gly Ser Gly Ser Gly Thr Asp Phe Thr Leu Thr Ile Ser
               65                  70                  75                 80

Ser Leu Gln Ala Glu Asp Val Ala Val Tyr Tyr Cys Leu His Ser Arg
                             85                  90                 95

Glu Phe Pro Phe Thr Phe Gly Gly Gly Thr Lys Val Glu Ile Lys
                            100                 105                110

<210> SEQ ID NO 61
<211> LENGTH: 333
<212> TYPE: DNA
<213> ORGANISM: Homo sapiens

<400> SEQUENCE: 61
```

```
gacatcgtga tgactcagag ccccgatagc ctggccgtga gcctgggcga aagggccacc    60
atcaactgca gggccagcaa gagcgtgagc gctgccggct acaacttcat gcactggtac   120
cagcagaagc ccggccagcc ccccaaggtg ctgatctact acgcctccaa cctggagagc   180
ggcgtgccag acaggttcag cggatctggc agcggcaccg acttcaccct gaccatctca   240
agcctgcagg ccgaggacgt cgccgtgtac tactgcctgc acagcaggga gttccccttc   300
acctttggcg gcggcaccaa ggtggagatc aag                                333
```

<210> SEQ ID NO 62
<211> LENGTH: 111
<212> TYPE: PRT
<213> ORGANISM: Homo sapiens

<400> SEQUENCE: 62

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45

Lys Val Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Leu His Ser Arg
                85                  90                  95

Glu Phe Pro Phe Thr Phe Gly Gly Gly Thr Lys Val Glu Ile Lys
            100                 105                 110
```

<210> SEQ ID NO 63
<211> LENGTH: 333
<212> TYPE: DNA
<213> ORGANISM: Homo sapiens

<400> SEQUENCE: 63

```
gacatcgtga tgactcagag ccccgatagc ctggccgtga gcctgggcga aagggccacc    60
atcaactgca gggccagcaa gagcgtgagc gctgccggct acaacttcat gcactggtac   120
cagcagaagc ccggccagcc ccccaagctg ctgatctact acgcctccaa cctggagagc   180
ggcgtgccag acaggttcag cggatctggc agcggcaccg acttcaccct gaccatctca   240
agcctgcagg ccgaggacgt cgtggtgtac tactgcctgc acagcaggga gttccccttc   300
acctttggcg gcggcaccaa ggtggagatc aag                                333
```

<210> SEQ ID NO 64
<211> LENGTH: 111
<212> TYPE: PRT
<213> ORGANISM: Homo sapiens

<400> SEQUENCE: 64

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45
```

```
Lys Leu Leu Ile Tyr Tyr Ala Ser Asn Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Val Val Tyr Tyr Cys Leu His Ser Arg
                 85                  90                  95

Glu Phe Pro Phe Thr Phe Gly Gly Gly Thr Lys Val Glu Ile Lys
                100                 105                 110
```

<210> SEQ ID NO 65
<211> LENGTH: 333
<212> TYPE: DNA
<213> ORGANISM: Homo sapiens

<400> SEQUENCE: 65

```
gacatcgtga tgactcagag ccccgatagc ctggccgtga gcctgggcga aagggccacc    60
atcaactgca gggccagcaa gagcgtgagc gctgccggct acaacttcat gcactggtac   120
cagcagaagc ccggccagcc ccccaagctg ctgatctact acgcctccaa cctggagagc   180
ggcgtgccag acaggttcag cggatctggc agcggaccg acttcaccct gaccatctca   240
agcctgcagg ccgaggacgt cgccgtgtac tactgcctgc acagcaggga gttcccctttc   300
accttttggcg gcggcaccaa cgtggagatc aag                                333
```

<210> SEQ ID NO 66
<211> LENGTH: 111
<212> TYPE: PRT
<213> ORGANISM: Homo sapiens

<400> SEQUENCE: 66

```
Asp Ile Val Met Thr Gln Ser Pro Asp Ser Leu Ala Val Ser Leu Gly
  1               5                  10                  15

Glu Arg Ala Thr Ile Asn Cys Arg Ala Ser Lys Ser Val Ser Ala Ala
                 20                  25                  30

Gly Tyr Asn Phe Met His Trp Tyr Gln Gln Lys Pro Gly Gln Pro Pro
             35                  40                  45

Lys Leu Leu Ile Tyr Tyr Ala Ser Asn Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Leu His Ser Arg
                 85                  90                  95

Glu Phe Pro Phe Thr Phe Gly Gly Gly Thr Asn Val Glu Ile Lys
                100                 105                 110
```

<210> SEQ ID NO 67
<211> LENGTH: 333
<212> TYPE: DNA
<213> ORGANISM: Homo sapiens

<400> SEQUENCE: 67

```
gacatcgtga tgactcagag ccccgatagc ctggccgtga gcctgggcga aagggccacc    60
atcaactgca gggccagcaa gagcgtgagc gctgccggct acaacttcat gcactggtac   120
cagcagaagc ccggccagcc ccccaaggtg ctgatctact acgcctccaa cctggagagc   180
ggcgtgccag acaggttcag cggatctggc agcggaccg acttcaccct gaccatctca   240
agcctgcagg ccgaggacgt cgtggtgtac tactgcctgc acagcaggga gttcccctttc   300
```
acctttggcg gcggcaccaa cgtggagatc aag            333

<210> SEQ ID NO 68
<211> LENGTH: 111
<212> TYPE: PRT
<213> ORGANISM: Homo sapiens

<400> SEQUENCE: 68

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45

Lys Val Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Val Val Tyr Tyr Cys Leu His Ser Arg
                85                  90                  95

Glu Phe Pro Phe Thr Phe Gly Gly Gly Thr Asn Val Glu Ile Lys
            100                 105                 110

<210> SEQ ID NO 69
<211> LENGTH: 1353
<212> TYPE: DNA
<213> ORGANISM: Homo sapiens

<400> SEQUENCE: 69
gaggtgcagc tggtggaaag cggcggcggc ctggtccagc ccggcgggag cctgagactc      60
tcttgcgccg ctagcggctt caccttcagc aactacgcca tgagctgggt gaggcaggcc     120
cccggcaagg gcctggagtg ggtggccacc atcagcgacg gcggcagctt cacctactat     180
ctggacaacg tgaggggcag gttcaccatc agcagggaca cgccaagaa cagcctgtac      240 ctgcagatga acagcctgag ggccgaggat accgccgtgt actactgcgc cagggacgtc     300
ggccacacca ccttctggta cttcgacgtc tggggcaggg gcacactagt gaccgtgtcc     360
agcgccagca ccaagggccc cagcgtgttc cccctggccc ccagcagcaa gagcaccagc     420
ggcggcacag ccgccctggg ctgcctggtg aaggactact ccccgaacc ggtgaccgtg      480 tcctggaaca gcggagccct gaccagcggc gtgcacacct ccccgccgt gctgcagagc      540 agcggcctgt acagcctgag cagcgtggtg accgtgccca gcagcagcct gggcacccag     600
acctacatct gtaacgtgaa ccacaagccc agcaacacca aggtggacaa gaaggtggag     660
cccaagagct gtgacaagac ccacacctgc cccccctgcc ctgcccccga gctgctggga     720
ggccccagcg tgttcctgtt cccccccaag cctaaggaca ccctgatgat cagcagaacc     780
cccgaggtga cctgtgtggt ggtggatgtg agccacgagg accctgaggt gaagttcaac     840
tggtacgtgg acggcgtgga ggtgcacaat gccaagacca gcccaggga ggagcagtac      900 aacagcacct accgggtggt gtccgtgctg accgtgctgc accaggattg gctgaacggc     960
aaggagtaca agtgtaaggt gtccaacaag gccctgcctg cccctatcga gaaaccatc     1020 agcaaggcca agggccagcc cagagagccc caggtgtaca ccctgccccc tagcagagat    1080
gagctgacca gaaccaggt gtccctgacc tgcctggtga agggcttcta ccccagcgac    1140
atcgccgtgg agtgggagag caacggccag ccgagaaca actacaagac cacccccct    1200

```
gtgctggaca gcgatggcag cttcttcctg tacagcaagc tgaccgtgga caagagcaga   1260
tggcagcagg gcaacgtgtt cagctgctcc gtgatgcacg aggccctgca caatcactac   1320
acccagaaga gcctgagcct gtcccctggc aag                                1353
```

<210> SEQ ID NO 70
<211> LENGTH: 451
<212> TYPE: PRT
<213> ORGANISM: Homo sapiens

<400> SEQUENCE: 70

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
         35                  40                  45

Ala Thr Ile Ser Asp Gly Gly Ser Phe Thr Tyr Tyr Leu Asp Asn Val
     50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Val Gly His Thr Thr Phe Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 71
<211> LENGTH: 654
<212> TYPE: DNA
<213> ORGANISM: Homo sapiens

<400> SEQUENCE: 71
gacatcgtga tgactcagag ccccgatagc ctggccgtga gcctgggcga aaggggccacc      60 atcaactgca gggccagcaa gagcgtgagc gctgccggct acaacttcat gcactggtac     120
cagcagaagc ccggccagcc ccccaaggtg ctgatctact acgcctccaa cctggagagc     180
ggcgtgccag acaggttcag cggatctggc agcggcaccg acttcaccct gaccatctca     240
agcctgcagg ccgaggacgt cgccgtgtac tactgcctgc acagcaggga gttccccttc     300
acctttggcg gcggcaccaa ggtggagatc aagcgtacgg tggccgcccc cagcgtgttc     360
atcttccccc ccagcgatga gcagctgaag agcggcaccg ccagcgtggt gtgtctgctg     420
aacaacttct accccgggga ggccaaggtg cagtggaagg tggacaatgc cctgcagagc     480
ggcaacagcc aggagagcgt gaccgagcag gacagcaagg actccaccta cagcctgagc     540
agcaccctga ccctgagcaa ggccgactac gagaagcaca aggtgtacgc ctgtgaggtg     600
acccaccagg gcctgtccag ccccgtgacc aagagcttca accggggcga gtgc            654

<210> SEQ ID NO 72
<211> LENGTH: 218
<212> TYPE: PRT
<213> ORGANISM: Homo sapiens

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ala
            20                  25                  30

Gly Tyr Asn Phe Met His Trp Tyr Gln Gln Lys Pro Gly Gln Pro Pro
        35                  40                  45

Lys Val Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Leu His Ser Arg
                85                  90                  95

Glu Phe Pro Phe Thr Phe Gly Gly Gly Thr Lys Val Glu Ile Lys Arg
```

```
                       100                 105                 110
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 73
<211> LENGTH: 360
<212> TYPE: DNA
<213> ORGANISM: Homo sapiens

<400> SEQUENCE: 73
gaggtgcagc tggtggaaag cggcggcggc ctggtccagc ccggcgggag cctgagactc       60
tcttgcgccg ctagcggctt caccttcagc tacgccatga gctgggtgag gcaggccccc      120
ggcaagggcc tggagtgggt ggccaccatc agcgacggcg gcagcttcac ctactatctg      180
gacaacgtga ggggcaggtt caccatcagc agggacaacg ccaagaacag cctgtacctg      240
cagatgaaca gcctgagggc cgaggatacc gccgtgtact actgcgccag ggacgtcggc      300
cacaccacct tctggtactt cgacgtctgg ggcaggggca cactagtgac cgtgtccagc      360

<210> SEQ ID NO 74
<211> LENGTH: 121
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Ser Phe Thr Tyr Tyr Leu Asp Asn Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly His Thr Thr Phe Trp Tyr Phe Asp Val Trp Gly
            100                 105                 110

Arg Gly Thr Leu Val Thr Val Ser Ser
        115                 120

<210> SEQ ID NO 75
<211> LENGTH: 1353
<212> TYPE: DNA
```

-continued

<213> ORGANISM: Homo sapiens

<400> SEQUENCE: 75

```
gaggtgcagc tggtggaaag cggcggcggc ctggtccagc ccggcgggag cctgagactc      60
tcttgcgccg ctagcggctt caccttcagc agctacgcca tgagctgggt gaggcaggcc     120
cccggcaagg gcctggagtg ggtggccacc atcagcgacg gcggcagctt cacctactat     180
ctggacaacg tgaggggcag gttcaccatc agcagggaca cgccaagaa cagcctgtac      240
ctgcagatga acagcctgag ggccgaggat accgccgtgt actactgcgc cagggacgtc     300
ggccacacca ccttctggta cttcgacgtc tggggcaggg gcacactagt gaccgtgtcc     360
agcgccagca ccaagggccc cagcgtgttc cccctggccc ccagcagcaa gagcaccagc     420
ggcggcacag ccgccctggg ctgcctggtg aaggactact tccccgaacc ggtgaccgtg     480
tcctggaaca gcggagccct gaccagcggc gtgcacacct tccccgccgt gctgcagagc     540
agcggcctgt acagcctgag cagcgtggtg accgtgccca gcagcagcct gggcacccag     600
acctacatct gtaacgtgaa ccacaagccc agcaacacca aggtggacaa gaaggtggag     660
cccaagagct gtgacaagac ccacacctgc cccccctgcc ctgcccccga gctgctggga     720
ggccccagcg tgttcctgtt cccccccaag cctaaggaca ccctgatgat cagcagaacc     780
cccgaggtga cctgtgtggt ggtggatgtg agccacgagg accctgaggt gaagttcaac     840
tggtacgtgg acggcgtgga ggtgcacaat gccaagacca gcccaggga ggagcagtac     900
aacagcacct accgggtggt gtccgtgctg accgtgctgc accaggattg gctgaacggc     960
aaggagtaca agtgtaaggt gtccaacaag gccctgcctg cccctatcga gaaaaccatc    1020
agcaaggcca agggccagcc cagagagccc caggtgtaca ccctgccccc tagcagagat    1080
gagctgacca gaaccaggt gtccctgacc tgcctggtga agggcttcta ccccagcgac    1140
atcgccgtgg agtgggagag caacggccag cccgagaaca actacaagac cacccccct     1200
gtgctggaca gcgatggcag cttcttcctg tacagcaagc tgaccgtgga caagagcaga    1260
tggcagcagg gcaacgtgtt cagctgctcc gtgatgcacg aggccctgca caatcactac    1320
acccagaaga gcctgagcct gtcccctggc aag                                 1353
```

<210> SEQ ID NO 76
<211> LENGTH: 451
<212> TYPE: PRT
<213> ORGANISM: Homo sapiens

<400> SEQUENCE: 76

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Asp Gly Gly Ser Phe Thr Tyr Tyr Leu Asp Asn Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly His Thr Thr Phe Trp Tyr Phe Asp Val Trp Gly
            100                 105                 110
```

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 77
<211> LENGTH: 5
<212> TYPE: PRT
<213> ORGANISM: Homo sapiens

<400> SEQUENCE: 77

Ser Tyr Ala Met Ser
1               5

<210> SEQ ID NO 78

```
<211> LENGTH: 7
<212> TYPE: PRT
<213> ORGANISM: Homo sapiens

<400> SEQUENCE: 78

Lys Ala Ser Ser Leu Glu Ser
1               5

<210> SEQ ID NO 79
<211> LENGTH: 450
<212> TYPE: PRT
<213> ORGANISM: Homo sapiens

<400> SEQUENCE: 79

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Pro Asn Ser Asn Phe Tyr Trp Tyr Phe Asp Val Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

-continued

```
Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 80
<211> LENGTH: 213
<212> TYPE: PRT
<213> ORGANISM: Homo sapiens

<400> SEQUENCE: 80

Glu Ile Val Leu Thr Gln Ser Pro Ala Thr Leu Ser Leu Ser Pro Gly
1               5                   10                  15

Glu Arg Ala Thr Leu Ser Cys Ser Gly Ser Ser Ser Val Ser Tyr Met
            20                  25                  30

Tyr Trp Tyr Gln Gln Lys Pro Gly Gln Ala Pro Arg Leu Leu Ile Glu
        35                  40                  45

Asp Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Asn Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 81
<211> LENGTH: 120
<212> TYPE: PRT
```

<213> ORGANISM: Homo sapiens

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Pro Asn Ser Asn Phe Tyr Trp Tyr Phe Asp Val Trp Gly Arg
            100                 105                 110

Gly Thr Leu Val Thr Val Ser Ser
        115                 120

<210> SEQ ID NO 82
<211> LENGTH: 105
<212> TYPE: PRT
<213> ORGANISM: Homo sapiens

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Ser Gly Ser Ser Ser Val Ser Tyr Met
            20                  25                  30

Tyr Trp Tyr Gln Gln Lys Pro Gly Gln Ala Pro Arg Leu Leu Ile Glu
        35                  40                  45

Asp Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Asn Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Leu Glu Ile
            100                 105

<210> SEQ ID NO 83
<211> LENGTH: 759
<212> TYPE: DNA
<213> ORGANISM: Homo sapiens

<400> SEQUENCE: 83
atgggggtac tgctcacaca gaggacgctg ctcagtctgg tccttgcact cctgtttcca      60
agcatggcga gcatggcggc tataggcagc tgctcgaaag agtaccgcgt gctccttggc     120
cagctccaga agcagacaga tctcatgcag gacaccagca gactcctgga cccctatata     180
cgtatccaag gcctggatgt tcctaaactg agagagcact gcaggagcg cccggggcc       240 ttccccagtg aggagaccct gagggggctg ggcaggcggg gcttcctgca gaccctcaat     300
gccacactgg gctgcgtcct gcacagactg gccgacttag agcagcgcct ccccaaggcc     360
caggatttgg agaggtctgg gctgaacatc gaggacttgg agaagctgca gatggcgagg     420

```
ccgaacatcc tcgggctcag gaacaacatc tactgcatgg cccagctgct ggacaactca      480
gacacggctg agcccacgaa ggctggccgg ggggcctctc agccgcccac ccccacccct      540
gcctcggatg cttttcagcg caagctggag ggctgcaggt tcctgcatgg ctaccatcgc      600
ttcatgcact cagtggggcg ggtcttcagc aagtgggggg agagcccgaa ccggagccgg      660
agacacagcc cccaccaggc cctgaggaag ggggtgcgca ggaccagacc ctccaggaaa      720
ggcaagagac tcatgaccag gggacagctg ccccggtag                            759
```

<210> SEQ ID NO 84
<211> LENGTH: 252
<212> TYPE: PRT
<213> ORGANISM: Homo sapiens

<400> SEQUENCE: 84

```
Met Gly Val Leu Leu Thr Gln Arg Thr Leu Leu Ser Leu Val Leu Ala
 1               5                  10                  15

Leu Leu Phe Pro Ser Met Ala Ser Met Ala Ala Ile Gly Ser Cys Ser
             20                  25                  30

Lys Glu Tyr Arg Val Leu Leu Gly Gln Leu Gln Lys Gln Thr Asp Leu
         35                  40                  45

Met Gln Asp Thr Ser Arg Leu Leu Asp Pro Tyr Ile Arg Ile Gln Gly
     50                  55                  60

Leu Asp Val Pro Lys Leu Arg Glu His Cys Arg Glu Arg Pro Gly Ala
 65                  70                  75                  80

Phe Pro Ser Glu Glu Thr Leu Arg Gly Leu Gly Arg Arg Gly Phe Leu
                 85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Thr Arg Pro Ser Arg Lys
225                 230                 235                 240

Gly Lys Arg Leu Met Thr Arg Gly Gln Leu Pro Arg
                245                 250
```

ANTIGEN BINDING PROTEINS TO ONCOSTATIN M (OSM)

This application is a 371 of International Application No. PCT/EP2011/070604, filed 21 Nov. 2011, which claims the benefit of U.S. Provisional Application No. 61/416,495, filed 23 Nov. 2010, both of which are herein incorporated by reference in their entireties.

FIELD OF THE INVENTION

The present invention relates to immunoglobulins that specifically bind Oncostatin M (OSM) and in particular human OSM (hOSM).

The present invention also concerns methods of treating diseases or disorders with said immunoglobulins, pharmaceutical compositions comprising said immunoglobulins and methods of manufacture. Other embodiments of the present invention will be apparent from the description below.

BACKGROUND OF THE INVENTION

Oncostatin M is a 28 KDa glycoprotein that belongs to the interleukin 6 (IL-6) family of cytokines which includes IL-6, Leukaemia Inhibitory Factor (LIF), ciliary neurotrophic factor (CNTF), cardiotropin-1 (CT-1) and cardiotrophin-1 like cytokine (See Kishimoto T et al (1995) Blood 86: 1243-1254), which share the gp130 transmembrane signalling receptor (See Taga T and Kishimoto T (1997) Annu. Rev. Immunol. 15: 797-819). OSM was originally discovered by its ability to inhibit the growth of the melanoma cell line A375 (See Malik N (1989) et al Mol Cell Biol 9: 2847-2853). Subsequently, more effects were discovered and it was found to be a multifunctional mediator like other members of the IL-6 family. OSM is produced in a variety of cell types including macrophages, activated T cells (See Zarling J M (1986) PNAS (USA) 83: 9739-9743), polymorphonuclear neutrophils (See Grenier A et al (1999) Blood 93:1413-1421), eosinophils (See Tamura S et al (2002) Dev. Dyn. 225: 327-31), dendritic cells (See Suda T et al (2002) Cytokine 17:335-340). It is also expressed in pancreas, kidney, testes, spleen stomach and brain (See Znoyko I et al (2005) Anat Rec A Discov Mol Cell Evol Biol 283: 182-186), and bone marrow (See Psenak O et al (2003) Acta Haematol 109: 68-75) Its principle biological effects include activation of endothelium (See Brown T J et al (1993) Blood 82: 33-7), activation of the acute phase response (See Benigni F et al (1996) Blood 87: 1851-1854), induction of cellular proliferation or differentiation, modulation of inflammatory mediator release and haematopoesis (See Tanaka M et al (2003) 102: 3154-3162), re-modelling of bone (See de Hooge ASK (2002) Am J Pathol 160: 1733-1743) and, promotion of angiogenesis (See Vasse M et al (1999) Arterioscler Thromb Vasc Biol 19:1835-1842) and wound healing.

Receptors for OSM (OSM receptor β, "OSMRβ") are expressed on a wide range of cells including epithelial cells, chondrocytes, fibroblasts (See Langdon C et al (2003) J Immunol 170: 548-555), neuronal smooth muscle, lymph node, bone, heart, small intestine, lung and kidney (See Tamura S et al (2002) Mech Dev 115: 127-131) and endothelial cells. Several lines of evidence suggest that endothelial cells are a primary target for OSM. These cells express 10 to 20 fold higher numbers of both high and low affinity receptors and exhibit profound and prolonged alterations in phenotype following stimulation with OSM (See Modur V et al (1997) J Clin Invest 100: 158-168). In addition, OSM is a major autocrine growth factor for Kaposi's sarcoma cells, which are thought to be of endothelial origin (See Murakami-Mori K et al (1995) J Clin Invest 96:1319-1327).

In common with other IL-6 family cytokines, OSM binds to the transmembrane signal transducing glycoprotein gp130. A key feature of the gp130 cytokines is the formation of oligomeric receptor complexes that comprise gp130 and one or more co-receptors depending on the ligand (Reviewed in Heinrich P C et al (2003) Biochem J. 374: 1-20). As a result, these cytokines can mediate both the shared and unique biological activities in vitro and in vivo depending on the composition of the receptor complex formed. Human OSM (hOSM) differs from the other IL-6 cytokines in that it can form complexes with gp130 and either one of the two co-receptors, LIFR or the oncostatin receptor (OSMR). FIG. 27 illustrates the interaction between hOSM and gp130, LIFR and OSMR.

The crystal structure of hOSM has been solved and shown to comprise a four α, helical bundle with two potential glycosylation sites. Two separate ligand binding sites have been identified by site-directed mutagenesis on the hOSM molecule (See Deller M C et al (2000) Structural Fold Des. 8:863-874). The first, called Site II (sometimes "site 2") interacts with gp130 and the second site, called Site III (sometimes "site 3"), at the opposite end of the molecule interacts with either LIFR or OSMR. Mutagenesis experiments have shown that the binding sites for LIFR and OSMR are almost identical but that a single amino acid mutation can discriminate between the two.

There is increasing evidence to support the hypothesis that modulating OSM-gp130 interaction may be of benefit in the treatment of RA and other diseases and disorders, particularly chronic inflammatory diseases and disorders such as osteoarthritis, idiopathic pulmonary fibrosis, pain, inflammatory lung disease, cardiovascular disease and psoriasis.

OSM is found in the SF of human RA patients (See Hui W et al (1997) 56: 184-7). These levels correlate with; the number of neutrophils in SF, levels of TNF alpha (sometimes "TNF") in SF, and markers of cartilage destruction (Manicourt D H et al (2000) Arthritis Rheum 43: 281-288). Furthermore, the synovial tissue from RA patients secretes OSM spontaneously ex vivo (See Okamoto H et al (1997) Arthritis and Rheumatism 40: 1096-1105). It has also been demonstrated that OSM is present in synovial macrophages (Cawston T E et al (1998) Arthritis Rheum 41: 1760-1771) and as discussed earlier, OSM receptors and gp130 are expressed on endothelial cells, synovial fibroblasts, chonodrocytes and osteoblasts. Adenoviral expression of murine OSM (mOSM) in the joints of normal mice results in a severe inflammatory and erosive arthritis (See Langdon C et al (2000) Am J Pathol 157: 1187-1196). Similarly aggressive disease is seen in knockout mice lacking TNF, IL-1, IL-6 and iNOS following adenoviral mOSM delivery (See de Hooge A S K et al (2003) Arthritis and Rheumatism 48:1750-1761), demonstrating that OSM can mediate all embodiments of arthritis pathology. Mouse OSM expression using an adenovirally expressed mOSM vector causes damage to the growth plate typical of Juvenile Idiopathic Arthritis (See de Hooge A S K et al (2003) Arthritis and Rheumatism 48:1750-1761). In an experimental model of collagen induced arthritis, an anti-OSM antibody administered therapeutically to mice prevented all further progression of disease. Similar results were seen when anti-OSM was administered prophylatically to mice with pristane induced arthritis, a relapsing/remitting model reminiscient of the human disease (See Plater-Zyberk C et al (2001) Arthritis and Rheumatism 44:

Osteoarthritis is a condition that affects the joints. There are three characteristics of osteoarthritis. It causes damage to cartilage—the strong, smooth surface that lines the bones and allows joints to move easily and without friction. It results in bony growths developing around the edge of the joints, and it causes mild inflammation of the tissues around the joints (synovitis). OSM has been demonstrated to play an important role in cartilage breakdown, inflammation and bone turnover and therefore blockade of this cytokine could play a role in the key aspects of disease pathogenesis. OSM acts synergistically with either IL-1 or TNF to induce collagenolysis in human nasal cartilage, involving loss of proteoglycans (PG) and collagen, the latter correlating with induction of MMP-1 and MMP-13. OSM with IL-1 will also induce PG loss from human articular cartilage, but the increase in collagen loss was not significant. (Morgan et al 2006) A number of studies using adenoviral vectors to increase joint cytokine concentrations have shown that OSM over-expression will induce inflammation, pannus formation, cartilage destruction and bone erosion. (Langdon et al 2000). Overall the literature suggests that OSM, particularly when combined with other cytokines, induces proteases that are involved in proteoglycan and collagen breakdown resulting in cartilage degradation and bone erosion.

Information from the literature suggests that OSM molecule may have some involvement in the inflammatory process associated with psoriasis. Work by Boifati et al (1998) has shown that spontaneous release of OSM is increased in organ cultures of psoriatic lesions, compared with non-lesional psoriatic skin and normal skin. (Kunsfeild et al 2004) Keratinocytes express the receptor for this molecule and in response to the ligand this causes keratinocyte migration and increases the thickness of reconstituted epidermis. Microarray analysis comparing the gene modulating effects of OSM with 33 different cytokines indicate that it is a potent keratinocyte activator and can act in synergy with pro-inflammatory cytokines in the induction of molecules such as S100A7 and β-defensin 2 expression, characteristic of psoriatic skin. (Gaze) et al 2006)

A role for OSM in inflammatory lung disease such as asthma and pulmonary fibrosis is also suggested from the literature. These diseases are characterized by an increased deposition of extracellular matrix (ECM), concomitant with proliferation and activation of sub-epithelial fibroblasts. OSM has been detected in the bronchoaveolar lavage fluid of patients during acute lung injury, particularly in cases of pneumonia (Grenier et al 2001).

OSM has been detected in the brains of MS patients, where it localises to microglia, astrocytes and infiltrating leukocytes (Ruprecht et al 2001). In addition, PBMCs isolated from MS patients spontaneously release more cytokines, including OSM, than cells from healthy controls and MS patients show a trend towards increased sera [OSM] (Ensoli et al 2002).

In addition to promoting inflammation in the brain, OSM may directly contribute to neurodegeneration, a feature of Alzhiemer's disease, MS and of a subset of HIV patients. Monocyte supernatants from HIV patients' cause profound neuroblast growth inhibition and neuronal cell death. These effects were mediated by Oncostatin M in the culture supernatant (Ensoli et al 1999). Since many HIV patients suffer from brain atrophy caused by neuronal cell loss, OSM may be one mediator of this pathology.

Work by Tamura et al suggests that OSM may be involved in the development and maintenance of neuropathic pain (2003). Their studies revealed a subset of nociceptive sensory neurons that express the OSMβ receptor. All the OSMβR+ve neurons also expressed VR1 and P2X3 receptors, which have been shown to be crucial for development of both neuropathic and inflammatory pain (Jarvis et al 2002, Walker et al 2003).

It has also been shown that the OSM –/– mouse showed reduced noxious responses to chemical, thermal, visceral and mechanical pain (Morikawa et al 2004). Interestingly, these animals have a deficit in VR1+, P2X3+ small sized neurons, but otherwise the animals appear normal.

A role supporting OSM in modulating the biology of cancer cells has also been suggested from the literature. OSM has been reported as having both growth stimulating and growth inhibitory properties in studies using tumour cell lines (Grant and Begly 1999). It is a potent mitogen for Kaposi's sarcoma derived cells (Miles et al 1992) and for myeloma cell lines (Zhang et al 1994). OSM decreases growth rates and increases differentiation in a number of tumour cell lines, including breast (Douglas et al 1998), and lung (McKormick et al 2000). However, whilst OSM may inhibit growth, at least in some breast carcinoma cell lines, it increases cell detachment and enhances the metatastic potential (Holzer et al 2004, Jorcyk et al 2006). OSM also upregulates expression and activation state of the hyaluronan receptor CD44, in some tumour cell lines (Cichy et al 2000), which is associated with tumour growth and metastasis (Yu et al 1997). In addition, the angiogenic properties of OSM and its ability to induce other angiogenic factors in some tumour cells (Repovic et al 2003), suggest that it could contribute to tumour angiogenesis in those tumours expressing OSM. The scientific literature suggests the OSM involvement in tumour biology but indicate the complexity. It is possible that OSM neutralisation could beneficial for treatment of some tumours. On the other hand, like TNF and IL-6 neutralisation, it carries some potential risk in others.

Evidence from literature suggests a potential role for OSM in cardiovascular disease. OSM is found in tissue macrophages in atherosclerotic lesions (Modur et al 1997) and as an angiogenic factor (Vasse et al 1999) may promote the neovascularisation characteristic of atherosclerotic plaques thought to contribute to vessel wall fragility. However, OSM also induces expression other angiogenic factors in endothelial cells; VEGF (Wijelah et al 1997) and bFGF (Bernard et al 1999). Interestingly, human endothelial cells have about 10-20 fold greater OSM receptor density than other cells (Brown et al 1991).

It is therefore an object of the present invention to provide a therapeutic approach to the treatment of RA and other diseases and disorders, particularly chronic inflammatory diseases and disorders such as osteoarthritis, idiopathic pulmonary fibrosis, cancer, asthma, pain, cardiovascular and psoriasis. In particular it is an object of the present invention to provide immunoglobulins, especially antibodies that specifically bind OSM (e.g. hOSM, particularly Site II thereof) and modulate (i.e. inhibit or block) the interaction between OSM and gp130 in the treatment of diseases and disorders responsive to modulation of that interaction.

In WO99/48523, we disclose the use of OSM antagonists in the treatment of inflammatory diseases and disorders. This disclosure used an anti-mouse OSM antibody in a murine model of arthritis.

All patent and literature references disclosed within the present specification are expressly and entirely incorporated herein by reference.

BRIEF DESCRIPTION OF FIGURES

FIG. 1: Human gp130 ELISA—Inhibition of Human OSM binding to human gp130 by 10G8, 9G2, 3E3 & 2B7. A non-competitive anti-OSM mouse antibody (15E10) was added for comparison purposes. A tool antibody was used as a negative control. Data shown are representative of one of four assay repeats.

FIG. 2: KB Cell Assay—Inhibition of Human OSM by 10G8, 9G2, 3E3 & 2B7. A non-competitive anti-OSM mouse antibody (15E10) was added for comparison purposes. A tool antibody was used as a negative control. Data shown are representative of one of three assay repeats.

FIG. 3: KB Cell Assay—Inhibition of Human OSM in the Presence of 25% Human AB Serum by 10G8, 9G2, 3E3 & 2B7. A non-competitive anti-OSM mouse antibody (15E10) was added for comparison purposes. A tool antibody was used as a negative control. Data shown are representative of one of two assay repeats.

FIG. 4: Endogenous OSM Human gp130 Assay—Inhibition of Endogenous Human OSM Binding to Human gp130 by 10G8, 9G2, 3E3 & 2B7 antibodies. A non-competitive anti-OSM mouse antibody (1I0) was added for comparison purposes. A tool antibody was used as a negative control. Data shown are representative of one of two donors.

FIG. 5: KB Cell Assay—Lack of Inhibition of Human LIF by 10G8, 9G2, 3E3 & 2B7. A non-competitive anti-OSM mouse antibody (15E10) was added for comparison purposes. A commercial anti-Human LIF mAb (R&D Systems, MAB250) was used as a positive control. A tool antibody was used as a negative control.

FIG. 6: KB Cell Assay—Inhibition of Marmoset OSM by 10G8, 9G2, 3E3 & 2B7. A non-competitive anti-OSM mouse antibody (15E10) was added for comparison purposes. A tool antibody was used as a negative control. Data shown are representative of one of two assay repeats.

FIG. 7: Comparison of the VH sequences of the 2B7, 3E3, 9G2 and 10G8 hybridomas. Small boxed residues represent a difference from the majority. Large boxes across sequences represent the CDR'S.

FIG. 8: Comparison of the VL sequences of the 2B7, 3E3, 9G2 and 10G8 hybridomas. Small boxed residues represent a difference from the majority. Large boxes across sequences represent the CDR'S.

FIG. 9: Sequence Analysis of the Variable Light Chains—of 10G8, 9G2, 3E3 and 2B7 compared with a non-competitive anti-OSM mouse parental antibody 15E10.

FIG. 10: Sequence Analysis of the Variable Heavy Chains—of 10G8, 9G2, 3E3 and 2B7 compared with a non-competitive anti-OSM mouse parental antibody 15E10.

FIG. 11: Direct Human OSM Binding ELISA—Comparison of human OSM binding of 10G8 and 9G2 chimaeras with 15E10 chimaera (15E10c).

FIG. 12: Human gp130 ELISA—Inhibition of Human OSM binding to human gp130 by 10G8, 10G8 Chimaera, 9G2 & 9G2 Chimaera. A non-competitive anti-OSM mouse antibody (15E10) was added for comparison purposes. A tool antibody was used as a negative control. Data shown are representative of one of three assay repeats.

FIG. 13: KB Cell Assay—Inhibition of Human OSM by 10G8, 10G8 Chimaera, 9G2 & 9G2 Chimaera. A non-competitive anti-OSM mouse antibody (15E10) was added for comparison purposes. A tool antibody was used as a negative control. Data shown are representative of one of three assay repeats.

FIG. 14: KB Cell Assay—Inhibition of Human OSM in the Presence of 25% Human AB Serum by 10G8, 10G8 Chimaera, 9G2 & 9G2 Chimaera. A non-competitive anti-OSM mouse antibody (15E10) was added for comparison purposes. A tool antibody was used as a negative control. Data shown are representative of one of three assay repeats.

FIG. 15: Endogenous OSM Human gp130 Assay—Inhibition of Endogenous Human OSM Binding to Human gp130 by 10G8, 10G8 Chimaera, 9G2 & 9G2 Chimaera antibodies. A non-competitive anti-OSM mouse antibody (15E10) was added for comparison purposes. A tool antibody was used as a negative control. Data shown are representative of one of two donors.

FIG. 16: Human LIF KB Cell Assay—No Inhibition of Human LIF by 10G8, 10G8 Chimaera, 9G2 & 9G2 Chimaera. A non-competitive anti-OSM mouse antibody (15E10) was added for comparison purposes. An anti-Human LIF antibody (MAB250, R&D Systems) was used as a positive control. A tool antibody was used as a negative control. Data shown are representative of one of three assay repeats.

FIG. 17: KB Cell Assay—Inhibition of Human OSM by Humanised 10G8 L1 and L4 Variants. 15E10h was added for comparison. Data shown are representative of one of three assay repeats.

FIG. 18: Human gp130 ELISA—Inhibition of Human OSM binding to human gp130 by Humanised 10G8 H0L1, H1L1 and H2L1 variants. 15E10h was added for comparison. A tool antibody was used as a negative control. Data shown are representative of one of two assay repeats.

FIG. 19: Human OSM-10G8 mAb Binding Complex—Binding of human OSM with 10G8 mAb light chain and heavy chain. The OSM receptor binding sites are shown (Site II and Site III). The amino acid residues important in the receptor binding regions are listed for each site.

FIG. 20: KB Cell Assay—Inhibition of Human OSM by Humanised 10G8 H0L1 CDRH1 and CDRL2 variant antibodies. 15E10h was added for comparison. A tool antibody was used as a negative control. Data shown are representative of one of three assay repeats.

FIG. 21: Human gp130 ELISA—Inhibition of Human OSM binding to human gp130 by the 10G8 mouse parental, 10G8 Chimera, the Humanised 10G8 H0L1 parent (H0L1) and H0(huCDRH1)L1. 15E10h was added for comparison. A tool antibody was used as a negative control. Data shown are representative of one of three assay repeats.

FIG. 22: KB Cell Assay—Inhibition of Human OSM by the 10G8 mouse parental, 10G8 Chimera, the Humanised 10G8 H0L1 parent (H0L1) and H0(huCDRH1)L1. 15E10h was added for comparison. Data shown are representative of one of three assay repeats FIG. 23: KB Cell Assay—Inhibition of Human OSM in the Presence of 25% Human AB Serum by the 10G8 mouse parental, 10G8 Chimera, the Humanised 10G8 H0L1 parent (H0L1) and H0(H1)L1. 15E10h was added for comparison. A tool antibody was used as a negative control. Data shown are representative of one of two assay repeats.

FIG. 24: Endogenous OSM Human gp130 Assay—Inhibition of Endogenous Human OSM Binding to Human gp130 by the 10G8 mouse parental, 10G8 Chimera, the Humanised 10G8 H0L1 parent (H0L1) and H0(huCDRH1)L1. 15E10h was added for comparison. A tool antibody was used as a negative control. Data shown are representative of one of four donors.

FIG. 25: Human LIF KB Cell Assay—No Inhibition of Human LIF by the 10G8 mouse parental, 10G8 Chimaera, the Humanised 10G8 H0L1 parent (H0L1), H0(huCDRH1)L1. 15E10h was added for comparison. An anti-Human LIF antibody (MAB250, R&D Systems) was used as a positive control. A tool antibody was used as a negative control. Data shown are representative of one of three assay repeats.

FIG. 26: Human Primary Hepatocyte Assay—Inhibition of Serum Amyloid A (SAA) release by H0(huCDRH1)L1 from human hepatocytes stimulated with (A) 3 ng/ml and (B) 10 ng/ml human OSM. Humanised 15E10 was added for comparison purposes. Data shown are representative of one of three hepatocyte donors.

Figure 34:
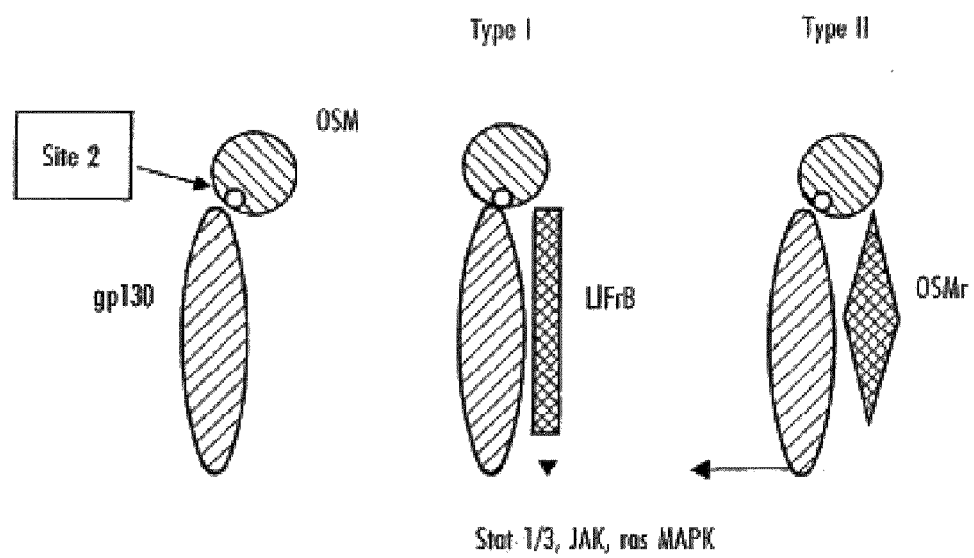

FIG. 27: Human Primary Hepatocyte Assay—Inhibition of C-Reactive Protein (CRP) release by H0(huCDRH1)L1 from human hepatocytes stimulated with (A) 3 ng/ml and (B) 10 ng/ml human OSM. Humanised 15E10 was added for comparison purposes. Data shown are representative of one of three hepatocyte donors.

FIG. 28: Human RA Fibroblast-Like Assay—Inhibition of IL-6 release by H0(huCDRH1)L1 from human RA fibroblast-like synoviocyte (HFLS-RA) cells stimulated with (A) 0.3 ng/ml and (B) 3 ng/ml of human OSM. Humanised 15E10 was added for comparison purposes. Data shown are representative of one of three HFLS-RA donors.

FIG. 29: Human RA Fibroblast-Like Assay—Inhibition of MCP-1 release by H0(huCDRH1)L1 from human RA fibroblast-like synoviocyte (HFLS-RA) cells stimulated with (A) 0.3 ng/ml and (B) 3 ng/ml of human OSM. Humanised 15E10 was added for comparison purposes. Data shown are representative of one of three HFLS-RA donors.

FIG. 30: Human Umbilical Vein Endothelial Cell Assay—Inhibition of IL-6 release by H0(huCDRH1)L1 from human umbilical vein endothelial cells stimulated with (A) 30 ng/ml and (B) 100 ng/ml of human OSM. Humanised 15E10 was added for comparison purposes. Data shown are representative of one of three assay repeats.

FIG. 31: Human Lung Fibroblast Assay—Inhibition of MCP-1 release by H0(huCDRH1)L1 from human lung fibroblast stimulated with human OSM. Humanised 15E10 was added for comparison purposes. Data shown are representative of (A) one healthy and (B) one IPF donor.

FIG. 32: Human Lung Fibroblast Assay—Inhibition of IL-6 release by H0(huCDRH1)L1 from human lung fibroblast stimulated with human OSM. Humanised 15E10 (labelled Antibody X) was added for comparison purposes. Data shown are representative of (A) one healthy and (B) one IPF donor.

FIG. 33: CDRH3 variant binding data—Alanine scanning was performed on the residues found in CDRH3. The data provided shows how binding affinity is affected by a change is such a residue.

FIG. 34: Illustration of the interaction between hOSM and gp130, LIFR and OSMR.

Nomenclature of antibodies—For the avoidance of doubt 15E10h and humanised 15E10 relate to the same antibody and are labelled Antibody X in some figures. Also 10G8/A9 and 10G8 relate to the same antibody.

SUMMARY OF THE INVENTION

The present invention provides antigen binding proteins which are capable of binding to OSM, for example antibodies which specifically bind to OSM and which inhibit the binding of OSM to the gp130 receptor but do not directly interact with site II residues.

The OSM antibodies of the present invention are related to, or derived from a murine mAb 10G8. The 10G8 murine heavy chain variable region amino acid sequence is provided as SEQ ID NO. 26 and the 10G8 murine light chain variable region amino acid sequence is provided as SEQ ID NO. 28.

The heavy chain variable regions (VH) of the present invention may comprise the following CDRs or variants of these CDR's (as defined by Kabat (Kabat et al; Sequences of proteins of Immunological Interest NIH, 1987)):
CDRH1 of SEQ ID NO. 1 or SEQ ID NO 77
CDRH2 of SEQ ID NO. 2
CDRH3 of SEQ ID NO. 3

The light chain variable regions (VL) of the present invention may comprise the following CDRs or variants of these CDR's (as defined by Kabat (Kabat et al; Sequences of proteins of Immunological Interest NIH, 1987)):
CDRL1 of SEQ ID NO. 4
CDRL2 of SEQ ID NO. 5 or SEQ ID NO 78
CDRL3 of SEQ ID NO. 6

The invention also provides a polynucleotide sequence encoding a heavy chain of any of the antigen-binding proteins described herein, and a polynucleotide encoding a light chain of any of the antigen-binding proteins described herein. Such polynucleotides represent the coding sequence which corresponds to the equivalent polypeptide sequences, however it will be understood that such polynucleotide sequences could be cloned into an expression vector along with a start codon, an appropriate signal sequence and a stop codon.

The invention also provides a recombinant transformed or transfected host cell comprising one or more polynucleotides encoding a heavy chain and or a light chain of any of the antigen-binding proteins described herein.

The invention further provides a method for the production of any of the antigen-binding proteins described herein which method comprises the step of culturing a host cell comprising a first and second vector, said first vector comprising a polynucleotide encoding a heavy chain of any of the antigen-binding proteins described herein and said second vector comprising a polynucleotide encoding a light chain of any of the antigen-binding proteins described herein, in a suitable culture media, for example serum-free culture media.

The invention further provides a pharmaceutical composition comprising an antigen-binding protein as described herein and a pharmaceutically acceptable carrier.

In a further aspect, the present invention provides a method of treatment or prophylaxis of a disease or disorder responsive to modulation of the interaction between hOSM and gp130 which method comprises the step of administering to said patient a therapeutically effective amount of the antigen binding protein thereof as described herein.

It is therefore an object of the present invention to provide a therapeutic approach to the treatment of RA and other diseases and disorders, particularly chronic inflammatory diseases and disorders such as osteoarthritis, idiopathic pulmonary fibrosis, pain, inflammatory lung disease, cardiovascular disease and psoriasis. In particular it is an object of the present invention to provide immunoglobulins, especially antibodies that specifically bind OSM (e.g. hOSM, particularly Site II thereof) and modulate (i.e. inhibit or block) the interaction between OSM and gp130 in the treatment of diseases and disorders responsive to modulation of that interaction.

In another aspect of the present invention there is provided a method of treating a human patient afflicted with an inflammatory disease or disorder which method comprises the step of administering to said patient a therapeutically effective amount of the antigen binding protein as described herein. In another aspect of the present invention there is provided a method of humanising an antibody which method comprises the steps of: obtaining a non-human antibody which binds to a target antigen, obtaining the crystallographic structure of the antibody-antigen co crystal, determining to about 2-5 Å from the crystal structure the residues of the non-human antibody involved directly in binding to the antigen, mutating one or more of the residues not involved in binding to a residue derived from a human sequence and recovering said antibody.

DETAILED DESCRIPTION OF THE INVENTION

The present invention provides an antigen binding protein which specifically binds to OSM, for example which specifically binds human OSM (hOSM) and which inhibits the binding of OSM to the gp130 receptor but does not directly interact with site II residues.

In a further aspect of the invention as herein described the antigen binding protein does not directly bind to residues Q20, G120, Q16, N124.

In a further aspect of the invention as herein described there is provided an antigen binding protein which specifically binds to OSM, for example which specifically binds human OSM (hOSM) and which inhibits the binding of OSM to the gp130 receptor and which interacts with one or more of residues 82, 83, 84, 90, 94, 112, 115, 122, 123, 152 of hu OSM.

In one such aspect the invention provides an antigen binding protein which specifically binds to OSM, for example which specifically binds human OSM (hOSM) and which inhibits the binding of OSM to the gp130 receptor but does not directly interact with site II residues and which does not compete with an antibody which has a heavy chain of SEQ ID NO. 79 and a light chain of SEQ ID NO. 80 in a competition ELISA assay.

In one such aspect the invention provides an antigen binding protein which competes with the antigen binding protein as described herein for binding to OSM for example to human OSM.

In another aspect the antigen binding protein binds to human OSM with high affinity for example when measured by Biacore the antigen binding protein binds to human OSM with an affinity of 500 pM or less or an affinity of 400 pM or less, or 300 pM or less, or 250 pM or less, or 200 pM or less, or for example 140 pM or less. In a further embodiment the antigen binding protein binds to human OSM when measured by Biacore of between about 100 pM and about 500 pM or between about 100 pM and about 300 pM, or between about 100 pM and about 250 pM, or between about 100 pM and about 200 pM. In one embodiment of the present invention the antigen binding protein binds OSM with an affinity of less than 250 pm. In a further embodiment of the present invention the antigen binding protein binds OSM with an affinity of less than 140 pm.

In one such embodiment, this is measured by Biacore, for example as set out in Example 2.5.1.

In another aspect the antigen binding protein binds to human OSM with high affinity for example when measured by the solution based Kinexa method the antigen binding protein binds to human OSM with an affinity of 200 pM or less or an affinity of 150 pM or less, or 100 pM or less, or 50 pM or less or for example 40 pM or less. In a further embodiment the antigen binding protein binds to human OSM when measured by Kinexa of between about 10 pM and about 200 pM or between about 10 pM and about 150 pM, or between about 10 pM and about 100 pM, or between about 10 pM and about 70 pM or between about 10 pM and about 40 pM. In one embodiment of the present invention the antigen binding protein binds OSM with an affinity of less than 70 pm. In a further embodiment of the present invention the antigen binding protein binds OSM with an affinity of less than 40 pm.

In one such embodiment, this is measured by Kinexa, for example as set out in Example 2.5.1

In another aspect the antigen binding protein binds to human OSM and neutralises OSM in a cell neutralisation assay wherein the antigen binding protein has an IC50 of between about 10 pM and about 200 pM, or between about 10 pM and about 150 pM, or between about 10 pM and about 100 pM, or between about 20 pM and about 100 pM, or between about 20 pM and about 100 pM. In a further embodiment of the present invention the antigen binding protein binds OSM and neutralises OSM in a cell neutralisation assay wherein the antigen binding protein has an IC50 of about 20 pM with an affinity of less than 140 pm.

In one such embodiment, this is measured by a cell neutralisation assay, for example as set out in Example 2 section 2.2.1.

In one aspect the present invention further provides that the antigen binding protein comprises CDRH3 of SEQ ID NO. 3 or a variant of SEQ ID NO. 3 wherein CDRH3 is substituted by the alternative amino acids set out below at one or more of the following positions (using Kabat numbering):
Position 95 is substituted for Ala, Glu, Gly, His, Leu, Met, Pro, Gln, Ser, Thr, or Val
Position 96 is substituted for Ala, Cys, Phe, Gly, His, Lys, Leu, Ser, Thr, Trp or Tyr
Position 97 is substituted for Ala, Cys, Phe, Met or Ser
Position 98 is substituted for Ala, Asp, Phe, Gly, Leu, Pro, Gln or Trp
Position 99 is substituted for Ala, Cys, Pro, Ser, Val or Tyr
Position 1006 is substituted for Glu
Position 100C is substituted for Ala, Glu, Phe, Gly, Val or Trp
Position 100D is substituted for Ala, Cys, Asp, Glu, Gly, Leu, Ser, Thr, Val, Trp or Tyr
Position 101 is substituted for Glu, Gly, Ser, Thr or Val
Position 102 is substituted for Ala, Phe, Gly, Leu, Pro, Gln, Arg, Ser Tyr, His, Ile, Asp or Trp In a further aspect of the invention the antigen binding protein comprises:
i) CDRH3 as set out in SEQ ID NO. 3 or a variant of SEQ ID NO. 3 wherein Val 102 is substituted for Tyr, His, Ile, Ser, Asp or Gly
ii) CDRH2 as set out in SEQ ID NO. 2 or a variant of SEQ ID NO. 2 wherein Thr50 is substituted for Gly, Tyr, Phe, Ile, Glu or Val and/or Ile51 is substituted for Leu, Val, Thr, Ser or Asn and/or Ser52 is substituted for Phe, Trp or His and/or Gly53 is substituted for Asp, Ser or Asn and/or Gly54 is substituted for Ser and/or Phe56 is substituted for Ser, Tyr, Thr, Asn, Asp or Arg and/or Tyr58 is substituted for Gly, His, Phe, Asp or Asn.
iii) CDRL1 as set out in SEQ ID NO. 4 or a variant of SEQ ID NO. 4 wherein Ser27A is substituted for Asn, Asp, Thr or Glu and/or Ser 27C is substituted for Asp, Leu, Tyr, Val, Ile, Asn, Phe, His, Gly or Thr and/or Asn 31 is substituted for Ser, Thr, Lys or Gly and/or Phe32 is substituted for Tyr, Asn, Ala, His, Ser or Arg and/or Met 33 is substituted for Leu, Val, Ile or Phe.
iv) CDRL3 as set out in SEQ ID NO. 6 or a variant of SEQ ID NO. 6 wherein Leu89 is substituted for Gln, Ser, Gly or Phe and/or His90 is substituted for Gln or Asn, Ser 91 is substituted for Asn, Phe, Gly, Arg, Asp, His, Thr, Tyr or Val and/or Arg92 is substituted for Asn, Tyr, Trp, Thr, Ser, Gln, His, ala or Asp and/or Glu93 is substituted for Asn, Gly, His, Thr, Ser, Ar or Ala and/or Phe96 is substituted for Pro, Leu, Tyr, Arg, Ile, or Trp.

In yet a further aspect the antigen binding protein further comprises:
v) CDRL2 as set out in SEQ ID NO. 5 or SEQ ID NO. 78

In yet a further aspect the antigen binding protein further comprises:
vi) CDRH1 as set out in SEQ ID NO. 1 or SEQ ID NO. 77 or a variant of SEQ ID NO. 1 or SEQ ID NO. 77 wherein Tyr 32 is substituted for Ile, His, Phe, Thr, Asn, Cys, Glu or Asp and/or Ala 33 is substituted for Tyr, Trp, Gly, Thr, Leu or Val and/or Met 34 is substituted for Ile, Val, Trp and/or Ser 35 is substituted for His, Glu, Asn, Gln, Tyr or Thr.

The variant CDR sequences for CDR's L1, L2, L3, H1 and H2 have been determined using mutagenesis and or canonical technology. The complementarity determining regions (CDRs) L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

In one aspect the invention provides an antigen binding protein which comprises CDR H3 of SEQ. ID. NO: 3: CDRH2: SEQ. ID. NO: 2: CDRL1: SEQ. ID. NO: 4 and CDRL3: SEQ. ID. NO: 6 and may further comprise CDR H1 of SEQ. ID. NO: 1 or SEQ ID NO 77 and CDRL2: SEQ. ID. NO: 5 or SEQ ID NO. 78

In another aspect the antigen binding protein comprises CDR H3 of SEQ. ID. NO: 3: CDRH2: SEQ. ID. NO: 2: CDRL1: SEQ. ID. NO: 4: CDRL2: SEQ. ID. NO: 5 and CDRL3: SEQ. ID. NO: 6.

In yet another aspect the antigen binding protein comprises CDR H3 of SEQ. ID. NO: 3: CDRH2: SEQ. ID. NO: 2: CDR H1 of SEQ. ID. NO: 1: CDRL1: SEQ. ID. NO: 4: CDRL2: SEQ. ID. NO: 5 and CDRL3: SEQ. ID. NO: 6.

In yet another aspect the antigen binding protein comprises CDR H3 of SEQ. ID. NO: 3: CDRH2: SEQ. ID. NO: 2: CDR H1 of SEQ. ID. NO: 1: CDRL1: SEQ. ID. NO: 4: CDRL2: SEQ. ID. NO: 78 and CDRL3: SEQ. ID. NO: 6.

In yet another aspect the antigen binding protein comprises CDR H3 of SEQ. ID. NO: 3: CDRH2: SEQ. ID. NO: 2: CDR H1 of SEQ. ID. NO: 77: CDRL1: SEQ. ID. NO: 4: CDRL2: SEQ. ID. NO: 5 and CDRL3: SEQ. ID. NO: 6.

In yet another aspect the antigen binding protein comprises CDR H3 of SEQ. ID. NO: 3: CDRH2: SEQ. ID. NO: 2: CDR H1 of SEQ. ID. NO: 77: CDRL1: SEQ. ID. NO: 4: CDRL2: SEQ. ID. NO: 78 and CDRL3: SEQ. ID. NO: 6.

In one aspect of the present invention the antigen binding protein does not interact directly via CDR H1 with OSM.

In one aspect the antigen binding protein does not interact directly via CDR H1 or CDR L2 with OSM.

The antigen binding proteins of the invention may comprise heavy chain variable regions and light chain variable regions of the invention which may be formatted into the structure of a natural antibody or functional fragment or equivalent thereof. An antigen binding protein of the invention may therefore comprise the VH regions of the invention formatted into a full length antibody, a (Fab')2 fragment, a Fab fragment, or equivalent thereof (such as scFV, bi- tri- or tetra-bodies, Tandabs etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antigen binding protein may comprise modifications of all classes e.g. IgG dimers, Fc mutants that no longer bind Fc receptors or mediate C1q binding. The antigen binding protein may also be a chimeric antibody of the type described in WO86/01533 which comprises an antigen binding region and a non-immunoglobulin region.

The constant region is selected according to any functionality required. An IgG1 may demonstrate lytic ability through binding to complement and/or will mediate ADCC (antibody dependent cell cytotoxicity). An IgG4 can be used if a non-cytotoxic blocking antibody is required. However, IgG4 antibodies can demonstrate instability in production and therefore an alternative is to modify the generally more stable IgG1. Suggested modifications are described in EP0307434, for example mutations at positions 235 and 237. The invention therefore provides a lytic or a non-lytic form of an antigen binding protein, for example an antibody according to the invention.

In certain forms the antibody of the invention is a full length (e.g. H2L2 tetramer) lytic or non-lytic IgG1 antibody having any of the heavy chain variable regions described herein.

The antigen binding proteins of the present invention are derived from the murine antibody having the variable regions as described in SEQ ID NO:26 and SEQ ID NO:28 or non-murine equivalents thereof, such as rat, human, chimeric or humanised variants thereof, for example they are derived from the humanised antibody having the heavy and light chains as described in SEQ ID NO:54 and SEQ ID NO:62.

In one aspect of the invention there is provided an antigen binding protein comprising an isolated heavy chain variable domain selected from any on the following: SEQ ID NO 54, SEQ ID NO 56, SEQ ID NO. 58 or SEQ ID NO: 74.

In another aspect of the invention there is provided an antigen binding protein comprising an isolated light chain variable domain selected from any on the following: SEQ ID NO 62, SEQ ID NO 64, SEQ ID NO. 66 or SEQ ID NO. 68.

In a further aspect of the invention there is provided an antigen binding protein comprising an isolated heavy chain variable domain selected from any on the following: SEQ ID NO 54, SEQ ID NO 56, SEQ ID NO. 58 or SEQ ID NO: 74 and a an isolated light chain variable domain selected from any on the following: SEQ ID NO 62, SEQ ID NO 64, SEQ ID NO. 66 or SEQ ID NO. 68.

In a further embodiment of the invention there is provided an antigen binding protein comprising an isolated heavy chain variable domain of SEQ ID NO 54 and an isolated light chain variable domain of SEQ ID NO 62. In a further embodiment the antigen binding protein comprises a heavy chain variable region of SEQ. ID. NO:74 and a light chain variable region of SEQ. ID. NO:62.

In one aspect the antigen binding protein of the present invention comprises a heavy chain variable region encoded by SEQ. ID. NO:53 and a light chain variable region encoded by SEQ. ID. NO:61 In one aspect the antigen binding protein of the present invention comprises a heavy chain variable region encoded by SEQ. ID. NO:73 and a light chain variable region encoded by SEQ. ID. NO:61.

In one aspect there is provided a polynucleotide encoding an isolated variable heavy chain said polynucleotide comprising SEQ. ID. NO. 53, or SEQ. ID. NO. 55, or SEQ. ID. NO. 57, or SEQ. ID. NO. 73.

In one aspect there is provided a polynucleotide encoding an isolated variable light chain said polynucleotide comprising SEQ. ID. NO. 61, or SEQ. ID. NO. 63, or SEQ. ID. NO. 65, or SEQ. ID. NO. 67.

In a further aspect there is provided a polynucleotide encoding an isolated variable heavy chain said polynucleotide comprising SEQ. ID. NO. 53, or SEQ. ID. NO. 73 and a polynucleotide encoding an isolated variable light chain said polynucleotide comprising SEQ. ID. NO. 61, or SEQ. ID. NO. 63, or SEQ. ID. NO. 65, or SEQ. ID. NO. 67. In yet a further aspect there is provided a polynucleotide encoding an isolated variable heavy chain said polynucleotide comprising SEQ. ID. NO. 53 or SEQ. ID. NO. 73 and a polynucleotide encoding an isolated variable light chain said polynucleotide comprising SEQ. ID. NO. 61.

In a further aspect the antigen binding protein may comprise any one of the variable heavy chains as described herein in combination with any one of the light chains as described herein.

In one aspect the antigen binding protein is an antibody or antigen binding fragment thereof comprising one or more CDR's according to the invention described herein, or one or both of the heavy or light chain variable domains according to the invention described herein. In one embodiment the antigen binding protein binds primate OSM. In one such embodiment the antigen binding protein additionally binds non-human primate OSM, for example cynomolgus macaque monkey OSM. In another embodiment the antigen binding protein binds marmoset OSM.

In one aspect there is provided an antigen binding protein which binds to both Marmoset and human OSM with an affinity stronger than 1 nM when measured by Biacore or Kinexa.

The ability of these antibodies to neutralise marmoset OSM provides a unique means to assess the role of OSM in marmoset disease models, such as the EAE model of MS, for additional indications In another aspect the antigen binding protein is selected from the group consisting of a dAb, Fab, Fab', F(ab')$_2$, Fv, diabody, triabody, tetrabody, miniantibody, and a minibody.

In one aspect of the present invention the antigen binding protein is a humanised or chimaeric antibody, in a further aspect the antibody is humanised.

In one aspect the antibody is a monoclonal antibody.

The present invention further provides that in one aspect the antigen binding protein comprises:
i) CDRH3 as set out in SEQ ID NO. 3 or a variant of SEQ ID NO. 3 wherein CDRH3 is substituted by the alternative amino acids set out below at one or more of the following positions (using Kabat numbering):
Position 95 is substituted for Ala, Glu, Gly, His, Leu, Met, Pro, Gln, Ser, Thr, or Val
Position 96 is substituted for Ala, Cys, Phe, Gly, His, Lys, Leu, Ser, Thr, Trp or Tyr
Position 97 is substituted for Ala, Cys, Phe, Met or Ser
Position 98 is substituted for Ala, Asp, Phe, Gly, Leu, Pro, Gln or Trp
Position 99 is substituted for Ala, Cys, Pro, Ser, Val or Tyr
Position 100B is substituted for Glu
Position 100C is substituted for Ala, Glu, Phe, Gly, Val or Trp
Position 100D is substituted for Ala, Cys, Asp, Glu, Gly, Leu, Ser, Thr, Val, Trp or Tyr
Position 101 is substituted for Glu, Gly, Ser, Thr or Val
Position 102 is substituted for Ala, Phe, Gly, Leu, Pro, Gln, Arg, Ser Tyr, His, Ile, Asp or Trp
ii) CDRH1 as set out in SEQ ID NO. 1 or SEQ ID NO. 77 or a variant of SEQ ID NO. 1 or SEQ ID NO. 77 wherein Tyr 32 is substituted for Ile, His, Phe, Thr, Asn, Cys, Glu or Asp and/or Ala 33 is substituted for Tyr, Trp, Gly, Thr, Leu or Val and/or Met 34 is substituted for Ile, Val or Trp and/or Ser 35 is substituted for His, Glu, Asn, Gln, Tyr or Thr.
iii) CDRH2 as set out in SEQ ID NO. 2 or a variant of SEQ ID NO. 2 wherein Thr50 is substituted for Gly, Tyr, Phe, Ile, Glu or Val and/or Ile51 is substituted for Leu, Val, Thr, Ser or Asn and/or Ser52 is substituted for Phe, Trp or His and/or Gly53 is substituted for Asp, Ser or Asn and/or Gly54 is substituted for Ser and/or Phe56 is substituted for Ser, Tyr, Thr, Asn, Asp or Arg and/or Tyr58 is substituted for Gly, His, Phe, Asp or Asn.
iv) CDRL1 as set out in SEQ ID NO. 4 or a variant of SEQ ID NO. 4 wherein Ser27A is substituted for Asn, Asp, Thr or Glu and/or Ser 27C is substituted for Asp, Leu, Tyr, Val, Ile, Asn, Phe, His, Gly or Thr and/or Asn 31 is substituted for Ser, Thr, Lys or Gly and/or Phe32 is substituted for Tyr, Asn, Ala, His, Ser or Arg and/or Met 33 is substituted for Leu, Val, Ile or Phe.
v) CDRL2 as set out in SEQ ID NO. 5 or SEQ ID NO. 78
vi) CDRL3 as set out in SEQ ID NO. 6 or a variant of SEQ ID NO. 6 wherein Leu89 is substituted for Gln, Ser, Gly or Phe and/or His90 is substituted for Gln or Asn, Ser 91 is substituted for Asn, Phe, Gly, Arg, Asp, His, Thr, Tyr or Val and/or Arg92 is substituted for Asn, Tyr, Trp, Thr, Ser, Gln, His, ala or Asp and/or Glu93 is substituted for Asn, Gly, His, Thr, Ser, Ar or Ala and/or Phe96 is substituted for Pro, Leu, Tyr, Arg, Ile, or Trp.
vii) the heavy chain framework comprises the following residues:
Position 2 Val, Ile or Gly,
Position 4 Leu or Val
Position 20 Leu, Ile, Met or Val
Position 22 Cys
Position 24 Thr, Ala, Val, Gly or Ser
Position 26 Gly
Position 29 Ile, Phe, Leu or Ser
Position 36 Trp
Position 47 Trp
Position 48 Ile, met, Val or Leu
Position 69 Ile, Leu, Phe, Met or Val
Position 71 Arg
Position 78 Ala, Leu, Val, Tyr or Phe
Position 80 Leu, Met,
Position 90 Tyr or Phe
Position 92 Cys
Position 94 Arg, Lys, Gly, Ser, His or Asn The present invention further provides that in one aspect the antigen binding protein comprises:
i) CDRH3 as set out in SEQ ID NO. 3
ii) CDRH1 as set out in SEQ ID NO. 1 or SEQ ID NO. 77
iii) CDRH2 as set out in SEQ ID NO. 2
iv) CDRL1 as set out in SEQ ID NO. 4
v) CDRL2 as set out in SEQ ID NO. 5 or SEQ ID NO. 78
vi) CDRL3 as set out in SEQ ID NO. 6
vii) the heavy chain framework comprises the following residues:
Position 2 Val, Ile or Gly,
Position 4 Leu or Val
Position 20 Leu, Ile, Met or Val
Position 22 Cys
Position 24 Thr, Ala, Val, Gly or Ser
Position 26 Gly
Position 29 Ile, Phe, Leu or Ser
Position 36 Trp
Position 47 Trp
Position 48 Ile, met, Val or Leu
Position 69 Ile, Leu, Phe, Met or Val
Position 71 Arg
Position 78 Ala, Leu, Val, Tyr or Phe
Position 80 Leu, Met,
Position 90 Tyr or Phe Position 92 Cys
Position 94 Arg, Lys, Gly, Ser, His or Asn The present invention further provides that in one aspect the antigen binding protein comprises:
i) CDRH3 as set out in SEQ ID NO. 3
ii) CDRH1 as set out in SEQ ID NO. 1 or SEQ ID NO. 77
iii) CDRH2 as set out in SEQ ID NO. 2
iv) CDRL1 as set out in SEQ ID NO. 4
v) CDRL2 as set out in SEQ ID NO. 5 or SEQ ID NO. 78
vi) CDRL3 as set out in SEQ ID NO. 6
vii) the heavy chain framework comprises the following residues:
  Position 2 Val
  Position 4 Leu
  Position 20 Leu
  Position 22 Cys
  Position 24 Ala
  Position 26 Gly
  Position 29 Phe
  Position 36 Trp
  Position 47 Trp
  Position 48 Val
  Position 69 Ile
  Position 71 Arg
  Position 78 Leu
  Position 80 Leu
  Position 90 Tyr
  Position 92 Cys
  Position 94 Arg The present invention further provides that in one aspect the antigen binding protein comprises:
i) CDRH3 as set out in SEQ ID NO. 3
ii) CDRH1 as set out in SEQ ID NO. 1 or SEQ ID NO. 77
iii) CDRH2 as set out in SEQ ID NO. 2
iv) CDRL1 as set out in SEQ ID NO. 4
v) CDRL2 as set out in SEQ ID NO. 5 or SEQ ID NO. 78
vi) CDRL3 as set out in SEQ ID NO. 6
vii) the heavy chain framework comprises the following residues:
  Position 2 Val
  Position 4 Leu
  Position 20 Leu
  Position 22 Cys
  Position 24 Ala
  Position 26 Gly
  Position 29 Phe
  Position 36 Trp
  Position 47 Trp
  Position 48 Leu
  Position 69 Ile, Leu, Phe, Met or Val
  Position 71 Arg
  Position 78 Ala
  Position 80 Leu, Met,
  Position 90 Tyr or Phe
  Position 92 Cys
  Position 94 Arg, Lys, Gly, Ser, His or Asn The antigen binding proteins, for example antibodies of the present invention may be produced by transfection of a host cell with an expression vector comprising the coding sequence for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of E. coli may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparations of altered antibodies are described in WO 99/58679 and WO 96/16990.

Yet another method of expression of the antigen binding proteins may utilize expression in a transgenic animal, such as described in U.S. Pat. No. 4,873,316. This relates to an expression system using the animals casein promoter which when transgenically incorporated into a mammal permits the female to produce the desired recombinant protein in its milk.

In a further embodiment of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an anti-OSM antibody of the present invention which binds to and neutralises the activity of human OSM which method comprises the steps of;
(a) providing a first vector encoding a heavy chain of the antibody;
(b) providing a second vector encoding a light chain of the antibody;
(c) transforming a mammalian host cell (e.g. CHO) with said first and second vectors;
(d) culturing the host cell of step (c) under conditions conducive to the secretion of the antibody from said host cell into said culture media;
(e) recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to OSM. Additionally, other in vitro assays may also be used to verify neutralizing efficacy prior to subsequent human clinical studies performed to evaluate the persistence of the antibody in the body despite the usual clearance mechanisms.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) maybe required to achieve maximal therapeutic efficacy.

In one embodiment of the present invention there is provided a recombinant transformed, transfected or transduced host cell comprising at least one expression cassette, for example where the expression cassette comprises a polynucleotide encoding a heavy chain of an antigen binding protein according to the invention described herein and further comprises a polynucleotide encoding a light chain of an antigen binding protein according to the invention described herein or where there are two expression cassettes and the 1st encodes the light chain and the second encodes the heavy chain. For example in one embodiment the first expression cassette comprises a polynucleotide encoding a heavy chain of an antigen binding protein comprising a constant region or antigen binding fragment thereof which is linked to a constant region according to the invention described herein and further comprises a second cassette comprising a polynucleotide encoding a light chain of an antigen binding protein comprising a constant region or antigen binding fragment thereof which is linked to a constant region according to the invention described herein for example the first expression cassette comprises a polynucleotide encoding a heavy chain selected from SEQ. ID. NO: 70, or SEQ. ID. NO: 76 and a second expression cassette comprising a polynucleotide encoding a light chain selected from SEQ. ID. NO: 72.

It will be understood that the sequences described herein (SEQ ID NO. 25, 27, 29, 31, 33, 35, 37, 39, 41, 43, 45, 47, 49, 51, 53, 55, 57, 59, 61, 63, 65, 67, 69, 71, 73, 75, 83) include sequences which are substantially identical, for example sequences which are at least 90% identical, for example which are at least 91%, or at least 92%, or at least 93%, or at least 94% or at least 95%, or at least 96%, or at least 97% or at least 98%, or at least 99% identical to the sequences described herein.

For nucleic acids, the term "substantial identity" indicates that two nucleic acids, or designated sequences thereof, when optimally aligned and compared, are identical, with appropriate nucleotide insertions or deletions, in at least about 80% of the nucleotides, at least about 90% to about 95%, or at least about 98% to about 99.5% of the nucleotides. Alternatively, substantial identity exists when the segments will hybridize under selective hybridization conditions, to the complement of the strand.

For nucleotide and amino acid sequences, the term "identical" indicates the degree of identity between two nucleic acid or amino acid sequences when optimally aligned and compared with appropriate insertions or deletions. Alternatively, substantial identity exists when the DNA segments will hybridize under selective hybridization conditions, to the complement of the strand.

In another embodiment of the invention there is provided a stably transformed host cell comprising a vector comprising one or more expression cassettes encoding a heavy chain and/or a light chain of the antibody comprising a constant region or antigen binding fragment thereof which is linked to a constant region as described herein. For example such host cells may comprise a first vector encoding the light chain and a second vector encoding the heavy chain, for example the first vector encodes a heavy chain selected from SEQ. ID. NO: 70, or SEQ. ID. NO: 76 and a second vector encoding a light chain for example the light chain of SEQ ID NO: 72.

In another embodiment of the present invention there is provided a host cell according to the invention described herein wherein the cell is eukaryotic, for example where the cell is mammalian. Examples of such cell lines include CHO or NS0.

In another embodiment of the present invention there is provided a method for the production of an antibody comprising a constant region or antigen binding fragment thereof which is linked to a constant region according to the invention described herein which method comprises the step of culturing a host cell in a culture media, for example serum-free culture media.

In another embodiment of the present invention there is provided a method according to the invention described herein wherein said antibody is further purified to at least 95% or greater (e.g. 98% or greater) with respect to said antibody containing serum-free culture media.

In yet another embodiment there is provided a pharmaceutical composition comprising an antigen binding protein and a pharmaceutically acceptable carrier.

In another embodiment of the present invention there is provided a kit-of-parts comprising the composition according to the invention described herein described together with instructions for use.

The mode of administration of the therapeutic agent of the invention may be any suitable route which delivers the agent to the host. The antigen binding proteins, and pharmaceutical compositions of the invention are particularly useful for parenteral administration, i.e., subcutaneously (s.c.), intrathecally, intraperitoneally, intramuscularly (i.m.) or intravenously (i.v.).

Therapeutic agents of the invention may be prepared as pharmaceutical compositions containing an effective amount of the antigen binding protein of the invention as an active ingredient in a pharmaceutically acceptable carrier. In one embodiment the prophylactic agent of the invention is an aqueous suspension or solution containing the antigen binding protein in a form ready for injection. In one embodiment the suspension or solution is buffered at physiological pH. In one embodiment the compositions for parenteral administration will comprise a solution of the antigen binding protein of the invention or a cocktail thereof dissolved in a pharmaceutically acceptable carrier. In one embodiment the carrier is an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding protein of the invention in such pharmaceutical formulation can vary widely, i.e., from less than about 0.5%, usually at or at least about 1% to as much as about 15 or 20% by weight and will be selected primarily based on fluid volumes, viscosities, etc., according to the particular mode of administration selected.

Thus, a pharmaceutical composition of the invention for intramuscular injection could be prepared to contain about 1 mL sterile buffered water, and between about 1 ng to about 100 mg, e.g. about 50 ng to about 30 mg or about 5 mg to about 25 mg, of an antigen binding protein, for example an antibody of the invention. Similarly, a pharmaceutical composition of the invention for intravenous infusion could be made up to contain about 250 ml of sterile Ringer's solution, and about 1 to about 30 or 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antigen binding protein formulations of the invention see Lasmar U and Parkins D "The formulation of Biopharmaceutical products", Pharma. Sci. Tech. today, page 129-137, Vol. 3 (3 Apr. 2000); Wang, W "Instability, stabilisation and formulation of liquid protein pharmaceuticals", Int. J. Pharm 185 (1999) 129-188; Stability of Protein Pharmaceuticals Part A and B ed Ahern T. J., Manning M. C., New York, N.Y.: Plenum Press (1992); Akers, M. J. "Excipient-Drug interactions in Parenteral Formulations", J. Pharm Sci 91 (2002) 2283-2300; Imamura, K et al "Effects of types of sugar on stabilization of Protein in the dried state", J Pharm Sci 92 (2003) 266-274; Izutsu, Kkojima, S. "Excipient crystallinity and its protein-structure-stabilizing effect during freeze-drying", J Pharm. Pharmacol, 54 (2002) 1033-1039; Johnson, R, "Mannitol-sucrose mixtures-versatile formulations for protein lyophilization", J. Pharm. Sci, 91 (2002) 914-922; and H a, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

In one embodiment the therapeutic agent of the invention, when in a pharmaceutical preparation, is present in unit dose forms. The appropriate therapeutically effective dose will be determined readily by those of skill in the art. Suitable doses may be calculated for patients according to their weight, for example suitable doses may be in the range of about 0.1 to about 20 mg/kg, for example about 1 to about 20 mg/kg, for example about 10 to about 20 mg/kg or for example about 1 to about 15 mg/kg, for example about 10 to about 15 mg/kg. To effectively treat conditions such as asthma or IPF in a human, suitable doses may be within the range of about 0.1 to about 1000 mg, for example about 0.1 to about 500 mg, for example about 500 mg, for example about 0.1 to about 100 mg, or about 0.1 to about 80 mg, or about 0.1 to about 60 mg, or about 0.1 to about 40 mg, or for example about 1 to about 100 mg, or about 1 to about 50 mg, of an antigen binding protein of this invention, which may be administered parenterally, for example subcutaneously, intravenously or intramuscularly. Such dose may, if necessary, be repeated at appropriate time intervals selected as appropriate by a physician.

The antigen binding proteins described herein can be lyophilized for storage and reconstituted in a suitable carrier prior to use. This technique has been shown to be effective with conventional immunoglobulins and art-known lyophilization and reconstitution techniques can be employed.

In another aspect of the present invention there is provided a method of treating a human patient afflicted with an inflammatory arthropathy such as rheumatoid arthritis, juvenile onset arthritis, osteoarthritis, psoriatic arthritis and ankylosing spondylitis which method comprises the step of administering to said patient a therapeutically effective amount of the antigen binding protein as described herein.

In another aspect of the present invention there is provided a method of treating a human patient afflicted with a disease or disorder selected from type 1 diabetes, psoriasis, inflammatory bowel disease (IBD) including Crohn's disease and ulcerative colitis (UC), systemic lupus erythematosus (SLE, Lupus), atopic dermatitis, allergic rhinitis, chronic obstructive pulmonary disease (COPD), pneumonia, eosinophilic esophagitis, Systemic sclerosis (SS) or Idiopathic Pulmonary Fibrosis (IPF), Sjögren's syndrome, scleroderma, vasculitides (including Takayasu arteritis, giant cell (temporal) arteritis, polyarteritis nodosa, Wegener's granulomatosis, Kawasaki disease, isolated CNS vasculitis, Churg-Strauss arteritis, microscopic polyarteritis/polyangiitis, hypersensitivity vasculitis (allergic vasculitis), Henoch-Schonlein purpura, and essential cryoglobulinemic vasculitis), undifferentiated spondyloarthropathy (USpA), ankylosing spondylitis (AS), graft-versus-host disease (GVHD), primary biliary cirrhosis (PBC), primary sclerosing cholangitis (PSC), idiopathic thrombocytopenic purpura (ITP), multiple sclerosis (MS), and asthma wherein said method comprises the step of administering to said patient a therapeutically effective amount of the antigen binding protein as described herein.

Any one or more of the aforementioned diseases may be the target disease for a method of treatment of the invention.

In a particular aspect, the disease or disorder is selected from the group consisting of Osteoarthrtits, (OA), Psoriasis, Idiopathic Pulmonary Fibrosis (IPF), Systemic sclerosis (SS Sjögren's syndrome, scleroderma, or Multiple Sclerosis (MS.

In one aspect of the present invention the autoimmune disease is Osteoarthritis.

In one aspect of the present invention the autoimmune disease is Psoriasis.

In one aspect of the present invention the autoimmune disease or disorder is a fibrotic disease or disorder.

In one aspect of the present invention the autoimmune disease is Idiopathic Pulmonary Fibrosis (IPF).

In one aspect of the present invention the autoimmune disease is Systemic Sclerosis (SS).

In one aspect of the present invention the autoimmune disease is Sjögren's syndrome.

In one aspect of the present invention the autoimmune disease is Scleroderma.

In another aspect of the invention there is provided a method of reducing or preventing cartilage degradation in a human patient afflicted with (or suspectible to) such degradation which method comprises the step of administering a therapeutically effective amount of the antigen binding protein to said patient as described herein.

In another aspect of the present invention there is provided a method of reducing TNF alpha production in a patient afflicted with a disease or disorder responsive to TNF alpha reduction which method comprises administering to said patient a therapeutically effective amount of the antigen binding protein as described herein In another aspect of the invention there is provided a method of treating the extra articular manifestations of an arthritic disease or disorder e.g. Feltys syndrome and/or treat the formation of atherosclerotic plaques which method comprises the step of administering a therapeutically effective amount of the antigen binding protein as described herein to the human patient afflicted with the extra articular manifestations of an arthritic disease or disorder.

In another aspect of the present invention there is provided a method of treating a human patient afflicted with a disease of endothelial cell origin which method comprises the steps of administering to said patient a therapeutically effective amount of the antigen binding protein as described herein.

In another aspect of the present invention there is provided a method of treating a human patient afflicted with fibrotic diseases or disorders such as idiopathic pulmonary fibrosis, progressive systemic sclerosis (scleroderma), hepatic fibrosis, hepatic granulomas, schistosomiasis, and leishmaniasis which method comprises the steps of administering to said patient a therapeutically effective amount of the antigen binding protein as described herein.

In another aspect of the present invention there is provided a method of treating a human patient afflicted with a disease or disorder of the central nervous system such as multiple sclerosis (MS), Alzheimer's disease (AD) and other dementias and furthermore concerns the use in the treatment of pain, particularly neuropathic and/or inflammatory pain wherein said method comprises the steps of administering to said patient a therapeutically effective amount of the antigen binding protein as described herein.

Use of the antigen binding protein as described herein in the manufacture of a medicament for the treatment of diseases and disorders as described herein is also provided.

For example in one aspect of the invention there is provided the use of the antigen binding protein as described herein for use in the treatment or prophylaxis of diseases and disorders responsive to modulation of the interaction between hOSM and gp130.

In another aspect of the invention there is provided the use of the antigen binding protein as described herein for use in the treatment or prophylaxis of an inflammatory arthropathy such as rheumatoid arthritis, juvenile onset arthritis, osteoarthritis, psoriatic arthritis and ankylosing spondylitis.

In yet another aspect of the invention there is provided the use of the antigen binding protein as described herein for use in the treatment or prophylaxis of a disease or disorder selected from type 1 diabetes, psoriasis, inflammatory bowel disease (IBD) including Crohn's disease and ulcerative colitis (UC), systemic lupus erythematosus (SLE, Lupus), atopic dermatitis, allergic rhinitis, chronic obstructive pulmonary disease (COPD), pneumonia, eosinophilic esophagitis, Systemic sclerosis (SS) or Idiopathic Pulmonary Fibrosis (IPF), Sjögren's syndrome, scleroderma, vasculitides (including Takayasu arteritis, giant cell (temporal) arteritis, polyarteritis nodosa, Wegener's granulomatosis, Kawasaki disease, isolated CNS vasculitis, Churg-Strauss arteritis, microscopic polyarteritis/polyangiitis, hypersensitivity vasculitis (allergic vasculitis), Henoch-Schonlein purpura, and essential cryoglobulinemic vasculitis), undifferentiated spondyloarthropathy (USpA), ankylosing spondylitis (AS), graft-versus-host disease (GVHD), primary biliary cirrhosis (PBC), primary sclerosing cholangitis (PSC), idiopathic thrombocytopenic purpura (ITP), multiple sclerosis (MS), and asthma wherein said method comprises the step of administering to said patient a therapeutically effective amount of the antigen binding protein as described herein.

For example in a particular aspect, use of the antigen binding protein for use in the treatment or prophylaxis of Osteoarthrtits, (OA), Psoriasis, Idiopathic Pulmonary Fibrosis (IPF) or Multiple Sclerosis (MS) is provided.

Other aspects and advantages of the present invention are described further in the detailed description and the embodiments thereof.

In one aspect, the invention provides a pharmaceutical composition comprising an antigen binding protein of the present invention or a functional fragment thereof and a pharmaceutically acceptable carrier for treatment or prophylaxis of inflammatory diseases and or disorders for example, inflammatory arthropathy such as rheumatoid arthritis, juvenile onset arthritis, osteoarthritis, psoriatic arthritis and ankylosing spondylitis or selected from type 1 diabetes, psoriasis, inflammatory bowel disease (IBD) including Crohn's disease and ulcerative colitis (UC), systemic lupus erythematosus (SLE, Lupus), atopic dermatitis, allergic rhinitis, chronic obstructive pulmonary disease (COPD), pneumonia, eosinophilic esophagitis, Systemic sclerosis (SS) or Idiopathic Pulmonary Fibrosis (IPF), Sjögren's syndrome, scleroderma, vasculitides (including Takayasu arteritis, giant cell (temporal) arteritis, polyarteritis nodosa, Wegener's granulomatosis, Kawasaki disease, isolated CNS vasculitis, Churg-Strauss arteritis, microscopic polyarteritis/polyangiitis, hypersensitivity vasculitis (allergic vasculitis), Henoch-Schonlein purpura, and essential cryoglobulinemic vasculitis), undifferentiated spondyloarthropathy (USpA), ankylosing spondylitis (AS), graft-versus-host disease (GVHD), primary biliary cirrhosis (PBC), primary sclerosing cholangitis (PSC), idiopathic thrombocytopenic purpura (ITP), multiple sclerosis (MS), and asthma In another embodiment of the present invention there is provided a method of treating a human patient afflicted with an inflammatory disorder or disease which method comprises the step of administering a therapeutically effective amount of the antigen binding protein according to the invention as described herein, for example there is provided a method of treating a human patient afflicted with an inflammatory disorder or disease which method comprises the step of administering a pharmaceutical composition comprising an antigen binding protein according to the invention herein in combination with a pharmaceutically acceptable carrier. In a further embodiment there is provided a method of treating a human patient afflicted with an inflammatory disorder or disease selected from for example, inflammatory arthropathy such as rheumatoid arthritis, juvenile onset arthritis, osteoarthritis, psoriatic arthritis and ankylosing spondylitis or selected from type 1 diabetes, psoriasis, inflammatory bowel disease (IBD) including Crohn's disease and ulcerative colitis (UC), systemic lupus erythematosus (SLE, Lupus), atopic dermatitis, allergic rhinitis, chronic obstructive pulmonary disease (COPD), pneumonia, eosinophilic esophagitis, Systemic sclerosis (SS) or Idiopathic Pulmonary Fibrosis (IPF), Sjögren's syndrome, scleroderma, vasculitides (including Takayasu arteritis, giant cell (temporal) arteritis, polyarteritis nodosa, Wegener's granulomatosis, Kawasaki disease, isolated CNS vasculitis, Churg-Strauss arteritis, microscopic polyarteritis/polyangiitis, hypersensitivity vasculitis (allergic vasculitis), Henoch-Schonlein purpura, and essential cryoglobulinemic vasculitis), undifferentiated spondyloarthropathy (USpA), ankylosing spondylitis (AS), graft-versus-host disease (GVHD), primary biliary cirrhosis (PBC), primary sclerosing cholangitis (PSC), idiopathic thrombocytopenic purpura (ITP), multiple sclerosis (MS), and asthma In an alternative aspect of the invention there is provided a method for humanising a non-human antibody or antibody fragment thereof which method comprises the steps of:
a) incorporating one or more non-human CDR's onto a human acceptor framework to produce a chimeric or humanised antibody
b) binding the chimeric or humanised antibody to its antigen
c) determining the residues of the antibody involved directly in binding to the antigen
d) mutating one or more of the residues not involved in step (c) to human germline sequence;
e) recovering said antibody.

In a further aspect the residues of the antibody involved in binding to antigen may be determined by crystallography, homology modelling, protein docking, mutagenesis or linear peptide mapping.

For example in one such aspect of the invention as herein described the crystallographic structure of the antibody-antigen co crystal. is obtained and residues involved in binding are determined to be between about 2-5 Å

The term non-human encompasses any antibody which can be mutated or substituted in some way as to bring it closer to a human germline sequence. In this way decreasing the likelihood of immunogenicity.

In one aspect at least one CDR is reverted to germline. In a further aspect at least two CDR's are reverted to germline. In yet a further aspect at least 5 residues are reverted to germline, for example at least 7 or at least 8 or at least 9 or at least 10 residues are reverted to germline.

Transfer of non-human monoclonal antibodies or fragments thereof onto a human acceptor often additionally rely on the introduction of changes within the framework to re-establish proper CDR region-antigen interactions these are often referred to as back mutations. In one embodiment of the present invention back mutations are required in order to re-establish proper CDR-region-antigen interactions.

In an alternative embodiment the human acceptor framework may be incorporated onto an antibody with one or more non-human CDR's to produce a chimeric antibody. In yet an alternative embodiment the sequence may be generated by oilgo-synthesis.

CDR's (or hypervariable region residues) of the non-human antibody are incorporated into the VL and/or VH human acceptor frameworks. For example, one may incorporate residues corresponding to the Kabat CDR residues, the Chothia hypervariable loop residues, the Abm residues, and/or contact residues.

In one embodiment there is provided a method for humanising an antibody which method comprises the steps of:
a) obtaining a non-human antibody which binds to a target antigen
b) obtaining the crystallographic structure of the antibody-antigen co crystal
c) determining to about 2-5 Å from the crystal structure the residues of the non-human antibody involved directly in binding to the antigen
e) mutating one or more of the residues not involved in step (c) to a residue derived from a human sequence;
f) recovering said antibody.

In a further embodiment of the methods described herein the antibody or antibody binding fragment retains binding to its antigen. For example the antibody or antibody binding fragment retains binding to its antigen as compared to the non-human antibody. For example the antibody of step f) has a binding affinity (KD) within or better than 10 fold of the non-human antibody of step a), for example the antibody of step f) has a binding affinity (KD) within or better than 3-5 fold of the non-human antibody of step a).

For example the antibody or antibody binding fragment retains binding to its antigen within 1000 nM of the non-human antibody when measured by Biacore, or within 500 nM of the non-human antibody when measured by Biacore, or within 100 nM of the non-human antibody when measured by Biacore. For example the antibody or antibody binding fragment retains binding to its antigen within 500 pM of the non-human antibody when measured by Biacore, or within 300 pM of the non-human antibody when measured by Biacore, or within 100 pM of the non-human antibody when measured by Biacore.

For example the antibody of step f) binds to its antigen with an affinity (KD) that is equal to or less than 400 pM or equal to or less than 300 pM, or is equal to or less than 200 pM or is equal to or less than 140 pM.

In another embodiment of the methods described herein the antibody or antibody binding fragment retains the same canonical structures as the non-human antibody or antibody fragment.

In yet another embodiment the non-human antibody or antibody fragment thereof is from a non human animal, for example mouse, rat, rabbit, camelid or shark.

In a further embodiment the non-human antibody or antibody fragment thereof is from a mouse.

In yet another embodiment the non-human antibody or antibody fragment thereof is a monoclonal antibody, polyclonal antibody or multispecific antibody or this may be an immunoglobulin single variable domain for example a camelid or shark immunoglobulin single variable domain or it may be a domain which is a derivative of a non-human non antibody protein scaffold.

In yet a further embodiment the non-human antibody is a monoclonal antibody.

In one embodiment of the methods described herein at least 2 non-human CDR's are incorporated into the human acceptor sequence, or at least 3 CDR's or at least 4 CDR's or at least 5' CDR's or all 6 CDR's are incorporated to the human acceptor sequence.

In a further embodiment of the methods described herein the residues to be mutated to a residue derived from a human sequence which are not involved directly in binding antigen and are not already human, may be residues in the CDR's or in the framework regions or in both. In a further embodiment at least 1 CDR is mutated to human germline sequence, or at least 2 CDR's are mutated or at least 3 CDR's are mutated, or at least 4 CDR's are mutated.

In yet another embodiment at least 5 residues are mutated to human germline sequence, or at least 7 residues, or at least 10 residues or at least 15 residues or at least 20 residues or at least 40 residues or at least 60 residues are mutated to human germline sequence.

In yet another embodiment of the methods described herein the residues of the antibody involved directly with binding to the antigen are determined to between about 2-5 Å, or between about 3-5 Å or between about 3-4 Å or at about 3.5 Å.

In yet a further embodiment of the methods described herein there is provided an antibody obtainable by such a method.

DEFINITIONS

The term "antigen binding protein" as used herein refers to antibodies, antibody fragments and other protein constructs which are capable of binding to and neutralising human OSM.

The terms Fv, Fc, Fd, Fab, or F(ab)2 are used with their standard meanings (see, e.g., Harlow et al., Antibodies A Laboratory Manual, Cold Spring Harbor Laboratory, (1988)).

The term "antibody" is used herein in the broadest sense and specifically covers monoclonal antibodies (including full length monoclonal antibodies), polyclonal antibodies, multispecific antibodies (e.g. bispecific antibodies)

The term "monoclonal antibody" as used herein refers to an antibody obtained from a population of substantially homogenous antibodies i.e. the individual antibodies comprising the population are identical except for possible naturally occurring mutations that may be present in minor amounts. Monoclonal antibodies are highly specific being directed against a single antigenic binding site. Furthermore, in contrast to polyclonal antibody preparations which typically include different antibodies directed against different determinants (epitopes), each monoclonal antibody is directed against a single determinant on the antigen.

A "chimeric antibody" refers to a type of engineered antibody in which a portion of the heavy and/or light chain is identical with or homologous to corresponding sequences in antibodies derived from a particular donor antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al. *Proc. Natl. Acad. Sci. USA* 81:6851-6855) (1984)).

A "humanised antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

"Identity," means, for polynucleotides and polypeptides, as the case may be, the comparison calculated using an algorithm provided in (1) and (2) below:

(1) Identity for polynucleotides is calculated by multiplying the total number of nucleotides in a given sequence by the integer defining the percent identity divided by 100 and then subtracting that product from said total number of nucleotides in said sequence, or:

$$nn \leq xn - (xn \cdot y),$$

wherein nn is the number of nucleotide alterations, xn is the total number of nucleotides in a given sequence, y is 0.95 for 95%, 0.97 for 97% or 1.00 for 100%, and · is the symbol for the multiplication operator, and wherein any non-integer product of xn and y is rounded down to the nearest integer prior to subtracting it from xn. Alterations of a polynucleotide sequence encoding a polypeptide may create nonsense, missense or frameshift mutations in this coding sequence and thereby alter the polypeptide encoded by the polynucleotide following such alterations.

(2) Identity for polypeptides is calculated by multiplying the total number of amino acids by the integer defining the percent identity divided by 100 and then subtracting that product from said total number of amino acids, or:

$$na \leq xa - (xa \cdot y),$$

wherein na is the number of amino acid alterations, xa is the total number of amino acids in the sequence, y is 0.95 for 95%, 0.97 for 97% or 1.00 for 100%, and · is the symbol for the multiplication operator, and wherein any non-integer product of xa and y is rounded down to the nearest integer prior to subtracting it from xa.

"Isolated" means altered "by the hand of man" from its natural state, has been changed or removed from its original environment, or both. For example, a polynucleotide or a polypeptide naturally present in a living organism is not "isolated," but the same polynucleotide or polypeptide separated from the coexisting materials of its natural state is "isolated", including but not limited to when such polynucleotide or polypeptide is introduced back into a cell, even if the cell is of the same species or type as that from which the polynucleotide or polypeptide was separated.

Throughout the present specification and the accompanying claims the term "comprising" and "comprises" incorporates "consisting of" and "consists of". That is, these words are intended to convey the possible inclusion of other elements or integers not specifically recited, where the context allows.

The term "specifically binds" as used throughout the present specification in relation to antigen binding proteins of the invention means that the antigen binding protein binds human OSM (hOSM) with no or insignificant binding to other human proteins. The term however does not exclude the fact that antigen binding proteins of the invention may also be cross-reactive with other forms of OSM, for example primate OSM.

The term "directly interact" as used throughout this specification in relation to antigen binding proteins of the invention means that when the antigen binding protein is bound to human OSM (hOSM) that specific residues on the antigen binding protein are within 3.5 Å of specific residues on the hOSM.

The term inhibits as used throughout the present specification in relation to antigen binding proteins of the invention means that the biological activity of OSM is reduced in the presence of the antigen binding proteins of the present invention in comparison to the activity of OSM in the absence of such antigen binding proteins. Inhibition may be due but not limited to one or more of blocking ligand binding, preventing the ligand activating the receptor, down regulating the OSM or affecting effector functionality. The antibodies of the invention may neutralise OSM. Levels of neutralisation can be measured in several ways, for example by use of the assays as set out in the examples below, for example in 2.2.1 in a KB Cell Neutralisation Assay. OSM is able to induce Interleukin 6 release from KB cells via signalling through the Gp130/OSMR complex. The neutralisation of OSM in this assay is measured by assessing the ability of anti-OSM monoclonal antibodies to inhibit IL6 production.

If an antibody or antigen binding fragment thereof is capable of neutralisation then this is indicative of inhibition of the interaction between human OSM and its gp130 receptor. Antibodies which are considered to have neutralising activity against human OSM would have an IC50 of less than 10 micrograms/ml, or less than 5 micrograms/ml, or less than 2 micrograms/ml, or less than 1 micrograms/ml or less than 0.1 micrograms/ml in the KB cell neutralisation assay as set out in Example 2.2.1

"CDRs" are defined as the complementarity determining region amino acid sequences of an antibody which are the hypervariable domains of immunoglobulin heavy and light chains. There are three heavy chain and three light chain CDRs (or CDR regions) in the variable portion of an immunoglobulin. Thus, "CDRs" as used herein may refer to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The CDR sequences of antibodies can be determined by the Kabat numbering system (Kabat et al; (Sequences of proteins of Immunological Interest NIH, 1987), alternatively they can be determined using the Chothia numbering system (Al-Lazikani et al., (1997) JMB 273, 927-948), the contact definition method (MacCallum R. M., and Martin A. C. R. and Thornton J. M, (1996), Journal of Molecular Biology, 262 (5), 732-745) or any other established method for numbering the residues in an antibody and determining CDRs known to the skilled man in the art Other numbering conventions for CDR sequences available to a skilled person include "AbM"

(University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

| | Kabat CDR | Chothia CDR | AbM CDR | Contact CDR | Minimum binding unit |
|---|---|---|---|---|---|
| H1 | 31-35/ 35A/35B | 26-32/ 33/34 | 26-35/ 35A/35B | 30-35/ 35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3" follow the Kabat numbering system as set forth in Kabat et al; Sequences of proteins of Immunological Interest NIH, 1987.

The terms "VH" and "VL" are used herein to refer to the heavy chain variable domain and light chain variable domain respectively of an antibody.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, VHH, VL) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are still considered to be "domain antibodies" according to the invention. As used herein "VH includes camelid VHH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), US7250297B1 and US20070224633

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem. 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

As used herein, the term "antigen-binding site" refers to a site on a protein which is capable of specifically binding to antigen, this may be a single domain, for example an epitope-binding domain, or it may be paired VH/VL domains as can be found on a standard antibody. In some embodiments of the invention single-chain Fv (ScFv) domains can provide antigen-binding sites.

The terms "mAbdAb" and dAbmAb" are used herein to refer to antigen-binding proteins of the present invention. The two terms can be used interchangeably, and are intended to have the same meaning as used herein.

The term "antigen binding protein" as used herein refers to antibodies, antibody fragments for example a domain antibody (dAb), ScFv, FAb, FAb2, and other protein constructs. Antigen binding molecules may comprise at least one Ig variable domain, for example antibodies, domain antibodies (dAbs), Fab, Fab', F(ab')2, Fv, ScFv, diabodies, mAbdAbs, affibodies, heteroconjugate antibodies or bispecific antibodies. In one embodiment the antigen binding molecule is an antibody. In another embodiment the antigen binding molecule is a dAb, i.e. an immunoglobulin single variable domain such as a VH, VHH or VL that specifically binds an antigen or epitope independently of a different V region or domain. Antigen binding molecules may be capable of binding to two targets, i.e. they may be dual targeting proteins. Antigen binding molecules may be a combination of antibodies and antigen binding fragments such as for example, one or more domain antibodies and/or one or more ScFvs linked to a monoclonal antibody. Antigen binding molecules may also comprise a non-Ig domain for example a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to OSM. As used herein "antigen binding protein" will be capable of antagonising and/or neutralising human OSM. In addition, an antigen binding protein may inhibit and or block OSM activity by binding to OSM and preventing a natural ligand from binding and/or activating the gp130 receptor.

The term "Effector Function" as used herein is meant to refer to one or more of Antibody dependant cell mediated cytotoxic activity (ADCC), Complement-dependant cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antigen binding protein bound to antigen and the formation of the Fc/Fcγ complex induces a range of effects including cytotoxicity, immune cell activation, phagocytosis and release of inflammatory cytokines.

The interaction between the constant region of an antigen binding protein and various Fc receptors (FcR) is believed to mediate the effector functions of the antigen binding protein. Significant biological effects can be a consequence of effector functionality, in particular, antibody-dependent cellular cytotoxicity (ADCC), fixation of complement (complement dependent cytotoxicity or CDC), and half-life/clearance of the antigen binding protein. Usually, the ability to mediate effector function requires binding of the antigen binding protein to an antigen and not all antigen binding proteins will mediate every effector function.

Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p6591-6604; Chappel et al, 1993 The Journal of Biological Chemistry, Vol 268, p25124-25131; Lazar et al, 2006 PNAS, 103; 4005-4010. Examples of assays to determine CDC function include that described in 1995 J Imm Meth 184:29-38.

Some isotypes of human constant regions, in particular IgG4 and IgG2 isotypes, essentially lack the functions of a) activation of complement by the classical pathway; and b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

In one embodiment of the present invention there is provided an antigen binding protein comprising a constant region such that the antigen binding protein has reduced ADCC and/or complement activation or effector functionality. In one such embodiment the heavy chain constant region may comprise a naturally disabled constant region of IgG2 or IgG4 isotype or a mutated IgG1 constant region. Examples of suitable modifications are described in EP0307434. One example comprises the substitutions of alanine residues at positions 235 and 237 (EU index numbering).

Human IgG1 constant regions containing specific mutations or altered glycosylation on residue Asn297 have also been described to enhance binding to Fc receptors. In some cases these mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment the antigen binding protein of the invention herein described is mutated at positions 239 and 332, for example S239D and I332E or in a further embodiment it is mutated at three or more positions selected from 239 and 332 and 330, for example S239D and I332E and A330L. (EU index numbering).

In an alternative embodiment of the present invention, there is provided an antigen binding protein comprising a heavy chain constant region with an altered glycosylation profile such that the antigen binding protein has enhanced effector function. For example, wherein the antigen binding protein has enhanced ADCC or enhanced CDC or wherein it has both enhanced ADCC and CDC effector function. Examples of suitable methodologies to produce antigen binding proteins with an altered glycosylation profile are described in WO2003011878, WO2006014679 and EP1229125, all of which can be applied to the antigen binding proteins of the present invention.

The present invention also provides a method for the production of an antigen binding protein according to the invention comprising the steps of:
a) culturing a recombinant host cell comprising an expression vector comprising the isolated nucleic acid as described herein, wherein the FUT8 gene encoding alpha-1,6-fucosyltransferase has been inactivated in the recombinant host cell; and
b) recovering the antigen binding protein.

Such methods for the production of antigen binding proteins can be performed, for example, using the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. No. 7,214,775, U.S. Pat. No. 6,946,292, WO0061739 and WO0231240 all of which are incorporated herein by reference. Those of ordinary skill in the art will also recognize other appropriate systems.

In one embodiment of the present invention there is provided an antigen binding protein comprising a chimaeric heavy chain constant region for example an antigen binding protein comprising a chimaeric heavy chain constant region with at least one CH2 domain from IgG3 such that the antigen binding protein has enhanced effector function, for example wherein it has enhanced ADCC or enhanced CDC, or enhanced ADCC and CDC functions. In one such embodiment, the antigen binding protein may comprise one CH2 domain from IgG3 or both CH2 domains may be from IgG3.

Also provided is a method of producing an antigen binding protein according to the invention comprising the steps of:
a) culturing a recombinant host cell comprising an expression vector comprising an isolated nucleic acid as described herein wherein the expression vector comprises a nucleic acid sequence encoding an Fc domain having both IgG1 and IgG3 Fc domain amino acid residues; and
b) recovering the antigen binding protein.

Such methods for the production of antigen binding proteins can be performed, for example, using the COMPLEGENT™ technology system available from BioWa, Inc. (Princeton, N.J.) and Kyowa Hakko Kogyo (now, Kyowa Hakko Kirin Co., Ltd.) Co., Ltd. in which a recombinant host cell comprising an expression vector in which a nucleic acid sequence encoding a chimeric Fc domain having both IgG1 and IgG3 Fc domain amino acid residues is expressed to produce an antigen binding protein having enhanced complement dependent cytotoxicity (CDC) activity that is increased relative to an otherwise identical antigen binding protein lacking such a chimeric Fc domain. Aspects of the COMPLEGENT™ technology system are described in WO2007011041 and US20070148165 each of which are incorporated herein by reference. In an alternative embodiment CDC activity may be increased by introducing sequence specific mutations into the Fc region of an IgG chain. Those of ordinary skill in the art will also recognize other appropriate systems.

It will be apparent to those skilled in the art that such modifications may not only be used alone but may be used in combination with each other in order to further enhance effector function.

In one such embodiment of the present invention there is provided an antigen binding protein comprising a heavy chain constant region which comprises a mutated and chimaeric heavy chain constant region for example wherein an antigen binding protein comprising at least one CH2 domain from IgG3 and one CH2 domain from IgG1, wherein the IgG1 CH2 domain has one or more mutations at positions selected from 239 and 332 and 330 (for example the mutations may be selected from S239D and I332E and A330L) such that the antigen binding protein has enhanced effector function, for example wherein it has one or more of the following functions, enhanced ADCC or enhanced CDC, for example wherein it has enhanced ADCC and enhanced CDC. In one embodiment the IgG1 CH2 domain has the mutations S239D and I332E.

In an alternative embodiment of the present invention there is provided an antigen binding protein comprising a chimaeric heavy chain constant region and which has an altered glycosylation profile. In one such embodiment the heavy chain constant region comprises at least one CH2 domain from IgG3 and one CH2 domain from IgG1 and has an altered glycosylation profile such that the ratio of fucose to mannose is 0.8:3 or less, for example wherein the antigen binding protein is defucosylated so that said antigen binding protein has an enhanced effector function in comparison with an equivalent antigen binding protein with an immunoglobulin heavy chain constant region lacking said mutations and altered glycosylation profile, for example wherein it has one or more of the following functions, enhanced ADCC or enhanced CDC, for example wherein it has enhanced ADCC and enhanced CDC In an alternative embodiment the antigen binding protein has at least one IgG3 CH2 domain and at least one heavy chain constant domain from IgG1 wherein both IgG CH2 domains are mutated in accordance with the limitations described herein.

In one aspect of the invention there is provided a method of producing an antigen binding protein according to the invention described herein comprising the steps of:
a) culturing a recombinant host cell containing an expression vector containing an isolated nucleic acid as described herein, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and
b) recovering the antigen binding protein.

Such methods for the production of antigen binding proteins can be performed, for example, using the ACCRETAMAB™ technology system available from BioWa, Inc. (Princeton, N.J.) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain and which has fucose on the oligosaccharide In yet another embodiment of the present invention there is an antigen binding protein comprising a mutated and chimeric heavy chain constant region wherein said antigen binding protein has an altered glycosylation profile such that the antigen binding protein has enhanced effector function, for example wherein it has one or more of the following functions, enhanced ADCC or enhanced CDC. In one embodiment the mutations are selected from positions 239 and 332 and 330, for example the mutations are selected from S239D and I332E and A330L. In a further embodiment the heavy chain constant region comprises at least one CH2 domain from IgG3 and one Ch2 domain from IgG1. In one embodiment the heavy chain constant region has an altered glycosylation profile such that the ratio of fucose to mannose is 0.8:3 or less for example the antigen binding protein is defucosylated, so that said antigen binding protein has an enhanced effector function in comparison with an equivalent non-chimaeric antigen binding protein or with an immunoglobulin heavy chain constant region lacking said mutations and altered glycosylation profile.

Another means of modifying antigen binding proteins of the present invention involves increasing the in-vivo half life of such proteins by modification of the immunoglobulin constant domain or FcRn (Fc receptor neonate) binding domain.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells, and if they bind to FcRn, are recycled out into circulation. In contrast, IgG molecules that do not bind to FcRn enter the cells and are targeted to the lysosomal pathway where they are degraded.

The neonatal FcRn receptor is believed to be involved in both antibody clearance and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435. Switches at any of these positions described in this section may enable increased serum half-life and/or altered effector properties of antigen binding proteins of the invention.

Antigen binding proteins of the present invention may have amino acid modifications that increase the affinity of the constant domain or fragment thereof for FcRn. Increasing the half-life of therapeutic and diagnostic IgG's and other bioactive molecules has many benefits including reducing the amount and/or frequency of dosing of these molecules. In one embodiment there is therefore provided an antigen binding according to the invention provided herein or a fusion protein comprising all or a portion (an FcRn binding portion) of an IgG constant domain having one or more of these amino acid modifications and a non-IgG protein or non-protein molecule conjugated to such a modified IgG constant domain, wherein the presence of the modified IgG constant domain increases the in vivo half life of the antigen binding protein.

PCT Publication No. WO 00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region, wherein the numbering of the residues in the Fc region is that of the EU index (Kabat et al).

PCT Publication No. WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

Shields et al. (2001, J Biol Chem; 276:6591-604) used alanine scanning mutagenesis to alter residues in the Fc region of a human IgG1 antibody and then assessed the binding to human FcRn.

Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect was found for combination variants with improved binding to FcRn. At pH 6.0, the E380A/N434A variant showed over 8-fold better binding to FcRn, relative to native IgG1, compared with 2-fold for E380A and 3.5-fold for N434A. Adding T307A to this effected a 12-fold improvement in binding relative to native IgG1. In one embodiment the antigen binding protein of the invention comprises the E380A/N434A mutations and has increased binding to FcRn.

Dall'Acqua et al. (2002, J. Immunol.; 169:5171-80) described random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur in substituting residues located in a band across the Fc-FcRn interface (M252, S254, T256, H433, N434, and Y436) and to lesser extend substitutions of residues at the periphery like V308, L309, Q311, G385, Q386, P387, and N389. The variant with the highest affinity to human FcRn was obtained by combining the M252Y/S254T/T256E and H433K/N434F/Y436H mutations and exhibited a 57-fold increase in affinity relative to the wild-type IgG1. The in vivo behaviour of such a mutated human IgG1 exhibited a nearly 4-fold increase in serum half-life in cynomolgus monkey as compared to wild-type IgG1.

The present invention therefore provides a variant of an antigen binding protein with optimized binding to FcRn. In a preferred embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat.

In a further aspect of the invention the modifications are M252Y/S254T/T256E.

Additionally, various publications describe methods for obtaining physiologically active molecules whose half-lives are modified either by introducing an FcRn-binding polypeptide into the molecules (WO 97/43316; U.S. Pat. No. 5,869, 046; U.S. Pat. No. 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039).

Additionally, methods of producing an antigen binding protein with a decreased biological half-life are also provided. A variant IgG in which His435 is mutated to alanine results in the selective loss of FcRn binding and a significantly reduced serum half-life (Firan et al. 2001, International immunology 13:993). U.S. Pat. No. 6,165,745 discloses a method of producing an antigen binding protein with a decreased biological half-life by introducing a mutation into the DNA segment encoding the antigen binding protein. The mutation includes an amino acid substitution at position 253, 310, 311, 433, or 434 of the Fc-hinge domain.

The term "Non Human antibody or antibody fragment thereof" as used herein is meant to refer to antibodies or fragments thereof which originate from any species other than human wherein human includes chimeric antibodies.

The term "donor antibody" refers to an antibody (monoclonal, and/or recombinant) which contributes the amino acid sequences of its variable domains, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. The human antibody is the acceptor antibody. The term "Human acceptor sequence" as used herein is meant to refer to a framework of an antibody or antibody fragment thereof comprising the amino acid sequence of a VH or VL framework derived from a human antibody or antibody fragment thereof or a human consensus sequence framework into which CDR's from a non-human species may be incorporated.

The term "incorporation" of CDR's or hypervariable regions as used herein encompasses any means by which the non-human CDR's are situated with the human acceptor framework. It will be appreciated that this can be achieved in various ways, for example, nucleic acids encoding the desired amino acid sequence can be generated by mutating nucleic acids encoding the non-human variable domain sequence so that the framework residues thereof are changed to human acceptor framework residues, or by mutating nucleic acid encoding the human variable domain sequence so that the CDR's are changed to non-human residues, or by synthesizing nucleic acids encoding the desired sequence. In one embodiment the final sequence is generated in silico.

The present invention is now described by way of example only. The appended claims may include a generalisation of one of more of the following examples.

EXAMPLES

Example 1

Monoclonal Antibody Generation and Selection 1.1 Immunisation Strategy

The anti human OSM mAb S168110G08(1)1A09 ("10G8") was identified from hybridomas derived from mice immunized with recombinant glycosylated human OSM (K598). Female SJL mice (n=2, Harlan, U K, HOST SP06-06031) were immunised conventionally using a total of 10 µg protein intraperitoneally with AS02-like adjuvant. Booster immunisations were with 5 µg protein. Test bleeds were taken following each booster and the mouse with the best response (168#4) was chosen for hybridoma fusion (R16092/177-198). The spleen was excised, disrupted and a PEG1500 induced somatic cell fusion performed with mouse myeloma cells X63 AG8 653.GFP.Bcl-2.11 (BioCat 112754; R17209/58). The fusion was plated out into 10×96 well plates and 5 Nunc Omnitrays in methylcellulose containing semi-solid medium. Colonies were picked from the semi-solid media into 5×96 well plates.

1.2 Screening Strategy 1.2.1 Primary Screen

The primary screen for the Anti-OSM back-up antibodies was based on selecting hybridoma material capable of binding human OSM and, in order to select for Anti-Site II molecules, inhibiting both human and cynomolgus OSM from binding the gp130 receptor. Positive hybridoma supernatants from these screens were analysed by BIACore off-rate kinetics to select the top binding hybridomas.

In excess of 3000 clones were recovered from fusions, 86 of which showed appreciable binding to human OSM by binding ELISA. Analysis for anti-Site II activity was performed on positive hybridomas by gp130 ELISA with human and cynomolgus OSM, Hybridoma clones which inhibited both human and cynomolgus OSM from binding to human gp13 were subjected to BIACore off-rate kinetic analysis. The top four human OSM binders by off-rate analysis, 10G8, 9G2, 3E3 and 2B7, were monocloned and re-screened. There was no difference in BIACore and ELISA binding activity or gp130 inhibition between the monoclones from each hybridoma. The daughter clones: 10G8.A9, 9G2.C1, 2B7.A6 and 3E3.A1 were cryopreserved and used for serum free scale-up and purification. These were progressed into secondary screening.

1.2.2 Secondary Screen

Secondary screening to rank the four daughter clones, 10G8/A9, 9G2/C1, 2B7/A6 and 3E3/A1, included BIACore kinetic analysis against human/cynomolgus OSM; Human gp130 ELISA with human/cynomolgus OSM; KB cell neutralisation assay with human/cynomolgus OSM. In addition to this, the ability to neutralise endogenous, neutrophil-derived human OSM, retain neutralisation ability in 25% human AB serum and reactivity against human LIF was assessed.

BIACore Analysis:

BIACore analysis demonstrated that 10G8, 9G2, 3E3 and 2B7 had higher affinities for human OSM than an alternative non-competitive anti-OSM mouse antibody (15E10) (Table 1). 10G8 showed the greatest affinity for both human (~550 pM) and cynomolgus (~310 pM) OSM. Compared with 15E10, 10G8 had an 8-fold/0.9 log increased affinity for human and an 11-fold/1 log increased affinity for cynomolgus OSM. Both 10G8 and 9G2 exhibited an increased affinity for cynomolgus OSM over human OSM.

TABLE 1

BIACore Kinetics - Four anti-OSM back-up lead antibodies 10G8, 9G2, 3E3 and 2B7 compared with 15E10.

| mAb | OSM | ka (on rate) | kd (off-rate) | KD nM |
|---|---|---|---|---|
| 10G8 | Human | 1.12E+05 | 6.14E−05 | 0.55 |
|  | Cyno | 9.69E+04 | 2.99E−05 | 0.308 |
| 9G2 | Human | 7.52E+04 | 1.21E−04 | 1.60 |
|  | Cyno | 6.14E+04 | 4.76E−05 | 0.75 |

TABLE 1-continued

BIACore Kinetics - Four anti-OSM back-up lead antibodies 10G8, 9G2, 3E3 and 2B7 compared with 15E10.

| mAb | OSM | ka (on rate) | kd (off-rate) | KD nM |
|---|---|---|---|---|
| 3E3 | Human | 1.95E+05 | 2.53E−04 | 1.30 |
|  | Cyno | 1.71E+05 | 5.60E−04 | 3.28 |
| 2B7 | Human | 1.21E+05 | 2.54E−04 | 2.09 |
|  | Cyno | 1.00E+05 | 9.33E−04 | 9.31 |
| 15E10 | Human | 1.94E+05 | 8.69E−04 | 4.48 |
|  | Cyno | 1.77E+05 | 5.97E−04 | 3.37 |

Human gp130 ELISA:

The human gp130 ELISA uses relatively high levels of OSM (25 ng/ml), reducing its ability to separate high affinity from lower affinity antibodies as the ligand is in excess. Following four repeats of this assay, 10G8 was shown to be the most potent antibody in blocking both human and cynomolgus OSM from binding to gp130 receptor in this assay (FIG. 1; Table 2).

TABLE 2

Human gp130 ELISA - Summary of four repeats of the human gp130 ELISA to rank 10G8, 9G2, 3E3 and 2B7 activity against human and cynomolgus OSM. A non-competitive mouse antibody 15E10 and a negative control tool antibody were added for comparison purposes.

| Human OSM Ranking | Antibody | Human OSM Mean IC50 µg/ml ± SD | Cynomolgus OSM Mean IC50 µg/ml ± SD (Cyno OSM ranking) |
|---|---|---|---|
| 1 | 10G8 | 0.06 ± 0.01 (400 pM) | 0.01 ± 0.00 (1) (40 pM) |
| 2 | 2B7 | 0.08 ± 0.02 (533 pM) | 0.14 ± 0.04 (6) (993 pM) |
| 3 | 9G2 | 0.16 ± 0.04 (1.1 nM) | 0.03 ± 0.04 (4) (200 pM) |
| 4 | 15E10 | 0.19 ± 0.07 (1.3 nM) | 0.03 ± 0.05 (3) (200 pM) |
| 5 | 3E3 | 0.19 ± 0.04 (1.3 nM) | 0.06 ± 0.07 (5) (400 pM) |

The human gp130 assay was repeated in the presence of 25% human AB serum. Two repeats of this assay showed that all four lead antibodies 10G8, 9G2, 3E3 and 2B7, along with 15E10, retained their ability to block human and cynomolgus OSM from binding to gp130 (Data not shown).

KB Cell Neutralisation Assay:

OSM induces IL-6 release from KB cells (a human epithelial cell line expressing mRNA for gp130 and OSM receptors). Breifly KB cells are stimulated with 1 ng/ml OSM+/− different antibody concentrations for 16-18 hours at 37° C. and IL6 release monitored by ELISA. The KB cell neutralisation assay uses a reduced amount of OSM compared with the gp130 assay (1 ng/ml versus 25 ng/ml). This makes it a more discriminating assay for separating high affinity from low affinity neutralisers. Compared with Antibody 15E10, 10G8 was 15-fold/1.2 log more potent against human OSM in the KB cell neutralisation assay. From three repeats of the assay, 10G8 ranked first in all repeats, giving a mean IC50 value of 8 ng/ml against human OSM and 6 ng/ml against cynomolgus (FIG. 2; Table 3). 9G2 ranked second in this assay with an IC50 of 18 ng/ml and 15 ng/ml against human and cynomolgus OSM respectively.

TABLE 3

KB Cell Neutralisation Assay - Summary of three repeats of the KB cell neutralisation assay to rank 10G8, 9G2, 3E3 and 2B7 activity against human and cynomolgus OSM. Antibody 15E10 was added for comparison purposes. The tool antibody was used as a negative control.

| Human OSM Ranking | Antibody | Human OSM Mean IC50 µg/ml ± SD | Cynomolgus OSM Mean IC50 µg/ml ± SD (Cyno OSM ranking) |
|---|---|---|---|
| 1 | 10G8 | 0.008 ± 0.003 (53 pM) | 0.006 ± 0.002 (1) (40 pM) |
| 2 | 9G2 | 0.018 ± 0.008 (120 pM) | 0.015 ± 0.006 (2) (100 pM) |
| 3 | 2B7 | 0.049 ± 0.003 (327 pM) | 0.344 ± 0.186 (6) (2.3 nM) |
| 4 | 3E3 | 0.054 ± 0.034 (360 pM) | 0.150 ± 0.013 (5) (1 nM) |
| 6 | 15E10 | 0.279 ± 0.161 (1.9 nM) | 0.035 ± 0.013 (4) (233 pM) |

In the presence of 25% human AB serum, 10G8, 9G2 and 3E3 retained their ability to neutralise both human and cynomolgus OSM (FIG. 3). 15E10 and 2B7 failed to produce fitted curves of sufficient quality to calculate IC50 values. As with the non-human serum KB cell assay, the most potent antibody was 10G8 with 9G2 ranking second. Some drop-off in activity was seen in the presence of 25% AB serum. To some extent this may be due to the AB serum interfering with this assay readout. Higher IL-6 background levels were observed in this assay than in the non-human serum.

Endogenous Human OSM (gp130 Assay):

All four lead antibodies, 10G8, 9G2, 3E3 and 2B7, as well as Antibody 15E10, inhibited endogenous human OSM from four separate donors (FIG. 4). This native OSM was generated from GM-CSF-stimulation of healthy human neutrophils.

Human LIF Reactivity (KB Cell Neutralisation Assay):

Human LIF is the closest related member of the IL-6 family to human OSM. Initial studies showed that there was no reactivity between 10G8, 9G2, 3E3 and 2B7 and human LIF, indicating that these antibodies are OSM-specific (FIG. 5).

Marmoset OSM Reactivity (KB Cell Neutralisation Assay):

All four lead molecules 10G8, 9G2, 3E3 and 2B7 were shown to neutralise marmoset OSM in the KB cell neutralisation assay (FIG. 6). 15E10 and a panel of three additional anti-human OSM antibodies, 10D3DLE, OM4.11.17 and OM4.11.31, also failed to neutralise marmoset OSM.

From two assay repeats, 10G8 was the most potent neutraliser of marmoset OSM, with 9G2 being ranked second.

1.2.3 Monoclonals Selected for Progression

From the four antibodies, 10G8 was chosen as the lead antibody for chimaerisation based on it ranking first in all of the assays listed above. 9G2 was also selected for chimaerisation as a back-up molecule in the case of difficulties in humanisation.

1.3 Antibody Engineering and Lead Antibody Series Selection

1.3.2 Variable Region Sequences

The variable genes for the four selected monoclonals, 2B7, 3E3, 9G2 and 10G8 were isolated and sequenced in parallel to allow generation of the corresponding chimaeric antibodies. Total RNA was extracted from the hybridoma cell pellets. Heavy and light chain V-gene coding sequences were amplified by either RT-PCR or 5'RACE and then TA cloned for sequence analysis. V-gene amplification was carried out in duplicate for each antibody to enable subsequent verification of the correct sequences from two independent reactions. Sequence of the variable heavy and variable light chains was obtained for all 4 hybridoma clones. Alignment of the protein sequences showed that the antibodies had a high degree of sequence identity in the both the variable heavy and light chain regions (FIGS. 7 & 8). The sequences of the heavy and light chain variable regions of these antibodies are set out in SEQ ID NO. 26-48. See Table A.

Sequence comparison between the four lead monoclonals and Antibody 15E10 show only 50-60% identity with either the light (FIG. 9) or the heavy (FIG. 10) chains. This indicates that these antibodies bind epitopes distinct from those recognised by Antibody 15E10.

1.3.3 Antibody Cloning

1.3.3.1 Construction of Chimaera

Both 10G8 and 9G2 were generated as chimaeric antibodies by grafting the mouse VH and VL regions described above onto codon optimised human gamma 1 Fc wild type and human kappa constant regions respectively. The chimaeric antibodies are used to confirm functionality of the cloned mouse V-regions and were purified and used as a reference when testing humanized constructs. PCR primers were designed based on the 5' and 3' DNA sequences determined in 2.3.1 to include restriction sites required for cloning into the Rlx and pTT5 mammalian expression vectors. Primers were also designed to replace the native signal sequence with the Campath signal sequence. Hind III and Spe I sites were designed to frame the $V_H$ domain and allow cloning into a modified Rld or pTT5 vector containing the human γ1 C region. The introduction of a Spe I site into the framework 4 sequence resulted in a single amino acid change in FR4 at position 108. For the 9G2 VH region, an internal SpeI site was present at the 5'-end of the DNA sequence, the PCR primer for the 9G2 chimera was designed to remove this internal SpeI site. Hind III and BsiWI sites were designed to frame the $V_L$ domain and allow cloning into a modified Rln or pTT5 vector containing the human κ C region.

Clones with the correct $V_H$ and $V_L$ sequences were identified and plasmids prepared for expression in CHO or HEK cells.

1.3.3.2 Expression of Chimaera

The Rld and Rln plasmids encoding chimaeric 10G8 and 9G2 $V_H$ and $V_L$ domains, respectively were co-transfected into CHOE1A cells by electroporation and expressed in a polyclonal cell culture. The pTT plasmids encoding the chimaeric 10G8 and 9G2 $V_H$ and $V_L$ domains were co-transfected into HEK293 cells using lipid transfection methodology to allow transient episomal expression, transfection in the episomal expression system can potentially yield mg quantities of antibody. The chimaeric antibodies (10G8c and 9G2c) produced were purified from the cell culture supernatants by affinity chromatography on Protein A Sepharose. Purified antibodies were QCed by SDS-PAGE analysis and size exclusion chromatography.

1.3.3.3 Binding Assay Data

Human OSM Binding ELISA:

Both the 10G8 and 9G2 chimaeras successfully bound to human OSM, to a greater extent than 15E10 chimera (15E10c) (FIG. 11). This was a direct ELISA where human OSM was coated at 1 μg/ml and bound antibodies detected using anti-human IgG.

BIACore Analysis:

BIACore analysis showed that there was little or no loss in human or cynomolgus OSM binding in the chimaeric 10G8 and 9G2 molecules compared with the mouse parental antibodies (Table 4). 10G8 chimaera ranks first (654 μM), ahead of 9G2 chimaera (1.33 nM). All antibodies exhibited an increased affinity for cynomolgus OSM over human OSM.

TABLE 4

BIACore Kinetics - Binding kinetics of 10G8, 10G8 Chimaera, 9G2 & 9G2 Chimaera antibodies.

|  | Cyno OSM | | | Human OSM | | |
| --- | --- | --- | --- | --- | --- | --- |
|  | Ka (M−1·s−1) | Kd (s−1) | KD (nM) | Ka (M−1·s−1) | Kd (s−1) | KD (nM) |
| 10G8 chimera | 2.37E+5 | 1.14E−4 | 0.480 | 2.33E+5 | 1.52E−4 | 0.654 |
| Mouse 10G8 | 9.69e+4 | 2.99e−5 | 0.308 | 1.12e+5 | 6.14e−5 | 0.549 |
| 9G2 chimera | 1.27E+5 | 9.99E−5 | 0.787 | 1.26E+5 | 1.68E−4 | 1.333 |
| Mouse 9G2 | 6.14e+4 | 4.76e−5 | 0.775 | 7.52e+4 | 1.21e−4 | 1.60 |

1.3.3.4 Functional Assay Data

Human gp130 ELISA:

The human gp130 ELISA uses relatively high levels of OSM (25 ng/ml), reducing its ability to separate high affinity from lower affinity antibodies as the ligand is in excess. Following three repeats of this assay, the 10G8 chimaera was the most effective antibody at inhibiting both human and cynomolgus OSM from binding to gp130 receptor. Values for 10G8 mouse parental and 10G8 chimaera were very similar in this assay (FIG. 12; Table 5). There was no significant difference between 9G2 and its chimaera.

TABLE 5

Human gp130 ELISA - Summary of three repeats of the human gp130 ELISA to rank 10G8, 10G8 Chimaera, 9G2 & 9G2 Chimaera activity against human and cynomolgus OSM. Antibody 15E10 was added for comparison purposes. A tool antibody was used as a negative control.

| Human OSM Ranking | Antibody | Human OSM Mean IC50 μg/ml ± SD | Cynomolgus OSM Mean IC50 μg/ml ± SD (Cyno OSM ranking) |
| --- | --- | --- | --- |
| 1 | 10G8Chimaera | 0.037 ± 0.035 (247 pM) | 0.016 ± 0.015 (1) (107 pM) |
| 2 | 9G2 | 0.038 ± 0.004 (253 pM) | 0.049 ± 0.059 (5) (327 pM) |
| 3 | 10G8 | 0.044 ± 0.034 (293 pM) | 0.017 ± 0.013 (2) (113 pM) |

TABLE 5-continued

Human gp130 ELISA - Summary of three repeats of the human gp130 ELISA to rank 10G8, 10G8 Chimaera, 9G2 & 9G2 Chimaera activity against human and cynomolgus OSM. Antibody 15E10 was added for comparison purposes. A tool antibody was used as a negative control.

| Human OSM Ranking | Antibody | Human OSM Mean IC50 µg/ml ± SD | Cynomolgus OSM Mean IC50 µg/ml ± SD (Cyno OSM ranking) |
| --- | --- | --- | --- |
| 4 | 9G2Chimaera | 0.078 ± 0.102 (520 pM) | 0.028 ± 0.033 (3) (187 pM) |
| 5 | 15E10 | 0.250 ± 0.403 (1.7 nM) | 0.071 ± 0.096 (6) (473 pM) |

The human gp130 assay was repeated in the presence of human AB serum for both human and cynomolgus OSM. All molecules retained their activity in 25% serum. Against human and cynomolgus OSM, 10G8 chimaera and 10G8 mouse parental ranked first and second respectively. 1050 values for these two antibodies were similar. No significant difference was observed between the 9G2 chimaera, ranked third, and its mouse parental (Data not shown).

KB Cell Neutralisation Assay:

The 10G8 mouse parental behaved similarly to the chimaera (FIG. 13; Table 6). 9G2 mouse parental and chimaera ranked third and fourth, respectively, in this assay.

TABLE 6

KB Cell Neutralisation Assay - Summary of three repeats of the KB cell neutralisation assay to rank 10G8, 10G8 Chimaera, 9G2 & 9G2 Chimaera activity against human and cynomolgus OSM. Antibody 15E10 was added for comparison purposes. A tool antibody was used as a negative control.

| Human OSM Ranking | Antibody | Human OSM Mean IC50 µg/ml ± SD | Cynomolgus OSM Mean IC50 µg/ml ± SD (Cyno OSM ranking) |
| --- | --- | --- | --- |
| 1 | 10G8Ch | 0.021 ± 0.008 (140 pM) | 0.008 ± 0.007 (1) (53 pM) |
| 2 | 10G8 | 0.054 ± 0.066 (360 pM) | 0.034 ± 0.047 (3) (227 pM) |
| 3 | 9G2 | 0.163 ± 0.197 (1.1 nM) | 0.046 ± 0.025 (4) (307 pM) |
| 4 | 9G2Ch | 0.231 ± 0.287 (1.5 nM) | 0.031 ± 0.008 (2) (207 pM) |
| 5 | 15E10 | Out of Range | 0.057 ± 0.036 (5) (380 pM) |

In the presence of 25% human AB serum, 10G8, 10G8 Chimaera, 9G2 & 9G2 Chimaera retained their ability to neutralise both human and cynomolgus OSM (FIG. 14). Some drop-off in activity was seen in the presence of 25% AB serum. While IC50 values could not be calculated with a 1 µg/ml antibody starting concentration, a clear titration neutralisation effect was seen for all antibodies except the unrelated negative control. This drop-off in activity may, to some extent, be due to the AB serum interfering with this assay readout. Higher IL-6 background levels were observed in this assay than in the non-human serum.

Endogenous Human OSM (gp130 Assay):

10G8, 10G8 Chimaera, 9G2 & 9G2 Chimaera, inhibited endogenous human OSM from two separate donors (FIG. 15). For these two donors, 10G8 and 10G8 chimaera ranked joint first, while 9G2 and its chimaera ranked third and fourth respectively (Table 7). This native OSM was generated from GM-CSF-stimulation of healthy human neutrophils.

TABLE 7

Endogenous OSM Human gp130 Assay - Summary of two neutrophil donors in the gp130 ELISA to assess of 10G8, 10G8 Chimaera, 9G2 & 9G2 Chimaera activity against endogenous human OSM. A tool antibody was used as a negative control.

| Ranking | mAb | IC50 µg/ml ± SD |
| --- | --- | --- |
| 1= | 10G8 | 0.009 ± 0.001 (60 pM) |
| 1= | 10G8Ch | 0.009 ± 0.000 (60 pM) |
| 3 | 9G2Ch | 0.017 ± 0.001 (113 pM) |
| 4 | 9G2 | 0.020 ± 0.004 (133 pM) |

Human LIF Reactivity (KB Cell Neutralisation Assay):

Human LIF is the closest related member of the IL-6 family to human OSM. Three repeats of the Human LIF KB cell assay showed that 10G8, 10G8 chimaera, 9G2, and 9G2 chimaera did not neutralise human LIF. A commercially available anti-human LIF antibody did neutralise LIF in this assay (FIG. 16). This proves that these antibodies are OSM-specific.

Example 2

Humanisation 2.1.1 Heavy Chain Humanisation Strategy

Following a BLAST analysis of the human V gene germline databases, human germline IGHV3_7) which had 74% identity (including CDRs) with the mouse 10G8 variable heavy chain sequence was selected as the preferred acceptor framework for humanisation. The germline V region was combined in silico with a suitable FR4, in this case the JH2 minigene (Kabat Vol. II) based on sequence similarity. The first six residues of the JH2 minigene residues fall within the CDR3 region which is replaced by the incoming CDR from the donor antibody. Three humanised heavy chain variants were generated on the basis of sequence comparison and possible impact on antibody function. Construct H0 was a straight graft of mouse CDRs from 10G8 (using the Kabat definition) into the human acceptor framework selected above. Constructs H1 and H2 are based on H0, both incorporate one additional framework mutation which were different in each construct; positions 2 and 105 respectively.

2.1.2 Light Chain Humanisation

Following a BLAST analysis of the human V gene germline databases, human germline IGKV4_1) which had 64% identity (including CDRs) with the mouse 10G8 variable light chain sequence was selected as the preferred acceptor framework for humanisation. The germline V region was combined in silico with a suitable FR4, in this case the J-region kappa 4 minigene (Kabat Vol. II) based on sequence similarity. The first two residues of the JK-4 minigene residues fall within the CDR3 region and are identical to the last two residues in the mouse 10G8 light chain CDR3. Five humanised light chain variants were generated on the basis of sequence comparison and possible impact on antibody function. Construct L0 was a straight graft of mouse CDRs from 10G8 (using the Kabat definition) into the human acceptor framework selected above. Constructs L1, L2 and L3 are based on L0, each incorporates one additional framework mutation which were different in each construct; positions 46, 84 and 103 respectively. Construct L4 incorporates all three of the above back mutations.

2.1.3 Construction of Humanised Vectors

The DNA sequences of the humanised variable regions were sequence optimised using the LETO 1.0 software (Entelechon GmbH) and synthesised de novo by build up of overlapping oligonucleotide and PCR amplification. Primers included restriction sites for cloning into mammalian expression vectors and human immunoglobulin signal sequences for secretion. The humanised variable heavy regions H0-H2 were cloned into mammalian expression vectors containing the human gamma 1 constant region using HindIII and SpeI. In parallel, the humanised variable light regions L0-L4 were cloned into mammalian expression vectors containing the human kappa constant region using HindIII and BsiWI.

2.1.4 Initial Screening of the Panel of Humanised Variants

To screen and narrow the panel of humanised variants (3 heavy chain×5 light chains=15), the antibodies were expressed in HEK cells and assessed by BIACore, ELISAs and functional assays.

2.2 Humanised 10G8 Antibodies Bioassays: Chimaera to Humanised mAbs 2.2.1 Secondary Screen The secondary screening to rank the humanised 10G8 antibodies, listed in Table 9, included BIACore kinetic analysis against human OSM; human gp130 ELISA with human/cynomolgus OSM; KB cell neutralisation assay with human/cynomolgus OSM. In addition to this, the ability to block gp130 binding in 25% human AB serum was assessed.

BIACore Analysis:

Initial BIACore analysis on transfection supernatants demonstrated that L1 and L4 humanised variants had higher affinities for human OSM than L0, L2 and L3 humanised variants (Table 8). These light chain mutations improved affinity compared with the straight-graft alone (H0L0) and the 10G8 chimaera. The heavy chain variants, H1 and H2, had little impact on the affinity of the antibodies over the straight-graft, H0.

Analysis on the scaled-up purified L1 and L4 variants showed that there were very few differences between the affinities of these mAbs to both human and cyno OSM (Table 9).

TABLE 8

BIACore Kinetics - Human OSM binding kinetics of fifteen anti-OSM back-up humanised 10G8 antibodies transfection supernatants compared with the 10G8 Chimæra.

|  | Ka (M−1 · s−1) | Kd (s−1) | KD (nM) |
|---|---|---|---|
| H0L0 | 3.69E+5 | 1.60E−4 | 0.435 |
| H0L1 | 3.98E+5 | 9.95E−5 | 0.250 |
| H0L2 | 3.65E+5 | 1.37E−4 | 0.375 |
| H0L3 | 3.74E+5 | 1.45E−4 | 0.388 |
| H0L4 | 4.13E+5 | 1.11E−4 | 0.268 |
| H1L0 | 3.81E+5 | 1.62E−4 | 0.425 |
| H1L1 | 4.00E+5 | 9.99E−5 | 0.250 |
| H1L2 | 3.65E+5 | 1.63E−4 | 0.445 |
| H1L3 | 3.71E+5 | 1.27E−4 | 0.344 |
| H1L4 | 3.77E+5 | 1.30E−4 | 0.344 |
| H2L0 | 3.63E+5 | 1.45E−4 | 0.398 |
| H2L1 | 3.94E+5 | 1.13E−4 | 0.286 |
| H2L2 | 3.68E+5 | 1.42E−4 | 0.387 |
| H2L3 | 3.76E+5 | 1.50E−4 | 0.398 |
| H2L4 | 4.48E+5 | 1.01E−4 | 0.226 |
| 10G8 Chimæra supernatant | 2.52E+5 | 1.03E−4 | 0.407 |
| 10G8 Chimæra purified | 2.57E+5 | 1.05E−4 | 0.407 |

TABLE 9

BIACore Kinetics - Cynomolgus and Human OSM binding kinetics of the purified batches of anti-OSM humanised 10G8 L1 and L4 variant antibodies compared with the 10G8 Chimæra

|  | Cyno OSM | | | Human OSM | | |
|---|---|---|---|---|---|---|
|  | Ka (M−1 · s−1) | Kd (s−1) | KD (nM) | Ka (M−1 · s−1) | Kd (s−1) | KD (nM) |
| H0L1 | 4.26E+5 | 1.07E−4 | 0.251 | 3.87E+5 | 1.37E−4 | 0.355 |
| H1L1 | 4.28E+5 | 1.10E−4 | 0.258 | 3.75E+5 | 1.66E−4 | 0.443 |
| H2L1 | 4.14E+5 | 1.24E−4 | 0.299 | 3.83E+5 | 1.40E−4 | 0.365 |
| H0L4 | 4.18E+5 | 1.01E−4 | 0.242 | 3.74E+5 | 1.40E−4 | 0.374 |
| H1L4 | 4.21E+5 | 1.11E−4 | 0.264 | 3.65E+5 | 1.35E−4 | 0.370 |
| H2L4 | 4.41E+5 | 9.01E−5 | 0.205 | 3.80E+5 | 1.35E−4 | 0.356 |
| 10G8 chimera | 2.53E+5 | 9.95E−5 | 0.394 | 2.41E+5 | 1.25E−4 | 0.518 |
| 15E10h | 5.26E+5 | 3.10E−4 | 0.590 | 4.29E+5 | 6.15E−4 | 1.43 |

KB Cell Neutralisation Assay:

The KB cell neutralisation assay uses a reduced amount of OSM compared with the gp130 assay (1 ng/ml versus 25 ng/ml). This makes it a more discriminating assay for separating high affinity from low affinity neutralisers. A KB cell assay screen of the initial H0, H1, H2, L0, L1, L2, L3 and L4 variant constructs showed superiority in the L1 constructs (Data not shown). These, along with the L4 variants which performed well in the BIACore analysis, were produced in larger batches for further assays. From three repeats of the assay, Humanised 10G8 L1 variants ranked first, giving a mean IC50 value of 14 ng/ml against human OSM and 10 ng/ml against cynomolgus (FIG. 17; Table 10).

TABLE 10

KB Cell Neutralisation Assay - Summary of three repeats of the KB cell neutralisation assay to rank Humanised 10G8 L1 and L4 Variants activity against human and cynomolgus OSM.

| Human OSM Ranking | Antibody | Human OSM Mean IC50 µg/ml ± SD | Cynomolgus OSM Mean IC50 µg/ml ± SD (Cyno OSM ranking) |
|---|---|---|---|
| 1 | H1L1 | 0.013 ± 0.001 (83 pM) | 0.010 ± 0.002 (3) (67 pM) |
| 2 | H2L1 | 0.014 ± 0.007 (93 pM) | 0.013 ± 0.003 (6) (14 pM) |
| 3 | H0L1 | 0.015 ± 0.009 (102 pM) | 0.007 ± 0.002 (1) (21 pM) |
| 4 | H1L4 | 0.016 ± 0.015 (107 pM) | 0.011 ± 0.007 (4) (10 pM) |
| 5 | H0L4 | 0.018 ± 0.012 (118 pM) | 0.012 ± 0.009 (5) (49 pM) |
| 6 | H2L4 | 0.022 ± 0.015 (147 pM) | 0.016 ± 0.015 (7) (58 pM) |
| 7 | 10G8 Chimaera | 0.022 ± 0.022 (144 pM) | 0.008 ± 0.005 (2) (100 pM) |

The Humanised 10G8 L1 variants were selected for further testing as they showed greater biological activity in the KB cell assay compared with the L4 variants. The L4 variants had a very low production yield in the CHO-E1a system and this also ruled them out for further progression.

Human gp130 ELISA:

The human gp130 ELISA uses relatively high levels of OSM (25 ng/ml), reducing its ability to separate high affinity from lower affinity antibodies, as the ligand is in excess. Following two repeats of this assay with the Humanised 10G8 L1 variants, all three variants were shown to be equipotent in blocking both human and cynomolgus OSM from binding to gp130 receptor in this assay (FIG. 18). The human gp130 assay was also carried out in the presence of 25% human AB serum. Two repeats of this assay showed that all antibodies, Humanised 10G8 H0L1, H1L1 and H2L1 variants retained their ability to block human and cynomolgus OSM from binding to gp130 (Data not shown).

2.3 Isolation of Fab Fragments and Crystallisation of 10G8 mAb-OSM Complex 2.3.2 Generation of Fab Fragments Fab fragments from the 10G8 parental antibody were generated by digestion with bead immobilized papain (Pierce 20341) for 20 h at 37 C. in a buffer containing 20 mM phosphate buffer pH 7, 10 mM EDTA and 10 mM L-cysteine. Following digestion the beads were removed using a disposable plastic column, contaminating Fc fragments and undigested antibody were then removed from the Fab fragments using Protein A type chromatography (MabSelect, GE Healthcare 17-5438-03). The unbound fraction, containing the Fab fragments, were further purified using Superdex 200 pg Size Exclusion Chromatography (SEC) (GE Healthcare 17-1069-01) using 25 mM HEPES pH 7.7, 150 mM NaCl buffer as the mobile phase. The complex was made by mixing 11.5 mg purified Fabs (GRITS30249) with 5.75 mg recombinant OSM (GRITS23122), a molar ratio of 1:1, for 1.5 h at 4 C. The complex was then purified from uncomplexed material using Superdex 200 pg SEC. Resolved complex was concentrated to 44 mg/ml total protein (yield 9.2 mg) using a centrifugal concentration device fitted with a 10 kmwco membrane (Vivaspin VS2002). Complex components were validated using N-terminal sequencing, mass spectrometry and SDS-PAGE. OSM functional binding activity of the Fab fragments was confirmed using the gp130 inhibition assay (data not shown).

2.3.2 10G8-OSM Complex Crystallisation

10G8 OSM Fab fragments were complexed with OSM, and this was crystallised at 20° C. using PEG3500 as a precipitate. Crystallisation was optimised, sent for analysis at the European Synchrotron Radiation Facility (ESRF) and the structure solved at 3.5 Å. The 10G8 mAb bound helices B and C of OSM with good surface complimentarity and blocked OSM Site II from binding gp130 receptor purely by steric hindrance, with no direct interaction with any residues from Site II. The only residues directly involved in binding (distance of less than 5 Å) when resolved at 3.5 Å are illustrated in Table 11 and FIG. 19. The light chain was responsible for most of this blocking effect. Four CDRs bound helices B and C of OSM, CDRH2, H3 and CDRL1 and L3, either directly or through water mediation interactions. There was no significant distortion of the OSM molecule on binding 10G8 mAb. As two of the CDRs were non-binding, CDRH1 and L2, variants of the antibody were be made where one or both of these were reverted back to a human sequence. This may lead to a less immunogenic molecule than the straight humanised graft.

TABLE 11

| OSM residues | Resno(Type) | Atom | Antibody residues (L = light chain, H = heavy chain) | Resno(Type) | Atom | Distance In Angstroms |
|---|---|---|---|---|---|---|
| A | 82(LEU) | C | H | 104(THR) | CG2 | 3.45 |
| A | 82(LEU) | O | H | 104(THR) | CG2 | 3.47 |
| A | 83(HIS). | CA | H | 59(TYR) | OH | 3.20 |
| A | 83(HIS). | CB | H | 59(TYR) | OH | 3.37 |
| A | 83(HIS). | CE1 | H | 103(THR). | CG2 | 3.43 |
| A | 83(HIS). | NE2 | H | 106(TRP). | CH2 | 3.44 |
| A | 83(HIS). | CD2 | H | 59(TYR). | OH | 3.30 |
| A | 83(HIS). | C | H | 59(TYR). | OH | 3.26 |
| A | 83(HIS). | O | H | 59(TYR). | OH | 2.62 |
| A | 84(ARG). | NH1 | H | 57(PHE). | CE1 | 3.47 |
| A | 90(GLN). | OE1 | H | 60(TYR). | O | 3.30 |
| A | 90(GLN). | NE2 | H | 65(ARG). | NH2 | 3.08 |
| A | 94(LYS). | NZ | H | 62(ASP). | OD2 | 3.38 |
| A | 115(ARG). | NE | H | 104(THR). | OG1 | 3.19 |
| A | 115(ARG). | NH2 | H | 105(PHE). | CD1 | 3.49 |
| A | 115(ARG). | NH2 | H | 105(PHE). | CE1 | 3.25 |
| A | 115(ARG). | NH2 | H | 104(THR). | O | 3.21 |
| A | 122(ARG). | NH2 | H | 103(THR). | OG1 | 3.14 |
| A | 152(THR). | OG1 | H | 58(THR). | OG1 | 3.19 |
| A | 112(GLN). | O | L | 96(ARG). | NH2 | 3.08 |
| A | 115(ARG). | NH2 | L | 96(ARG). | O | 3.30 |
| A | 123(ASN). | CG | L | 34(TYR). | OH | 3.18 |
| A | 123(ASN). | ND2 | L | 34(TYR). | OH | 2.56 |

2.3.3

2.3.4 Humanised 10G8 Antibody: Human CDR Substitutions

The in-house solved crystal structure of the anti-OSM 10G8 mAb complexed with OSM, identified CDRH1 and CDRL2 as not being directly involved in antigen binding.

Suitable human germline CDRs were selected to replace these mouse germline CDRs. Two CDRH1 and two CDRL2 human germline sequences were tested for their effects on antigen binding. For both heavy and light chain CDRs the sequences from the original human germline acceptor framework were tested (IGHV3_7 and IGKV4_1 respectively) and also two further human germline sequences which were selected based on CDR and flanking framework homology (IGHV3_23 and IGKV1_5). The human germline CDRH1 and CDRL2 sequences were exchanged for the respective mouse CDRs in the humanized H0 and L1 V-regions. The new V-regions were synthesised de novo by build up of overlapping oligonucleotide and PCR amplification as in section 1.1.4.

2.4 Humanised 10G8 Antibodies Bioassays: Humanised 10G8 H0L1 mAb to Humanised 10G8 mAb with Humanised Non-Binding CDR 2.4.1 Secondary Screen BIACore Analysis:

BIACore analysis on transfection supernatants from the various humanised 10G8 H0L1 CDRH1 and CDRL2 constructs demonstrated that the only antibody to fully retain the human OSM affinity of the pre-candidate mAb was H0(IGHV3_23)L1 molecule (Table 12). This construct, along with two further molecules with the next best KD values, H0L1(IGKV4_1) and H0(IGHV3_23)L1(IGK4_1), were scaled-up and purified for further study.

TABLE 12

BIACore Kinetics - Cynomolgus and Human OSM binding kinetics of the transfection supernatants of anti-OSM back-up humanised 10G8 H0L1 CDRH1 and CDRL2 variant antibodies compared with the 10G8 Chimaera.

| | Cyno OSM | | | Human OSM | | |
|---|---|---|---|---|---|---|
| | Ka $(M^{-1} \cdot s^{-1})$ | Kd $(s^{-1})$ | KD (nM) | Ka $(M^{-1} \cdot s^{-1})$ | Kd $(s^{-1})$ | KD (nM) |
| H0 IGHV3_7 + L1 | 3.37E+7 | 0.8146 | 24.2 | 9.10E+4 | 9.67E−4 | 10.6 |
| H0 IGHV3_23 + L1 | 3.52E+5 | 1.09E−4 | 0.310 | 3.61E+5 | 1.58E−4 | 0.437 |
| H0 + L1 IGKV4_1 | 1.50E+5 | 2.12E−4 | 1.41 | 1.61E+5 | 2.21E−4 | 1.37 |
| H0 + L1 IGKV1_5 | 6.75E+4 | 5.57E−4 | 8.26 | 6.87E+4 | 6.40E−4 | 9.33 |
| H0 IGHV3_7 + L1 IGKV4_1 | 5.07E+4 | 1.77E−3 | 34.9 | 3.68E+4 | 1.63E−3 | 44.4 |
| H0 IGHV3_7 + L1 IGKV1_5 | low capture level | | | low capture level | | |
| H0 IGHV3_23 + L1 IGKV4_1 | 1.52E+5 | 2.23E−4 | 1.47 | 1.59E+5 | 2.47E−4 | 1.56 |
| H0 IGHV3_23 + L1 IGKV1_5 | 6.67E+4 | 5.93E−4 | 8.89 | 7.11E+4 | 6.60E−4 | 9.27 |
| H0 + L1 | 3.45E+5 | 1.04E−4 | 0.301 | 3.32E+5 | 1.53E−4 | 0.461 |
| H0L1 purified | 3.38E+5 | 1.15E−4 | 0.341 | 3.40E+5 | 1.51E−4 | 0.445 |

KB Cell Neutralisation Assay:

The KB cell neutralisation assay demonstrated that the humanised 10G8 H0(IGHV3_23)L1 construct (labelled as H0('CDRH1)L1) shows very similar potency to the parent Humanised 10G8 H0L1 (labelled as H0L1) mAb. Any reversion of the non-binding CDRL2 to the human sequence showed a decrease in neutralisation activity, as seen from the data for the H0L1(IGKV4_1) (labelled H0L1(huCDRL2)) and H0(IGHV3_23)L1(IGK4_1) (Labelled H0(huCDRH1)L1(huCDRL2)) antibodies (FIG. 20, Table 13).

TABLE 13

KB Cell Neutralisation Assay - Summary of three repeats of the KB cell neutralisation assay to rank Humanised 10G8 H0L1 CDRH1 and CDRL2 Variants activity against human and cynomolgus OSM.

| Human OSM Ranking | Antibody | Human OSM Mean IC50 µg/ml ± SD | Cynomolgus OSM Mean IC50 µg/ml ± SD (Cyno OSM ranking) |
|---|---|---|---|
| 1 | H0(huCDRH1)L1 | 0.008 ± 0.005 (53 pM) | 0.007 ± 0.000 (1) (47 pM) |
| 2 | H0L1 | 0.009 ± 0.002 (60 pM) | 0.007 ± 0.002 (2) (47 pM) |
| 3 | H0L1(huCDRL2) | 0.054 ± 0.024 (360 pM) | 0.081 ± 0.004 (4) (540 pM) |
| 4 | H0(huCDRH1)L1(huCDRL2) | 0.077 ± 0.038 (513 pM) | 0.114 ± 0.045 (5) (760 pM) |

From these data, the Humanised 10G8 H0(huCDRH1)L1 was chosen as the lead pre-candidate mAb for full characterisation.

2.5 Humanised 10G8 Antibodies Bioassays: Humanised 10G8 H0(IGHV3_23)L1 mAb
2.5.1 Secondary Screen
BIACore Analysis:

BIACore analysis was carried out on purified H0(IGHV3_23)L1 mAb and ranked against the 10G8 chimaera and Humanised 10G8 H0L1 parent mAb. There was little or no difference between H0(IGHV3_23)L1 mAb and the parent H0L1 mAb in affinity for both human and cyno OSM (Table 6). H0(IGHV3_23)L1 mAb had a 6.5-fold (0.8 log) increased affinity for human OSM compared to an alternative non-competitive anti-OSM humanised antibody 15E10h A new batch of OSM was used for this study, resulting in lower KD values however, the differences between the humanised variants and the non-competitive antibody remained the same.

TABLE 14

BIACore Kinetics - Cynomolgus and Human OSM binding kinetics of purified H0(IGHV3_23)L1 mAb compared with 10G8 Chimæra and compared with the Humanised 10G8 H0L1 parent mAb and to an alternative non-competitive anti-OSM humanised antibody 15E10h.

| | Cyno OSM | | | Human OSM | | |
|---|---|---|---|---|---|---|
| | Ka (M−1·s−1) | Kd (s−1) | KD (pM) | Ka (M−1·s−1) | Kd (s−1) | KD (pM) |
| 10G8 chimaera | 2.50E+05 | 6.63E−05 | 266 | 4.27E+05 | 7.87E−05 | 184 |
| H0 (CDRH1 IGHV3_23) L1 | 4.23E+05 | 8.39E−05 | 199 | 7.09E+05 | 9.65E−05 | 136 |
| H0L1 | 4.27E+05 | 8.31E−05 | 195 | 7.12E+05 | 8.90E−05 | 125 |
| 15E10h | 5.07E+05 | 3.24E−04 | 640 | 7.36E+05 | 6.49E−04 | 882 |

Kinexa Analysis

Kinexa (Sapidyne Instruments 3200) solution phase affinity was used to determine the overall affinity of anti-OSM antibody H0(huCDRH1)L1 and Humanised 15E10 (an unrelated OSM antibody) to human, cynomolgus macaque, rhesus macaque and marmoset OSM (Table 15). Humanised 15E10 was added for comparison purposes.

OSM beads were prepared either by adsorption (polymethylmethacrylate beads-PMMA) or amine coupling (NHS-activated sepharose beads). The range of OSM molecules studied necessitated the generation of beads coated with different concentrations of OSM. For the solution phase portion of the assay, a fixed concentration of antibody was incubated with a broad range of OSM concentrations and allowed to reach equilibrium by incubation at r.t. for at least 2 h before analysis proceeded. The OSM beads were then used to determine the amount of free antibody present in the solution phase samples, by means of the free antibody binding to the OSM bead matrix then detected using an appropriate secondary antibody (either anti-human or anti-mouse depending on the construct being tested) labelled with a fluorescent dye. The binding curves where fitted using the Kinexa Pro analysis software inherent to the machine. Multiple runs using varying starting concentrations of antibody were then compiled and analysed using the n-curve analysis software to give a more accurate determination of affinity.

H0(huCDRH1)L1 shows a higher affinity for human OSM as was previously assessed by Biacore analysis. Unlike Biacore where the antibody was bound to the chip surface, Kinexa uses free antibody and ligand in a fluid phase to assess affinity, which is more akin to the natural state

TABLE 15

Kinexa Kinetics - Human, cynomolgus, rhesus and marmoset OSM binding kinetics of purified anti-OSM back-up antibody H0(huCDRH1)L1 and Humanised 15E10.

| Construct | Antigen | KD (pM) | 95% high (pM) | 95% low (pM) |
|---|---|---|---|---|
| H0(huCDRH1)L1 | Human OSM | 38 | 62 | 22 |
| H0(huCDRH1)L1 | Cyno OSM | 53 | 82 | 31 |
| H0(huCDRH1)L1 | Marmoset OSM | 21 | 31 | 14 |
| H0(huCDRH1)L1 | Rhesus OSM | 122 | 161 | 90 |
| Humanised 15E10 | Human OSM | 727 | 1000 | 499 |
| Humanised 15E10 | Cyno OSM | 102 | 157 | 61 |

TABLE 15-continued

Kinexa Kinetics - Human, cynomolgus, rhesus and marmoset OSM binding kinetics of purified anti-OSM back-up antibody H0(huCDRH1)L1 and Humanised 15E10.

| Construct | Antigen | KD (pM) | 95% high (pM) | 95% low (pM) |
|---|---|---|---|---|
| Humanised 15E10 | Marmoset OSM | **6100 | 468000 | <22.5 |
| Humanised 15E10 | Rhesus OSM | 102 | 181 | 52 |

**The affinity is very poor for marmoset OSM which means that for a receptor driven experiment more than 40 nM of antibody would be needed to use uM amounts of OSM. Overall conclusion is that the binding of 15E10 humanised to marmoset OSM is significantly poorer than it is to human OSM.

Human gp130 ELISA:

The human gp130 ELISA uses an excess of OSM (25 ng/ml), thus reducing its ability to separate high affinity from lower affinity antibodies. Following three repeats of the gp130 assay, it was confirmed that the 10G8 mouse parental, the 10G8 Chimera, the Humanised 10G8 H0L1 parent (H0L1) and H0(huCDRH1)L1 were all potent in blocking both human and cynomolgus OSM from binding to gp130 receptor in this assay (FIG. 21). Due to the high levels of antigen in this assay, there were no clear ranking could be discerned.

The human gp130 assay was repeated in the presence of 25% human AB serum and 25% human pooled synovial fluid. Three repeats of this assay for each matrix showed that all antibodies, the 10G8 mouse parental, the 10G8 Chimera, the Humanised 10G8 H0L1 parent (H0L1) and H0(huCDRH1)L1 along with 15E10h retained their ability to block human and cynomolgus OSM from binding to gp130 (Data not shown).

KB Cell Neutralisation Assay:

The KB cell neutralisation assay is a more discriminating assay for separating high affinity from low affinity neutralisers than the gp130 assay, due to the low (1 ng/ml) levels of OSM used. From three repeats of the assay, (H0(huCDRH1) L1 gave a mean IC50 value of 30 ng/ml against human OSM, 41 ng/ml against cynomolgus OSM and 36 ng/ml against marmoset OSM (FIG. 22; Table 17).

assay showed that the 10G8 mouse parental, the 10G8 Chimaera, the Humanised 10G8 H0L1 parent (H0L1) and H0(huCDRH1)L1 or 15E10h did not neutralise human LIF. 15E10h was added for comparison purposes. A commercially available anti-human LIF antibody did neutralise LIF in this assay (FIG. 25). This proves that these antibodies are OSM-specific.

TABLE 17

KB Cell Neutralisation Assay - Summary of three repeats of the KB cell neutralisation assay to rank H0(huCDRH1)L1 activity against human, cynomolgus and marmoset OSM. 15E10h was added for comparison purposes

| Human OSM Ranking | Antibody | Human OSM Mean IC50 μg/ml ± SD | Cynomolgus OSM Mean IC50 μg/ml ± SD (Cyno OSM ranking) | Marmoset OSM Mean IC50 μg/ml ± SD (Marm OSM ranking) |
|---|---|---|---|---|
| 1 | 10G8 | 0.0026 ± 0.0009 (17 pM) | 0.0017 ± 0.0006 (3) (11 pM) | 0.0017 ± 0.0003 (1) (11 pM) |
| 2 | H0L1 | 0.0028 ± 0.0004 (19 pM) | 0.0014 ± 0.0003 (2) (9 pM) | 0.0017 ± 0.0008 (2) (11 pM) |
| 3 | (H0(huCDRH1)L1 | 0.0030 ± 0.0015 (20 pM) | 0.0041 ± 0.0025 (4) (27 pM) | 0.0036 ± 0.0024 (3) (24 pM) |
| 4 | 10G8Ch | 0.0052 ± 0.0064 (35 pM) | 0.0011 ± 0.0004 (1) (7 pM) | 0.0271 ± 0.0450 (4) (181 pM) |
| 5 | 15E10h | 0.0391 ± 0.0207 (261 pM) | 0.0054 ± 0.0020 (5) (36 pM) | No Neutralisation |

In the presence of 25% human AB serum or 25% pooled human synovial fluid, (H0(huCDRH1)L1 and 15E10h retained their ability to neutralise both human and cynomolgus OSM (FIG. 23). Some drop-off in activity was seen in the presence of either 25% AB serum or 25% pooled synovial fluid. This is most probably due to these matrices interfering with this assay readout. Higher IL-6 background levels were observed in this assay than in the normal assay.

Unlike 15E10h, H0(huCDRH1)L1 has been shown to neutralise marmoset OSM in the KB cell neutralisation assay. A panel of three additional anti-human OSM antibodies, 10D3DLE, OM4.11.17 and OM4.11.31, also failed to neutralise marmoset OSM.

Endogenous Human OSM gp130 Assay:

The 10G8 mouse parental, the 10G8 Chimaera, the Humanised 10G8 H0L1 parent (H0L1) and H0(huCDRH1)L1 as well as 15E10h inhibited endogenous human OSM from four separate donors (FIG. 24). From the results of these four donors, there was very little difference between the H0L1 parent and the H0(huCDRH1)L1 mAbs; these ranked higher than the 10G8 mouse parental and its chimaera (Table 18). H0(huCDRH1)L1 had approximately 12-fold (1.09 log) increase in potency compared with 15E10h. The native OSM was generated from GM-CSF-stimulation of healthy human neutrophils.

TABLE 18

Endogenous OSM Human gp130 Assay- Summary of four neutrophil donors in the gp130 ELISA to assess the 10G8 mouse parental, 10G8 Ch, the Humanised 10G8 H0L1 parent (H0L1) and H0(huCDRH1)L1 activity against endogenous human OSM. 15E10h was added for comparison purposes. An unrelated antibody was used as a negative control.

| Ranking | mAb | IC50 μg/ml ± SD |
|---|---|---|
| 1 | H0L1 | 0.0058 ± 0.0019 (39 pM) |
| 2 | H0(huCDRH1)L1 | 0.0062 ± 0.0023 (41 pM) |
| 3 | 10G8 | 0.0090 ± 0.0020 (60 pM) |
| 4 | 10G8Ch | 0.0091 ± 0.0004 (61 pM) |
| 5 | 15E10h | 0.0760 ± 0.0181 (507 pM) |

Human LIF Reactivity (KB Cell Neutralisation Assay):

Human LIF is the closest related member of the IL-6 family to human OSM. Three repeats of the Human LIF KB cell Primary Human Hepatocyte Assay:

Human primary hepatocytes are sensitive to OSM and release acute phase proteins, such as SAA and CRP, in response to OSM stimulation. H0(huCDRH1)L1 inhibited human OSM-induced SAA (FIG. 26) and CRP (FIG. 27) release in hepatocytes in a dose-dependent manner from three separate donors. Humanised 15E10 was added for comparison purposes.

Equivalent assays were carried out using other primary human cell types. These included human umbilical vein endothelial cells; human fibroblast like synoviocytes from rheumatoid arthritis patients; human lung fibroblasts from healthy and idiopathic lung fibrosis patients (data not shown). As with the previous assays, H0(huCDRH1)L1 shows superior neutralisation of OSM over humanised 15E10. The fold difference in the potency between H0(huCDRH1)L1 and humanised 15E10 varies depending on cell line and OSM concentration.

2.6 Biophysical Characterisation

A basic biophysical profile of H0(huCDRH1)L1 was carried out along with the Humanised 10G8 H0L1 parent mAb. The antibodies were subjected to environmental stresses, such as:

Temperature, by incubation for 14 days at 4° C. or 37° C.;
Five freeze-thaw cycles;
Forced deamidation, by incubation with 1% ammonium bicarbonate at 37° C. for 48 hours.

Neither antibody showed loss in biophysical alteration or loss in activity following the above mentioned stresses.

2.6 CDRH3 Variant Humanised Antibodies 2.6.1 Construction of CDRH3 Variant Humanised Antibodies Substitution of each residue of CDRH3 (SEQ ID NO:3) to an alternative amino acid residue was carried out using the heavy chain H0(IGHV3_23) full length sequence SEQ ID NO. 75 (variable sequence: SEQ ID NO: 74) on a pTT plasmid (National Research Council Canada, with a modified Multiple Cloning Site (MCS)) as a base molecule. The site-directed mutagenesis technique (SDM) was used whereby oligonucleotides are designed bearing the sequence NNK (N=A/T/G/C; K=G or T) at the amino acid substitution position. Polymerase chain reaction (PCR) was used to generate new plasmids containing the change, and DNA sequencing was used to identify clones with amino acid changes. In this way, variants were isolated having between 10 and 17 different amino acids at each of the 12 CDRH3 positions. CDRH3 variant antibodies were produced by co-transfecting pTT vectors comprising an H0(IGHV3_23) variant with the L1 light chain (SEQ ID NO: 72) and testing supernatants for binding.

164 CDRH3 variants were generated and tested in the subsequent analysis (see 2.6.2 and 2.6.3).

2.6.2 CDRH3 Variant Expression in HEK 293 6E Cells pTT plasmids encoding the heavy chain (H0(IGHV3_23)) CDRH3 variants and light chain L1 were transiently co-transfected into HEK 293 6E cells and expressed at small scale to produce antibody. Antibodies were assessed directly from the tissue culture supernatant.

2.6.3 Kinetic Analysis of CDRH3-Variant Tissue Culture Supernatants

The initial kinetic analyses for the CDRH3 screen were carried out on the ProteOn XPR36 (Biorad Laboratories) and certain supernatants were selected for more accurate kinetic analysis on the BiaCore T100.

For the ProteOn analysis, anti-human IgG (GE Healthcare/Biacore BR-1008-39) was coupled to a GLM chip (Biorad Laboratories 176-5012) by primary amine coupling. The CDRH3 variants were captured directly on to this surface and recombinant human OSM was passed over the captured antibody surface at 256, 64, 16, 4 and 1 nM, with a buffer injection alone (i.e. 0 nM) used to double reference the binding curves. Following the OSM binding event, the capture surfaces were regenerated: with 3M $MgCl_2$ the regeneration removed the previously captured antibody ready for another cycle of capture and binding analysis. The data was then fitted to the 1:1 model (with mass transport) inherent to the ProteOn analysis software. The run was carried out using HBS-EP (Biacore/GE-Healthcare BR-1006-69) and the analysis temperature was 25° C.

A similar method was used for analysis of constructs using the Biacore T100, anti-human IgG (GE Healthcare/Biacore BR-1008-39) was coupled to a CM5 chip (GE Healthcare/Biacore BR-1006-68) by primary amine coupling, antibodies were captured on this surface and recombinant human OSM was passed over the captured antibody surface at 256, 64, 16, 4 and 1 nM, with a buffer injection alone (i.e. 0 nM) used to double reference the binding curves. Regeneration was by using pulses of 3M 3M $MgCl_2$ or 100 mM phosphoric acid or using both reagents. The data was fitted to the 1:1 model inherent to the Biacore T100 analysis software. The run was carried out using HBS-EP (Biacore/GE-Healthcare BR-1006-69) and the analysis temperature was 25° C.

See FIG. 33 for binding data results.

TABLE A

Sequence Summary

| Description | Amino acid sequence | Polynucleotide sequence |
|---|---|---|
| 10G8 CDRH1 | SEQ. I.D. NO: 1 | n/a |
| 10G8 CDRH2 | SEQ. I.D. NO: 2 | n/a |
| 10G8 CDRH3 | SEQ. I.D. NO: 3 | n/a |
| 10G8 CDRL1 | SEQ. I.D. NO: 4 | n/a |
| 10G8 CDRL2 | SEQ. I.D. NO: 5 | n/a |
| 10G8 CDRL3 | SEQ. I.D. NO: 6 | n/a |
| 3E3 CDRH1 | SEQ. I.D. NO: 7 | n/a |
| 3E3 CDRH2 | SEQ. I.D. NO: 8 | n/a |
| 3E3 CDRH3 | SEQ. I.D. NO: 9 | n/a |
| 3E3 CDRL1 | SEQ. I.D. NO: 10 | n/a |
| 3E3 CDRL2 | SEQ. I.D. NO: 11 | n/a |
| 3E3 CDRL3 | SEQ. I.D. NO: 12 | n/a |
| 2B7 CDRH1 | SEQ. I.D. NO: 13 | n/a |
| 2B7 CDRH2 | SEQ. I.D. NO: 14 | n/a |
| 2B7 CDRH3 | SEQ. I.D. NO: 15 | n/a |
| 2B7 CDRL1 | SEQ. I.D. NO: 16 | n/a |
| 2B7 CDRL2 | SEQ. I.D. NO: 17 | n/a |
| 2B7 CDRL3 | SEQ. I.D. NO: 18 | n/a |
| 9G2 CDRH1 | SEQ. I.D. NO: 19 | n/a |
| 9G2 CDRH2 | SEQ. I.D. NO: 20 | n/a |
| 9G2 CDRH3 | SEQ. I.D. NO: 21 | n/a |
| 9G2 CDRL1 | SEQ. I.D. NO: 22 | n/a |
| 9G2 CDRL2 | SEQ. I.D. NO: 23 | n/a |
| 9G2 CDRL3 | SEQ. I.D. NO: 24 | n/a |
| 10G8 $V_H$ domain (murine) | SEQ. I.D. NO: 26 | SEQ. I.D. NO: 25 |
| 10G8 $V_L$ domain (murine) | SEQ. I.D. NO: 28 | SEQ. I.D. NO: 27 |
| 3E3 $V_H$ domain (murine) | SEQ. I.D. NO: 30 | SEQ. I.D. NO: 29 |
| 3E3 $V_L$ domain (murine) | SEQ. I.D. NO: 32 | SEQ. I.D. NO: 31 |
| 2B7 $V_H$ domain (murine) | SEQ. I.D. NO: 34 | SEQ. I.D. NO: 33 |
| 2B7 $V_L$ domain (murine) | SEQ. I.D. NO: 36 | SEQ. I.D. NO: 35 |
| 9G2 $V_H$ domain (murine) | SEQ. I.D. NO: 38 | SEQ. I.D. NO: 37 |
| 9G2 $V_L$ domain (murine) | SEQ. I.D. NO: 40 | SEQ. I.D. NO: 39 |
| 10G8 $V_H$ domain (chimera) | SEQ. I.D. NO: 42 | SEQ. I.D. NO: 41 |
| 10G8 $V_L$ domain (chimera) | SEQ. I.D. NO: 44 | SEQ. I.D. NO: 43 |
| 9G2 $V_H$ domain (chimera) | SEQ. I.D. NO: 46 | SEQ. I.D. NO: 45 |
| 9G2 $V_L$ domain (chimera) | SEQ. I.D. NO: 48 | SEQ. I.D. NO: 47 |
| IGHV3_7 human variable heavy chain germline acceptor nucleotide sequence | SEQ. I.D. NO: 50 | SEQ. I.D. NO: 49 |
| IGKV4_1 human variable light chain germline acceptor nucleotide sequence | SEQ. I.D. NO: 52 | SEQ. I.D. NO: 51 |
| 10G8 Humanised $V_H$ H0 (nucleotide sequence was leto codon optimised) | SEQ. I.D. NO: 54 | SEQ. I.D. NO: 53 |

TABLE A-continued

Sequence Summary

| Description | Amino acid sequence | Polynucleotide sequence |
|---|---|---|
| 10G8 Humanised $V_H$ H1 (nucleotide sequence was leto codon optimised) | SEQ. I.D. NO: 56 | SEQ. I.D. NO: 55 |
| 10G8 Humanised $V_H$ H2 (nucleotide sequence was leto codon optimised) | SEQ. I.D. NO: 58 | SEQ. I.D. NO: 57 |
| 10G8 Humanised $V_L$ L0 (nucleotide sequence was leto codon optimised) | SEQ. I.D. NO: 60 | SEQ. I.D. NO: 59 |
| 10G8 Humanised $V_L$ L1 (nucleotide sequence was leto codon optimised) | SEQ. I.D. NO: 62 | SEQ. I.D. NO: 61 |
| 10G8 Humanised $V_L$ L2 (nucleotide sequence was leto codon optimised) | SEQ. I.D. NO: 64 | SEQ. I.D. NO: 63 |
| 10G8 Humanised $V_L$ L3 (nucleotide sequence was leto codon optimised) | SEQ. I.D. NO: 66 | SEQ. I.D. NO: 65 |
| 10G8 Humanised $V_L$ L4 (nucleotide sequence was leto codon optimised) | SEQ. I.D. NO: 68 | SEQ. I.D. NO: 67 |
| Mature H0 heavy chain (nucleotide sequence was leto codon optimised) | SEQ. I.D. NO: 70 | SEQ. I.D. NO: 69 |
| Mature L1 light chain (nucleotide sequence was leto codon optimised) | SEQ. I.D. NO: 72 | SEQ. I.D. NO: 71 |
| Humanised VH variant H0 (IGHV3_23 CDRH1) (nucleotide sequence was leto codon optimised) | SEQ. I.D. NO: 74 | SEQ. I.D. NO: 73 |
| Mature H0 (IGHV3_23 CDRH1) heavy chain (nucleotide sequence was leto codon optimised) | SEQ. I.D. NO: 76 | SEQ. I.D. NO: 75 |
| Human heavy chain germline IGHV3_23 CDRH1 | SEQ. I.D. NO: 77 | n/a |
| Human light chain germline IGKV1_5 CDRL2 | SEQ. I.D. NO: 78 | n/a |
| 15E10h Heavy chain | SEQ. I.D. NO: 79 | n/a |
| 15E10h Light chain | SEQ. I.D. NO: 80 | n/a |
| 15E10 Humanised VH B3 | SEQ. I.D. NO: 81 | n/a |
| 15E10 Humanised VL L2 | SEQ. I.D. NO: 82 | n/a |
| Human OSM | SEQ. I.D. NO: 84 | SEQ. I.D. NO: 83 |

Sequence Listing

SEQ ID NO: 1
10G8 CDRH1
NYAMS

SEQ ID NO: 2
10G8 CDRH2
TISDGGSFTYYLDNVRG

SEQ ID NO: 3
10G8 CDRH3
DVGHTTFWYFDV

SEQ ID NO: 4
10G8 CDRL1
RASKSVSAAGYNFMH

SEQ ID NO: 5
10G8 CDRL2
YASNLES

SEQ ID NO: 6
10G8 CDRL3
LHSREFPFT

SEQ ID NO: 7
3E3 CDRH1
SYAMS

SEQ ID NO: 8
3E3 CDRH2
TISDGGSFTYYFANIQG

SEQ ID NO: 9
3E3 CDRH3
DVGLTTFWYFDV

| Sequence Listing | |
|---|---|
| 3E3 CDRL1<br>RASKSVSPSGYDFMH | SEQ ID NO: 10 |
| 3E3 CDRL2<br>YASELES | SEQ ID NO: 11 |
| 3E3 CDRL3<br>QHSREFPFT | SEQ ID NO: 12 |
| 2B7 CDRH1<br>NYAMS | SEQ ID NO: 13 |
| 2B7 CDRH2<br>TISDGGGYTYYLDNGQG | SEQ ID NO: 14 |
| 2B7 CDRH3<br>DVGLTTFWYFDV | SEQ ID NO: 15 |
| 2B7 CDRL1<br>RASKSVSPSSYNFMH | SEQ ID NO: 16 |
| 2B7 CDRL2<br>YASNLES | SEQ ID NO: 17 |
| 2B7 CDRL3<br>QHSREFPFT | SEQ ID NO: 18 |
| 9G2 CDRH1<br>NYAMS | SEQ ID NO: 19 |
| 9G2 CDRH2<br>TISDGGSFTYYLDNVKG | SEQ ID NO: 20 |
| 9G2 CDRH3<br>DVGHTTFWYFDV | SEQ ID NO: 21 |
| 9G2 CDRL1<br>RASKSVSASGYNFMH | SEQ ID NO: 22 |
| 9G2 CDRL2<br>YASNLES | SEQ ID NO: 23 |
| 9G2 CDRL3<br>QHSREFPFT | SEQ ID NO: 24 |
| 10G8 $V_H$ nucleotide sequence<br>GAAATGCAACTGGTGGAGTCTGGGGAAGGCTTAGTGGAGCCTGGAGGGTCCCTGAAACTCTCC<br><br>TGTGCAGCCTCTGGATTCACTTTCAGTAACTATGCCATGTCTTGGGTTCGCCAGACTCCGGAAAA<br><br>GAGCCTGGAGTGGGTCGCAACCATTAGTGATGGTGGTAGTTTCACCTACTATCTAGACAATGTAA<br><br>GGGGCCGATTCACCATCTCCAGAGACAATGCCAAGAACAACCTGTATTTGCAAATGAGCCATTTG<br><br>AAGTCTGACGACACAGCCATGTATTACTGTGCAAGAGATGTGGGACATACTACCTTTTGGTACTT<br><br>CGATGTCTGGGGCTCAGGGACCGCGGTCACCGTCTCCTCA | SEQ ID NO: 25 |

Sequence Listing

SEQ ID NO: 26

10G8 V$_H$ amino acid sequence
EMQLVESGEGLVEPGGSLKLSCAASGFTFSNYAMSWVRQTPEKSLEWVATISDGGSFTYYLDNVRG

RFTISRDNAKNNLYLQMSHLKSDDTAMYYCARDVGHTTFWYFDWVGSGTAVTVSS

SEQ ID NO: 27

10G8 V$_L$ nucleotide sequence
GACATTGTGCTGACACAGTCTCCTGTTTTCTTAGTTGTATCTCTGGGGCAGAGGGCCACCATCTC

CTGTAGGGCCAGCAAAAGTGTCAGTGCAGCTGGCTATAATTTCATGCACTGGTACCAACAGAAA

CCAGGACAGCCGCCCAAAGTCCTCATCAAGTATGCATCCAACCTAGAATCTGGGGTCCCTGCCA

GGTTCAGTGGCAGTGGGTCTGGGACAGACTTCACCCTCAACATCCATCCTGTGGAGGAGGAGG

ATGCTGTAACATATTACTGTCTGCACAGTAGGGAGTTTCCGTTCACGTTCGGAGGGGGGACCAA

CCTGGAAATAAAA

SEQ ID NO: 28

10G8 V$_L$ amino acid sequence
DIVLTQSPVFLVVSLGQRATISCRASKSVSAAGYNFMHWYQQKPGQPPKVLIKYASNLESGVPARFS

GSGSGTDFTLNIHPVEEEDAVTYYCLHSREFPFTFGGGTNLEIK

SEQ ID NO: 29

3E3 V$_H$ nucleotide sequence
GAAGTGCAGCTGGTGGAGTCTGGGGGAGACTTAGTGAAACCTGGAGGGTCCCTGAAACTCTCC

TGTGTACCCTCTGGATTCACTTTCAGTAGTTATGCCATGTCTTGGGTTCGCCAGACTCCGGAAAA

GAGGCTGGAGTGGGTCGCAACCATTAGTGATGGTGGTAGTTTCACCTACTATTTTGCCAATATAC

AGGGCCGATTCACCATCTCCAGAGACAATACCAAGAACAACCTATACCTGCAAATGAACCATCTG

AAGTCTGAGGACGCAGGCATGTATTACTGTGCAAGAGATGTGGGCCTTACTACGTTTTGGTATTT

CGATGTCTGGGGCACAGGGACCACGGTCACCGTCTCCTCA

SEQ ID NO: 30

3E3 V$_H$ amino acid sequence
EVQLVESGGDLVKPGGSLKLSCVPSGFTFSSYAMSWVRQTPEKRLEWVATISDGGSFTYYFANIQG

RFTISRDNTKNNLYLQMNHLKSEDAGMYYCARDVGLTTFWYFDVWGTGTTVTVSS

SEQ ID NO: 31

3E3 V$_L$ nucleotide sequence
GACATTGTGCTGACACAGTCTCCTGCTTCCTTAACTATATCTCTGGGGCAGAGGGCCACCATCTC

CTGCAGGGCCAGCAAAAGTGTCAGTCCATCTGGCTATGATTTCATGCACTGGTATCAACAGAAG

CCAGGACAGCCGCCCAAACTCCTCATCAAGTATGCATCCGAACTAGAATCTGGGGTCCCTGGCA

GGTTCAGTGGCAGTGGGTCTGGGACAGATTTCACCCTCAACATCCATCCTGTGGAGGAAGAAGA

TGCTGCAACATATTTCTGTCAGCACAGTAGGGAGTTTCCGTTCACGTTCGGAGGGGGGACCAAG

CTGGAAATAAAA

SEQ ID NO: 32

3E3 V$_L$ amino acid sequence
DIVLTQSPASLTISLGQRATISCRASKSVSPSGYDFMHWYQQKPGQPPKLLIKYASELESGVPGRFSG

SGSGTDFTLNIHPVEEEDAATYFCQHSREFPFTFGGGTKLEIK

SEQ ID NO: 33

2B7 V$_H$ nucleotide sequence
GAAGTGCAGCTGGTGGAGTCTGGGGGAGGCTTAGTGAAACCTGGAGGGTCCCTGAAACTCTCC

TGTGCAGCCTCTGGATTCACTTTCAGTAACTATGCCATGTCTTGGGTTCGCCAGACTCCGGAAAA

GAGGCTGGAGTGGGTCGCGACCATTAGTGATGGTGGTGGTTACACCTACTATTTAGACAATGGA

```
CAGGGCCGATTCACCATCTCCAGAGACAATGCCAAGAACAACCTGTACCTGCAGATGAGCCATC

TGAAGTCTGAGGACACAGCCATGTATTACTGTGCAAGAGATGTGGGACTTACTACGTTTTGGTAC

TTCGATGTCTGGGGCACAGGGACCACGGTCACCGTCTCCTCA
```

SEQ ID NO: 34
2B7 V<sub>H</sub> amino acid sequence
```
EVQLVESGGGLVKPGGSLKLSCAASGFTFSNYAMSWVRQTPEKRLEWVATISDGGGYTYYLDNGQ

GRFTISRDNAKNNLYLQMSHLKSEDTAMYYCARDVGLTTFWYFDVWGTGTTVTVSS
```

SEQ ID NO: 35
2B7 V<sub>L</sub> nucleotide sequence
```
GACATTGTGCTGACACAGTCTCCTGTTTCCTTAGTTATATCTCTGGGGCAGAGGGCCACCATCTC

CTGCAGGGCCAGCAAAAGTGTCAGTCCATCTAGCTATAATTTCATGCACTGGTACCAACAGAGAC

CAGGACAGCCGCCCAAACTCCTCATCACGTATGCTTCCAACCTAGAATCTGGGGTCCCTGCCAG

GTTCAGTGGCAGTGGGTCTGGGACAGACTTCACCCTCAACATCCATCCTGTGGAGGAAGAGGAT

GCTGCAACATATTACTGTCAGCACAGTAGGGAGTTTCCGTTCACGTTCGGAGGGGGGACCAGGC

TGGAAATAAAA
```

SEQ ID NO: 36
2B7 V<sub>L</sub> amino acid sequence
```
DIVLTQSPVSLVISLGQRATISCRASKSVSPSSYNFMHWYQQRPGQPPKLLITYASNLESGVPARFSG

SGSGTDFTLNIHPVEEEDAATYYCQHSREFPFTFGGGTRLEIK
```

SEQ ID NO: 37
9G2 V<sub>H</sub> nucleotide sequence
```
GAAGTACAACTAGTGGAGTCTGGGGGAGGCTTAGTGGAGCCTGGAGGGTCCCTGAAACTCTCC

TGTGCAGCCTCTGGATTCACTTTCAGTAACTATGCCATGTCTTGGGTTCGCCAGACTCCGGAAAA

GAGGCTGGAGTGGGTCGCAACCATTAGTGATGGTGGTAGTTTCACCTACTATCTAGACAATGTAA

AGGGCCGATTCACCATCTCCAGAGACAATGCCAAGAACAACCTGTATTTGCAAATGAGCCATTTG

AAGTCTGACGACACAGCCATGTATTACTGTGCAAGAGATGTGGGACATACTACGTTTTGGTACTT

CGATGTCTGGGGCACAGGGACCACGGTCACCGTCTCCTCA
```

SEQ ID NO: 38
9G2 V<sub>H</sub> amino acid sequence
```
EVQLVESGGGLVEPGGSLKLSCAASGFTFSNYAMSWVRQTPEKRLEWVATISDGGSFTYYLDNVKG

RFTISRDNAKNNLYLQMSHLKSDDTAMYYCARDVGHTTFWYFDVWGTGTTVTVSS
```

SEQ ID NO: 39
9G2 V<sub>L</sub> nucleotide sequence
```
GACATTGTGCTGACACAGTCTCCTGTTTTCTTAGTTATATCTCTGGGGCAGAGGGCCACCATCTC

CTGCAGGGCCAGCAAAAGTGTCAGTGCATCTGGCTATAATTTCATGCACTGGTACCAACAGAAAC

CAGGACAGCCGCCCAAAGTCCTCATCAAGTATGCATCCAACCTAGAATCTGGGGTCCCTGCCAG

GTTCAGTGGCAGTGGGTCTGGGACAGACTTCACCCTCAACATCCATCCTGTGGAGGAGGAGGAT

GCTGTAACATATTACTGTCAGCACAGTAGGGAGTTTCCGTTCACGTTCGGAGGGGGGACCAAGC

TGGAAATAAAA
```

SEQ ID NO: 40
9G2 V<sub>L</sub> amino acid sequence
```
DIVLTQSPVFLVISLGQRATISCRASKSVSASGYNFMHWYQQKPGQPPKVLIKYASNLESGVPARFSG

SGSGTDFTLNIHPVEEEDAVTYYCQHSREFPFTFGGGTKLEIK
```

SEQ ID NO: 41
10G8 V<sub>H</sub> chimera nucleotide sequence
```
GAAATGCAACTGGTGGAGTCTGGGGAAGGCTTAGTGGAGCCTGGAGGGTCCCTGAAACTCTCC

TGTGCAGCCTCTGGATTCACTTTCAGTAACTATGCCATGTCTTGGGTTCGCCAGACTCCGGAAAA
```

```
GAGCCTGGAGTGGGTCGCAACCATTAGTGATGGTGGTAGTTTCACCTACTATCTAGACAATGTAA

GGGGCCGATTCACCATCTCCAGAGACAATGCCAAGAACAACCTGTATTTGCAAATGAGCCATTTG

AAGTCTGACGACACAGCCATGTATTACTGTGCAAGAGATGTGGGACATACTACCTTTTGGTACTT

CGATGTCTGGGGCTCAGGGACACTAGTGACCGTGTCCAGCGCCAGCACCAAGGGCCCCAGCGT

GTTCCCCCTGGCCCCCAGCAGCAAGAGCACCAGCGGCGGCACAGCCGCCCTGGGCTGCCTGG

TGAAGGACTACTTCCCCGAACCGGTGACCGTGTCCTGGAACAGCGGAGCCCTGACCAGCGGCG

TGCACACCTTCCCCGCCGTGCTGCAGAGCAGCGGCCTGTACAGCCTGAGCAGCGTGGTGACCG

TGCCCAGCAGCAGCCTGGGCACCCAGACCTACATCTGTAACGTGAACCACAAGCCCAGCAACAC

CAAGGTGGACAAGAAGGTGGAGCCCAAGAGCTGTGACAAGACCCACACCTGCCCCCCCTGCCC

TGCCCCCGAGCTGCTGGGAGGCCCCAGCGTGTTCCTGTTCCCCCCCAAGCCTAAGGACACCCT

GATGATCAGCAGAACCCCCGAGGTGACCTGTGTGGTGGTGGATGTGAGCCACGAGGACCCTGA

GGTGAAGTTCAACTGGTACGTGGACGGCGTGGAGGTGCACAATGCCAAGACCAAGCCCAGGGA

GGAGCAGTACAACAGCACCTACCGGGTGGTGTCCGTGCTGACCGTGCTGCACCAGGATTGGCT

GAACGGCAAGGAGTACAAGTGTAAGGTGTCCAACAAGGCCCTGCCTGCCCCTATCGAGAAACC

ATCAGCAAGGCCAAGGGCCAGCCCAGAGAGCCCCAGGTGTACACCCTGCCCCCTAGCAGAGAT

GAGCTGACCAAGAACCAGGTGTCCCTGACCTGCCTGGTGAAGGGCTTCTACCCCAGCGACATC

GCCGTGGAGTGGGAGAGCAACGGCCAGCCCGAGAACAACTACAAGACCACCCCCCCTGTGCTG

GACAGCGATGGCAGCTTCTTCCTGTACAGCAAGCTGACCGTGGACAAGAGCAGATGGCAGCAG

GGCAACGTGTTCAGCTGCTCCGTGATGCACGAGGCCCTGCACAATCACTACACCCAGAAGAGCC

TGAGCCTGTCCCTGGCAAG
```

SEQ ID NO: 42
10G8 $V_H$ chimera amino acid sequence
```
EMQLVESGEGLVEPGGSLKLSCAASGFTFSNYAMSWVRQTPEKSLEWVATISDGGSFTYYLDNVRG

RFTISRDNAKNNLYLQMSHLKSDDTAMYYCARDVGHTTFWYFDVWGSGTLVTVSSASTKGPSVFPL

APSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPGK
```

SEQ ID NO: 43
10G8 $V_L$ chimera nucleotide sequence
```
GACATTGTGCTGACACAGTCTCCTGTTTTCTTAGTTGTATCTCTGGGGCAGAGGGCCACCATCTC

CTGTAGGGCCAGCAAAAGTGTCAGTGCAGCTGGCTATAATTTCATGCACTGGTACCAACAGAAA

CCAGGACAGCCGCCCAAAGTCCTCATCAAGTATGCATCCAACCTAGAATCTGGGGTCCCTGCCA

GGTTCAGTGGCAGTGGGTCTGGGACAGACTTCACCCTCAACATCCATCCTGTGGAGGAGGAGG

ATGCTGTAACATATTACTGTCTGCACAGTAGGGAGTTTCCGTTCACGTTCGGAGGGGGGACCAA

CCTGGAAATAAAACGTACGGTGGCCGCCCCAGCGTGTTCATCTTCCCCCCAGCGATGAGCAG

CTGAAGAGCGGCACCGCCAGCGTGGTGTCTGCTGAACAACTTCTACCCCGGGAGGCCAAG

GTGCAGTGGAAGGTGGACAATGCCCTGCAGAGCGGCAACAGCCAGGAGAGCGTGACCGAGCA
```

```
GGACAGCAAGGACTCCACCTACAGCCTGAGCAGCACCCTGACCCTGAGCAAGGCCGACTACGA

GAAGCACAAGGTGTACGCCTGTGAGGTGACCCACCAGGGCCTGTCCAGCCCCGTGACCAAGAG

CTTCAACCGGGGCGAGTGC
```

SEQ ID NO: 44
10G8 V$_L$ chimera amino acid sequence
```
DIVLTQSPVFLVVSLGQRATISCRASKSVSAAGYNFMHWYQQKPGQPPKVLIKYASNLESGVPARFS

GSGSGTDFTLNIHPVEEEDAVTYYCLHSREFPFTFGGGTNLEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC
```

SEQ ID NO: 45
9G2 V$_H$ chimera nucleotide sequence
```
GAAGTACAACTGGTGGAGTCTGGGGGAGGCTTAGTGGAGCCTGGAGGGTCCCTGAAACTCTCC

TGTGCAGCCTCTGGATTCACTTTCAGTAACTATGCCATGTCTTGGGTTCGCCAGACTCCGGAAAA

GAGGCTGGAGTGGGTCGCAACCATTAGTGATGGTGGTAGTTTCACCTACTATCTAGACAATGTAA

AGGGCCGATTCACCATCTCCAGAGACAATGCCAAGAACAACCTGTATTTGCAAATGAGCCATTTG

AAGTCTGACGACACAGCCATGTATTACTGTGCAAGAGATGTGGGACATACTACGTTTTGGTACTT

CGATGTCTGGGGCACAGGGACACTAGTGACCGTGTCCAGCGCCAGCACCAAGGGCCCCAGCGT

GTTCCCCCTGGCCCCCAGCAGCAAGAGCACCAGCGGCGGCACAGCCGCCCTGGGCTGCCTGG

TGAAGGACTACTTCCCCGAACCGGTGACCGTGTCCTGGAACAGCGGAGCCCTGACCAGCGGCG

TGCACACCTTCCCCGCCGTGCTGCAGAGCAGCGGCCTGTACAGCCTGAGCAGCGTGGTGACCG

TGCCCAGCAGCAGCCTGGGCACCCAGACCTACATCTGTAACGTGAACCACAAGCCCAGCAACAC

CAAGGTGGACAAGAAGGTGGAGCCCAAGAGCTGTGACAAGACCCACACCTGCCCCCCCTGCCC

TGCCCCCGAGCTGCTGGGAGGCCCCAGCGTGTTCCTGTTCCCCCCCAAGCCTAAGGACACCCT

GATGATCAGCAGAACCCCCGAGGTGACCTGTGTGGTGGTGGATGTGAGCCACGAGGACCCTGA

GGTGAAGTTCAACTGGTACGTGGACGGCGTGGAGGTGCACAATGCCAAGACCAAGCCCAGGGA

GGAGCAGTACAACAGCACCTACCGGGTGGTGTCCGTGCTGACCGTGCTGCACCAGGATTGGCT

GAACGGCAAGGAGTACAAGTGTAAGGTGTCCAACAAGGCCCTGCCTGCCCCTATCGAGAAAACC

ATCAGCAAGGCCAAGGGCCAGCCCAGAGAGCCCCAGGTGTACACCCTGCCCCCTAGCAGAGAT

GAGCTGACCAAGAACCAGGTGTCCCTGACCTGCCTGGTGAAGGGCTTCTACCCCAGCGACATC

GCCGTGGAGTGGGAGAGCAACGGCCAGCCCGAGAACAACTACAAGACCACCCCCCCTGTGCTG

GACAGCGATGGCAGCTTCTTCCTGTACAGCAAGCTGACCGTGGACAAGAGCAGATGGCAGCAG

GGCAACGTGTTCAGCTGCTCCGTGATGCACGAGGCCCTGCACAATCACTACACCCAGAAGAGCC

TGAGCCTGTCCCCTGGCAAG
```

SEQ ID NO: 46
9G2 V$_H$ chimera amino acid sequence
```
EVQLVESGGGLVEPGGSLKLSCAASGFTFSNYAMSWVRQTPEKRLEWVATISDGGSFTYYLDNVKG

RFTISRDNAKNNLYLQMSHLKSDDTAMYYCARDVGHTTFWYFDVWGTGTLVTVSSASTKGPSVFPL

APSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPGK
```

```
                                                              SEQ ID NO: 47
9G2 V_L chimera nucleotide sequence
GACATTGTGCTGACACAGTCTCCTGTTTTCTTAGTTATATCTCTGGGGCAGAGGGCCACCATCTC

CTGCAGGGCCAGCAAAAGTGTCAGTGCATCTGGCTATAATTTCATGCACTGGTACCAACAGAAAC

CAGGACAGCCGCCCAAAGTCCTCATCAAGTATGCATCCAACCTAGAATCTGGGGTCCCTGCCAG

GTTCAGTGGCAGTGGGTCTGGGACAGACTTCACCCTCAACATCCATCCTGTGGAGGAGGAGGAT

GCTGTAACATATTACTGTCAGCACAGTAGGGAGTTTCCGTTCACGTTCGGAGGGGGGACCAAGC

TGGAAATAAAACGTACGGTGGCCGCCCCCAGCGTGTTCATCTTCCCCCCCAGCGATGAGCAGCT

GAAGAGCGGCACCGCCAGCGTGGTGTGTCTGCTGAACAACTTCTACCCCCGGGAGGCCAAGGT

GCAGTGGAAGGTGGACAATGCCCTGCAGAGCGGCAACAGCCAGGAGAGCGTGACCGAGCAGG

ACAGCAAGGACTCCACCTACAGCCTGAGCAGCACCCTGACCCTGAGCAAGGCCGACTACGAGA

AGCACAAGGTGTACGCCTGTGAGGTGACCCACCAGGGCCTGTCCAGCCCCGTGACCAAGAGCT

TCAACCGGGGCGAGTGC

SEQ ID NO: 48
9G2 V_L chimera amino acid sequence
DIVLTQSPVFLVISLGQRATISCRASKSVSASGYNFMHWYQQKPGQPPKVLIKYASNLESGVPARFSG

SGSGTDFTLNIHPVEEEDAVTYYCQHSREFPFTFGGGTKLEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC

SEQ ID NO: 49
IGHV3_7 human V_H germline acceptor nucleotide sequence
GAGGTGCAGCTGGTGGAGTCTGGGGGAGGCTTGGTCCAGCCTGGGGGGTCCCTGAGACTCTC

CTGTGCAGCCTCTGGATTCACCTTTAGTAGCTATTGGATGAGCTGGGTCCGCCAGGCTCCAGGG

AAGGGGCTGGAGTGGGTGGCCAACATAAAGCAAGATGGAAGTGAGAAATACTATGTGGACTCTG

TGAAGGGCCGATTCACCATCTCCAGAGACAACGCCAAGAACTCACTGTATCTGCAAATGAACAG

CCTGAGAGCCGAGGACACGGCTGTGTATTACTGTGCGAGA

SEQ ID NO: 50
IGHV3_7 human V_H germline acceptor amino acid sequence
EVQLVESGGGLVQPGGSLRLSCAASGFTFSSYWMSWVRQAPGKGLEWVANIKQDGSEKYYVDSVK

GRFTISRDNAKNSLYLQMNSLRAEDTAVYYCAR

SEQ ID NO: 51
IGKV4_1 human V_L germline acceptor nucleotide sequence
GACATCGTGATGACCCAGTCTCCAGACTCCCTGGCTGTGTCTCTGGGCGAGAGGGCCACCATCA

ACTGCAAGTCCAGCCAGAGTGTTTTATACAGCTCCAACAATAAGAACTACTTAGCTTGGTACCAG

CAGAAACCAGGACAGCCTCCTAAGCTGCTCATTTACTGGGCATCTACCCGGGAATCCGGGGTCC

CTGACCGATTCAGTGGCAGCGGGTCTGGGACAGATTTCACTCTCACCATCAGCAGCCTGCAGGC

TGAAGATGTGGCAGTTTATTACTGTCAGCAATATTATAGTACT

SEQ ID NO: 52
IGKV4_1 human V_L germline acceptor amino acid sequence
DIVMTQSPDSLAVSLGERATINCKSSQSVLYSSNNKNYLAWYQQKPGQPPKLLIYWASTRESGVPDR

FSGSGSGTDFTLTISSLQAEDVAVYYCQQYYST

SEQ ID NO: 53
10G8 Humanised V_H H0 nucleotide sequence -leto codon optimised
GAGGTGCAGCTGGTGGAAAGCGGCGGCGGCCTGGTCCAGCCCGGCGGGAGCCTGAGACTCTC

TTGCGCCGCTAGCGGCTTCACCTTCAGCAACTACGCCATGAGCTGGGTGAGGCAGGCCCCCGG
```

| Sequence Listing |
|---|
| CAAGGGCCTGGAGTGGGTGGCCACCATCAGCGACGGCGGCAGCTTCACCTACTATCTGGACAA |
| CGTGAGGGGCAGGTTCACCATCAGCAGGGACAACGCCAAGAACAGCCTGTACCTGCAGATGAA |
| CAGCCTGAGGGCCGAGGATACCGCCGTGTACTACTGCGCCAGGGACGTCGGCCACACCACCTT |
| CTGGTACTTCGACGTCTGGGGCAGGGGCACACTAGTGACCGTGTCCAGC |

SEQ ID NO: 54
10G8 Humanised V<sub>H</sub> H0 amino acid sequence
EVQLVESGGGLVQPGGSLRLSCAASGFTFSNYAMSWVRQAPGKGLEWVATISDGGSFTYYLDNVR

GRFTISRDNAKNSLYLQMNSLRAEDTAVYYCARDVGHTTFWYFDVWGRGTLVTVSS

SEQ ID NO: 55
10G8 Humanised V<sub>H</sub> H1 nucleotide sequence -leto codon optimised
GAGATGCAGCTGGTGGAAAGCGGCGGCGGCCTGGTCCAGCCCGGCGGGAGCCTGAGACTCTC

TTGCGCCGCTAGCGGCTTCACCTTCAGCAACTACGCCATGAGCTGGGTGAGGCAGGCCCCCGG

CAAGGGCCTGGAGTGGGTGGCCACCATCAGCGACGGCGGCAGCTTCACCTACTATCTGGACAA

CGTGAGGGGCAGGTTCACCATCAGCAGGGACAACGCCAAGAACAGCCTGTACCTGCAGATGAA

CAGCCTGAGGGCCGAGGATACCGCCGTGTACTACTGCGCCAGGGACGTCGGCCACACCACCTT

CTGGTACTTCGACGTCTGGGGCAGGGGCACACTAGTGACCGTGTCCAGC

SEQ ID NO: 56
10G8 Humanised V<sub>H</sub> H1 amino acid sequence
EMQLVESGGGLVQPGGSLRLSCAASGFTFSNYAMSWVRQAPGKGLEWVATISDGGSFTYYLDNVR

GRFTISRDNAKNSLYLQMNSLRAEDTAVYYCARDVGHTTFWYFDVWGRGTLVTVSS

SEQ ID NO: 57
10G8 Humanised V<sub>H</sub> H2 nucleotide sequence -leto codon optimised
GAGGTGCAGCTGGTGGAAAGCGGCGGCGGCCTGGTCCAGCCCGGCGGGAGCCTGAGACTCTC

TTGCGCCGCTAGCGGCTTCACCTTCAGCAACTACGCCATGAGCTGGGTGAGGCAGGCCCCCGG

CAAGGGCCTGGAGTGGGTGGCCACCATCAGCGACGGCGGCAGCTTCACCTACTATCTGGACAA

CGTGAGGGGCAGGTTCACCATCAGCAGGGACAACGCCAAGAACAGCCTGTACCTGCAGATGAA

CAGCCTGAGGGCCGAGGATACCGCCGTGTACTACTGCGCCAGGGACGTCGGCCACACCACCTT

CTGGTACTTCGACGTCTGGGGCTCCGGCACACTAGTGACCGTGTCCAGC

SEQ ID NO: 58
10G8 Humanised V<sub>H</sub> H2 amino acid sequence
EVQLVESGGGLVQPGGSLRLSCAASGFTFSNYAMSWVRQAPGKGLEWVATISDGGSFTYYLDNVR

GRFTISRDNAKNSLYLQMNSLRAEDTAVYYCARDVGHTTFWYFDVWGSGTLVTVSS

SEQ ID NO: 59
10G8 Humanised V<sub>L</sub> L0 nucleotide sequence -leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGCTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

GAGGACGTCGCCGTGTACTACTGCCTGCACAGCAGGGAGTTCCCCTTCACCTTTGGCGGCGGC

ACCAAGGTGGAGATCAAG

SEQ ID NO: 60
10G8 Humanised V<sub>L</sub> L0 amino acid sequence
DIVMTQSPDSLAVSLGERATINCRASKSVSAAGYNFMHWYQQKPGQPPKLLIYYASNLESGVPDRFS

GSGSGTDFTLTISSLQAEDVAVYYCLHSREFPFTFGGGTKVEIK

| Sequence Listing |
|---|

SEQ ID NO: 61

10G8 Humanised V_L L1 nucleotide sequence -leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGGTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

GAGGACGTCGCCGTGTACTACTGCCTGCACAGCAGGGAGTTCCCCTTCACCTTTGGCGGCGGC

ACCAAGGTGGAGATCAAG

SEQ ID NO: 62

10G8 Humanised V_L L1 amino acid sequence
DIVMTQSPDSLAVSLGERATINCRASKSVSAAGYNFMHWYQQKPGQPPKVLIYYASNLESGVPDRFS

GSGSGTDFTLTISSLQAEDVAVYYCLHSREFPFTFGGGTKVEIK

SEQ ID NO: 63

10G8 Humanised V_L L2 nucleotide sequence- leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGCTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

GAGGACGTCGTGGTGTACTACTGCCTGCACAGCAGGGAGTTCCCCTTCACCTTTGGCGGCGGC

ACCAAGGTGGAGATCAAG

SEQ ID NO: 64

10G8 Humanised V_L L2 amino acid sequence
DIVMTQSPDSLAVSLGERATINCRASKSVSAAGYNFMHWYQQKPGQPPKLLIYYASNLESGVPDRFS

GSGSGTDFTLTISSLQAEDVVVYYCLHSREFPFTFGGGTKVEIK

SEQ ID NO: 65

10G8 Humanised V_L L3 nucleotide sequence - leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGCTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

GAGGACGTCGCCGTGTACTACTGCCTGCACAGCAGGGAGTTCCCCTTCACCTTTGGCGGCGGC

ACCAACGTGGAGATCAAG

SEQ ID NO: 66

10G8 Humanised V_L L3 amino acid sequence
DIVMTQSPDSLAVSLGERATINCRASKSVSAAGYNFMHWYQQKPGQPPKLLIYYASNLESGVPDRFS

GSGSGTDFTLTISSLQAEDVAVYYCLHSREFPFTFGGGTNVEIK

SEQ ID NO: 67

10G8 Humanised V_L L4 nucleotide sequence -leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGGTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

GAGGACGTCGTGGTGTACTACTGCCTGCACAGCAGGGAGTTCCCCTTCACCTTTGGCGGCGGC

ACCAACGTGGAGATCAAG

Sequence Listing

SEQ ID NO: 68
10G8 Humanised V_L L4 amino acid sequence
DIVMTQSPDSLAVSLGERATINCRASKSVSAAGYNFMHWYQQKPGQPPKVLIYYASNLESGVPDRFS

GSGSGTDFTLTISSLQAEDVVVYYCLHSREFPFTFGGGTNVEIK

SEQ ID NO: 69
Mature H0 heavy chain nucleotide sequence -leto codon optimised
GAGGTGCAGCTGGTGGAAAGCGGCGGCGGCCTGGTCCAGCCCGGCGGGAGCCTGAGACTCTC

TTGCGCCGCTAGCGGCTTCACCTTCAGCAACTACGCCATGAGCTGGGTGAGGCAGGCCCCCGG

CAAGGGCCTGGAGTGGGTGGCCACCATCAGCGACGGCGGCAGCTTCACCTACTATCTGGACAA

CGTGAGGGGCAGGTTCACCATCAGCAGGGACAACGCCAAGAACAGCCTGTACCTGCAGATGAA

CAGCCTGAGGGCCGAGGATACCGCCGTGTACTACTGCGCCAGGGACGTCGGCCACACCACCTT

CTGGTACTTCGACGTCTGGGGCAGGGGCACACTAGTGACCGTGTCCAGCGCCAGCACCAAGGG

CCCCAGCGTGTTCCCCCTGGCCCCCAGCAGCAAGAGCACCAGCGGCGGCACAGCCGCCCTGG

GCTGCCTGGTGAAGGACTACTTCCCCGAACCGGTGACCGTGTCCTGGAACAGCGGAGCCCTGA

CCAGCGGCGTGCACACCTTCCCCGCCGTGCTGCAGAGCAGCGGCCTGTACAGCCTGAGCAGC

GTGGTGACCGTGCCCAGCAGCAGCCTGGGCACCCAGACCTACATCTGTAACGTGAACCACAAG

CCCAGCAACACCAAGGTGGACAAGAAGGTGGAGCCCAAGAGCTGTGACAAGACCCACACCTGC

CCCCCCTGCCCTGCCCCCGAGCTGCTGGGAGGCCCCAGCGTGTTCCTGTTCCCCCCCAAGCCT

AAGGACACCCTGATGATCAGCAGAACCCCCGAGGTGACCTGTGTGGTGGTGGATGTGAGCCAC

GAGGACCCTGAGGTGAAGTTCAACTGGTACGTGGACGGCGTGGAGGTGCACAATGCCAAGACC

AAGCCCAGGGAGGAGCAGTACAACAGCACCTACCGGGTGGTGTCCGTGCTGACCGTGCTGCAC

CAGGATTGGCTGAACGGCAAGGAGTACAAGTGTAAGGTGTCCAACAAGGCCCTGCCTGCCCCTA

TCGAGAAAACCATCAGCAAGGCCAAGGGCCAGCCCAGAGAGCCCCAGGTGTACACCCTGCCCC

CTAGCAGAGATGAGCTGACCAAGAACCAGGTGTCCCTGACCTGCCTGGTGAAGGGCTTCTACCC

CAGCGACATCGCCGTGGAGTGGGAGAGCAACGGCCAGCCCGAGAACAACTACAAGACCACCCC

CCCTGTGCTGGACAGCGATGGCAGCTTCTTCCTGTACAGCAAGCTGACCGTGGACAAGAGCAGA

TGGCAGCAGGGCAACGTGTTCAGCTGCTCCGTGATGCACGAGGCCCTGCACAATCACTACACC

CAGAAGAGCCTGAGCCTGTCCCCTGGCAAG

SEQ ID NO: 70
Mature H0 heavy chain amino acid sequence
EVQLVESGGGLVQPGGSLRLSCAASGFTFSNYAMSWVRQAPGKGLEWVATISDGGSFTYYLDNVR

GRFTISRDNAKNSLYLQMNSLRAEDTAVYYCARDVGHTTFWYFDVWGRGTLVTVSSASTKGPSVFP

LAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID NO: 71
Mature L1 light chain nucleotide sequence - leto codon optimised
GACATCGTGATGACTCAGAGCCCCGATAGCCTGGCCGTGAGCCTGGGCGAAAGGGCCACCATC

AACTGCAGGGCCAGCAAGAGCGTGAGCGCTGCCGGCTACAACTTCATGCACTGGTACCAGCAG

AAGCCCGGCCAGCCCCCCAAGGTGCTGATCTACTACGCCTCCAACCTGGAGAGCGGCGTGCCA

GACAGGTTCAGCGGATCTGGCAGCGGCACCGACTTCACCCTGACCATCTCAAGCCTGCAGGCC

```
GAGGACGTCGCCGTGTACTACTGCCTGCACAGCAGGGAGTTCCCCTTCACCTTTGGCGGCGGC

ACCAAGGTGGAGATCAAGCGTACGGTGGCCGCCCCCAGCGTGTTCATCTTCCCCCCCAGCGAT

GAGCAGCTGAAGAGCGGCACCGCCAGCGTGGTGTGTCTGCTGAACAACTTCTACCCCCGGGAG

GCCAAGGTGCAGTGGAAGGTGGACAATGCCCTGCAGAGCGGCAACAGCCAGGAGAGCGTGAC

CGAGCAGGACAGCAAGGACTCCACCTACAGCCTGAGCAGCACCCTGACCCTGAGCAAGGCCGA

CTACGAGAAGCACAAGGTGTACGCCTGTGAGGTGACCCACCAGGGCCTGTCCAGCCCCGTGAC

CAAGAGCTTCAACCGGGGCGAGTGC
```

SEQ ID NO: 72
Mature L1 light chain amino acid sequence
```
DIVMTQSPDSLAVSLGERATINCRASKSVSAAGYNFMHWYQQKPGQPPKVLIYYASNLESGVPDRFS

GSGSGTDFTLTISSLQAEDVAVYYCLHSREFPFTFGGGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC
```

SEQ ID NO: 73
Humanised V$_H$ variant H0 (IGHV3_23 CDRH1) nucleotide
sequence- leto codon optimised
```
GAGGTGCAGCTGGTGGAAAGCGGCGGCGGCCTGGTCCAGCCCGGCGGGAGCCTGAGACTCTC

TTGCGCCGCTAGCGGCTTCACCTTCAGCAGCTACGCCATGAGCTGGGTGAGGCAGGCCCCCGG

CAAGGGCCTGGAGTGGGTGGCCACCATCAGCGACGGCGGCAGCTTCACCTACTATCTGGACAA

CGTGAGGGGCAGGTTCACCATCAGCAGGGACAACGCCAAGAACAGCCTGTACCTGCAGATGAA

CAGCCTGAGGGCCGAGGATACCGCCGTGTACTACTGCGCCAGGGACGTCGGCCACACCACCTT

CTGGTACTTCGACGTCTGGGGCAGGGGCACACTAGTGACCGTGTCCAGC
```

SEQ ID NO: 74
Humanised V$_H$ variant H0 (IGHV3_23 CDRH1) amino acid sequence
```
EVQLVESGGGLVQPGGSLRLSCAASGFTFSSYAMSWVRQAPGKGLEWVATISDGGSFTYYLDNVR

GRFTISRDNAKNSLYLQMNSLRAEDTAVYYCARDVGHTTFWYFDVWGRGTLVTVSS
```

SEQ ID NO: 75
Mature H0 (IGHV3_23 CDRH1) heavy chain nucleotide
sequence - leto codon optimised
```
GAGGTGCAGCTGGTGGAAAGCGGCGGCGGCCTGGTCCAGCCCGGCGGGAGCCTGAGACTCTC

TTGCGCCGCTAGCGGCTTCACCTTCAGCAGCTACGCCATGAGCTGGGTGAGGCAGGCCCCCGG

CAAGGGCCTGGAGTGGGTGGCCACCATCAGCGACGGCGGCAGCTTCACCTACTATCTGGACAA

CGTGAGGGGCAGGTTCACCATCAGCAGGGACAACGCCAAGAACAGCCTGTACCTGCAGATGAA

CAGCCTGAGGGCCGAGGATACCGCCGTGTACTACTGCGCCAGGGACGTCGGCCACACCACCTT

CTGGTACTTCGACGTCTGGGGCAGGGGCACACTAGTGACCGTGTCCAGCGCCAGCACCAAGGG

CCCCAGCGTGTTCCCCCTGGCCCCCAGCAGCAAGAGCACCAGCGGCGGCACAGCCGCCCTGG

GCTGCCTGGTGAAGGACTACTTCCCCGAACCGGTGACCGTGTCCTGGAACAGCGGAGCCCTGA

CCAGCGGCGTGCACACCTTCCCCGCCGTGCTGCAGAGCAGCGGCCTGTACAGCCTGAGCAGC

GTGGTGACCGTGCCCAGCAGCAGCCTGGGCACCCAGACCTACATCTGTAACGTGAACCACAAG

CCCAGCAACACCAAGGTGGACAAGAAGGTGGAGCCCAAGAGCTGTGACAAGACCCACACCTGC

CCCCCCTGCCCTGCCCCCGAGCTGCTGGGAGGCCCCAGCGTGTTCCTGTTCCCCCCCAAGCCT

AAGGACACCCTGATGATCAGCAGAACCCCCGAGGTGACCTGTGTGGTGGTGGATGTGAGCCAC

GAGGACCCTGAGGTGAAGTTCAACTGGTACGTGGACGGCGTGGAGGTGCACAATGCCAAGACC
```

```
AAGCCCAGGGAGGAGCAGTACAACAGCACCTACCGGGTGGTGTCCGTGCTGACCGTGCTGCAC

CAGGATTGGCTGAACGGCAAGGAGTACAAGTGTAAGGTGTCCAACAAGGCCCTGCCTGCCCCTA

TCGAGAAAACCATCAGCAAGGCCAAGGGCCAGCCCAGAGAGCCCCAGGTGTACACCCTGCCCC

CTAGCAGAGATGAGCTGACCAAGAACCAGGTGTCCCTGACCTGCCTGGTGAAGGGCTTCTACCC

CAGCGACATCGCCGTGGAGTGGGAGAGCAACGGCCAGCCCGAGAACAACTACAAGACCACCCC

CCCTGTGCTGGACAGCGATGGCAGCTTCTTCCTGTACAGCAAGCTGACCGTGGACAAGAGCAGA

TGGCAGCAGGGCAACGTGTTCAGCTGCTCCGTGATGCACGAGGCCCTGCACAATCACTACACC

CAGAAGAGCCTGAGCCTGTCCCCTGGCAAG
```

SEQ ID NO: 76

Mature H0 (IGHV3_23 CDRH1) heavy chain amino acid sequence
```
EVQLVESGGGLVQPGGSLRLSCAASGFTFSSYAMSWVRQAPGKGLEWVATISDGGSFTYYLDNVR

GRFTISRDNAKNSLYLQMNSLRAEDTAVYYCARDVGHTTFWYFDVWGRGTLVTVSSASTKGPSVFP

LAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK
```

SEQ ID NO: 77

Human heavy chain germline IGHV3_23 CDRH1
SYAMS

SEQ ID NO: 78

Human light chain germline IGKV1_5 CDRL2
KASSLES

SEQ ID NO: 79

15E10 Humanised Heavy Chain Amino Acid Sequence:
```
QVQLVESGGGVVQPGRSLRLSCAASGFSLTNYGVHWVRQAPGKGLEWVAVIWRGGSTDYNAAFM

SRFTISKDNSKNTLYLQMNSLRAEDTAVYYCAKSPNSNFYWYFDVWGRGTLVTVSSASTKGPSVFPL

APSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPGK
```

SEQ ID NO: 80

15E10 Humanised Light Chain Amino Acid Sequence:
```
EIVLTQSPATLSLSPGERATLSCSGSSSVSYMYWYQQKPGQAPRLLIEDTSNLASGIPARFSGSGSGT

DYTLTISNLEPEDFAVYYCQQWSSYPPTFGQGTKLEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSS

PVTKSFNRGEC
```

SEQ ID NO: 81

15E10 Humanised VH B3
```
QVQLVESGGGVVQPGRSLRLSCAASGFSLTNYGVHWVRQAPGKGLEWVAVIWRGGSTDYNAAFM

SRFTISKDNSKNTLYLQMNSLRAEDTAVYYCAKSPNSNFYWYFDVWGRGTLV (TVSS)
```

SEQ ID NO: 82

15E10 Humanised VL L2
```
EIVLTQSPATLSLSPGERATLSCSGSSSVSYMYWYQQKPGQAPRLLIEDTSNLASGIPARFSGSGSGT

DYTLTISNLEPEDFAVYYCQQWSSYPPTFGQGTKLEIK
```

SEQ ID NO: 83
Human OSM polynucleotide sequence
ATGGGGGTACTGCTCACACAGAGGACGCTGCTCAGTCTGGTCCTTGCACTC

CTGTTTCCAAGCATGGCGAGCATGGCGGCTATAGGCAGCTGCTCGAAAGAG

TACCGCGTGCTCCTTGGCCAGCTCCAGAAGCAGACAGATCTCATGCAGGAC

ACCAGCAGACTCCTGGACCCCTATATACGTATCCAAGGCCTGGATGTTCCT

AAACTGAGAGAGCACTGCAGGGAGCGCCCCGGGGCCTTCCCCAGTGAGGAG

ACCCTGAGGGGCTGGGCAGGCGGGGCTTCCTGCAGACCCTCAATGCCACA

CTGGGCTGCGTCCTGCACAGACTGGCCGACTTAGAGCAGCGCCTCCCCAAG

GCCCAGGATTTGGAGAGGTCTGGGCTGAACATCGAGGACTTGGAGAAGCTG

CAGATGGCGAGGCCGAACATCCTCGGGCTCAGGAACAACATCTACTGCATG

GCCCAGCTGCTGGACAACTCAGACACGGCTGAGCCCACGAAGGCTGGCCGG

GGGGCCTCTCAGCCGCCCACCCCCACCCCTGCCTCGGATGCTTTTCAGCGC

AAGCTGGAGGGCTGCAGGTTCCTGCATGGCTACCATCGCTTCATGCACTCA

GTGGGGCGGGTCTTCAGCAAGTGGGGGGAGAGCCCGAACCGGAGCCGGAGA

CACAGCCCCCACCAGGCCCTGAGGAAGGGGGTGCGCAGGACCAGACCCTCC

AGGAAAGGCAAGAGACTCATGACCAGGGGACAGCTGCCCCGGTAG

SEQ ID NO: 84
Human OSM amino acid sequence
MGVLLTQRTLLSLVLALLFPSMASMAAIGSCSKEYRVLLGQLQKQTDLMQD

TSRLLDPYIRIQGLDVPKLREHCRERPGAFPSEETLRGLGRRGFLQTLNAT

LGCVLHRLADLEQRLPKAQDLERSGLNIEDLEKLQMARPNILGLRNNIYCM

AQLLDNSDTAEPTKAGRGASQPPTPTPASDAFQRKLEGCRFLHGYHRFMHS

VGRVFSKWGESPNRSRRHSPHQALRKGVRRTRPSRKGKRLMTRGQLPR.

---

The invention claimed is:

1. A composition comprising, an antigen binding protein that specifically binds to Oncostatin M (OSM) and inhibits the binding of OSM to the gp130 receptor, wherein the antigen binding protein comprises SEQ ID NO: 3 (CDRH3), SEQ ID NO: 2 (CDRH2), SEQ ID NO: 4 (CDRL1), and SEQ ID NO: 6 (CDRL3), and does not directly interact with OSM site II residues.

2. The antigen binding protein according to claim 1, wherein the antigen binding protein does not directly bind to residues Q20, G120, Q16, and N124 of SEQ ID NO: 84.

3. The antigen binding protein according to claim 1, wherein the antigen binding protein interacts with at least one of the residues selected from the group consisting of: 82, 83, 84, 90, 94, 112, 115, 122, 123, and 152 of SEQ ID NO: 84.

4. The antigen binding protein according to claim 1, wherein the antigen binding protein further comprises SEQ ID NO: 1 (CDRH1) and SEQ ID NO: 5 (CDRL2).

5. The antigen binding protein according to claim 1, wherein the antigen binding protein comprises a CDR H1 and CDR L2 that does not interact directly with OSM.

6. The antigen binding protein according to claim 1, further comprising a heavy chain variable region encoded by SEQ ID NO:73 and a light chain variable region encoded by SEQ ID NO:71.

7. The antigen binding protein according to claim 1, further comprising a heavy chain variable region of SEQ ID NO:74 and a light chain variable region of SEQ ID NO:72.

8. The antigen binding protein according to claim 1, wherein the antigen binding protein is a humanised antibody.

9. The antigen binding protein according to claim 8, wherein the antibody is IgG1.

10. The antigen binding protein according to claim 8, wherein when bound to OSM the co-crystal comprises a unit cell having dimensions of about a=168.525 A, b=81.614 A, c=55.540 A and beta=106.60 degrees.

11. The antigen binding protein according to claim 1, wherein the antigen binding protein additionally binds non-human primate OSM.

12. The antigen binding protein according to claim 1, wherein the antigen binding protein binds OSM with an affinity of less than 40 pm.

13. The antigen binding protein according to claim 1, wherein the antigen binding protein does not compete with an antibody that has a heavy chain of SEQ ID NO:79 and a light chain of SEQ ID NO: 80 in a competition ELISA assay.

14. An antigen binding protein which binds to both Marmoset and human OSM with an affinity stronger than 1 nM when measured by Biacore or kinexa, wherein the antigen binding protein comprises SEQ ID NO: 3 (CDRH3), SEQ ID NO: 2 (CDRH2), SEQ ID NO: 4 (CDRL1), and SEQ ID NO: 6 (CDRL3).

15. A polynucleotide encoding a heavy chain of an antigen binding protein according to SEQ ID NO: 74 and comprises a polynucleotide encoding a light chain of an antigen binding protein according to SEQ ID NO: 72.

16. A pharmaceutical composition comprising an antigen binding protein according to claim 1 and a pharmaceutically acceptable carrier.

* * * * *